US008236329B2

(12) United States Patent
Kwon

(10) Patent No.: US 8,236,329 B2
(45) Date of Patent: *Aug. 7, 2012

(54) MICELLE ENCAPSULATION OF THERAPEUTIC AGENTS

(75) Inventor: Glen S. Kwon, Waunakee, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/890,450

(22) Filed: Sep. 24, 2010

(65) Prior Publication Data

US 2011/0076308 A1    Mar. 31, 2011

Related U.S. Application Data

(60) Provisional application No. 61/375,681, filed on Aug. 20, 2010, provisional application No. 61/245,918, filed on Sep. 25, 2009.

(51) Int. Cl.
*A61K 9/00* (2006.01)
(52) U.S. Cl. .......... 424/400; 514/449; 514/27; 514/291; 514/183
(58) Field of Classification Search ................ 424/400; 514/449, 27, 291, 183
See application file for complete search history.

(56) References Cited

U.S. PATENT DOCUMENTS

| | | | |
|---|---|---|---|
| 4,261,989 A | 4/1981 | Sasaki et al. | |
| 4,745,160 A | 5/1988 | Churchill et al. | |
| 5,580,899 A | 12/1996 | Mayhew | |
| 6,284,267 B1 | 9/2001 | Aneja | |
| 6,322,805 B1 * | 11/2001 | Kim et al. ............. | 424/426 |
| 6,322,810 B1 | 11/2001 | Alkan-Onyuksel et al. | |
| 6,413,537 B1 | 7/2002 | Kwon et al. | |
| 6,500,916 B1 | 12/2002 | Hashida et al. | |
| 6,939,561 B2 | 9/2005 | Kwon et al. | |
| 7,211,562 B2 | 5/2007 | Rosen et al. | |
| 2002/0169274 A1 | 11/2002 | Eisenberg et al. | |
| 2003/0104989 A1 | 6/2003 | Hashida et al. | |
| 2003/0114450 A1 | 6/2003 | Santi et al. | |
| 2004/0005351 A1 | 1/2004 | Kwon et al. | |
| 2004/0005357 A1 * | 1/2004 | Sherman ................ | 424/468 |
| 2004/0116360 A1 | 6/2004 | Kwon | |
| 2005/0026893 A1 | 2/2005 | Johnson, Jr. et al. | |
| 2005/0256097 A1 | 11/2005 | Zhong et al. | |
| 2006/0122290 A1 | 6/2006 | Hubbell et al. | |
| 2006/0135430 A1 | 6/2006 | Chan et al. | |
| 2006/0240092 A1 | 10/2006 | Breitenkamp et al. | |
| 2006/0251710 A1 * | 11/2006 | Kwon et al. ........... | 424/450 |
| 2007/0059271 A1 | 3/2007 | Kataoka et al. | |
| 2007/0167422 A1 | 7/2007 | Yu et al. | |
| 2009/0232762 A1 | 9/2009 | Xiong | |
| 2010/0203114 A1 * | 8/2010 | Kwon et al. ........... | 424/450 |

FOREIGN PATENT DOCUMENTS

| | | |
|---|---|---|
| CN | 101081207 | 12/2007 |
| EP | 0166596 | 1/1986 |
| WO | WO 2008/106129 * | 9/2004 |
| WO | WO 2006/110473 | 10/2006 |
| WO | WO2009009067 | 1/2009 |

OTHER PUBLICATIONS

Nguyen et al. Ann. Thorac. Surg 72: pp. 371-379 (2001).*
Roforth. Anti-cancer Drugs 19: pp. 681-699 (2008).*
Bagatell, et al. "Hsp90 Inhibitors Deplete Key AntiApoptotic Proteins in Pediatric Solid Tumor Cells and Demonstrate Synergistic Anticancer Activity with Cisplatin" Int. J. Cancer, 2005, vol. 113, pp. 179-188.
Blagosklonny et al., "The Hsp90 Inhibitor Geldanamycin selectively Sensitizes Bcr-Abl-expressing Leukemia Cells to Cytotoxic Chemotherapy' Leukemia", 2001, vol. 15, pp. 1537-1543.
Chou, "Drug Combination Studies and Their Synergy Quantification Using the Chou-Talalay Method", American Association for Cancer Research; 70(2) Jan. 15, 2010, pp. 440-446.
Erlichman, "Tanespimycin: the opportunities and challenges of targeting heat shock protein 90", Expert Opin. Investig. Drugs (2009) 18(6):861-868.
Fung et al., "Concurrent and Sequential Administration of Chemotherapy and the Mammalian Target of Rapamycin Inhibitor Temsirolimus in Human Cancer Cells and Xenografts", Clin Cancer Res 2009;15(17) Sep. 1, 2009, pp. 5389-5395.
Garber, "Targeting mTOR: Something Old, Something New", JNCI vol. 101, Issue 5, Mar. 4, 2009, pp. 288-290.
Kim, T.-Y., et al., "Phase I and Pharmacokinetic Study of Genexol-PM, a Cremophor-Free, Polymeric Miccelle-Formulated Paclitaxel, in Patients with Advanced Malignancies", *Clinical Cancer Research*, 10, (2004), 3708-3716.
Kwon et al., Polymeric Micelles for Nano-Combination Drug Delivery, 17th Int. Symp. Microencapsulation Abstract, Sep. 29, 2009, 2 pgs.
Kwon, G. S., "Diblock Copolymer Nanoparticles for Drug Delivery", *Critical Reviews in Therapeutic Drug Carrier Systems*, 15(5), (1998), 481-512.
Mimnaugh et al., "Simultaneous Inhibition of Hsp90 and the Proteasome promotes Protien Ubiquitination, Causes endoplasmic Reticulum-derived cytosolic vacuolization, and Enhances Antitumor ActivitY Molecular Cancer Therapeutics", 2004, vol. 3 (5), pp. 551-566.

(Continued)

*Primary Examiner* — Anoop Singh
*Assistant Examiner* — Anna Falkowitz
(74) *Attorney, Agent, or Firm* — Clise, Billion & Cyr, P.A.; Michael H. Haukaas

(57) ABSTRACT

The invention provides active agents, such as paclitaxel, rapamycin, or 17-AAG, encapsulated by safe poly(ethylene glycol)-block-poly(lactic acid) ("PEG-b-PLA") micelles. The compositions provide effective solubilization of drug combinations, such as paclitaxel, rapamycin, and 17-AAG, as well as others described herein. A significant advantage of PEG-b-PLA as a carrier is that it is less toxic than Cremophor® EL or DMSO, which are used in currently known compositions. Additionally, PEG-b-PLA micelles are easier to handle than DMSO and they do not possess a foul odor, which is a problem with formulations currently in clinical trials. Accordingly, the invention provides stable and biocompatible drug formulations that improve bioavailabilty without causing toxicity. It was also found that larger doses of individual drugs in micelle formulations can be administered compared to non-micelle formulations.

22 Claims, 15 Drawing Sheets

OTHER PUBLICATIONS

Mondesire et al., "Targeting Mammalian Target of Rapamycin Synergistically Enhances Chemotherapy-Induced Cytotoxicity in Breast Cancer Cells", Clin. Cancer Res. vol. 10, Oct. 15, 2004, pp. 7031-7042.

National Cancer Institute, NCI Cancer Bulletin, Jan. 17, 2006, vol. 3, No. 3, 8 pgs.

Nguyen, D. M., et al., "Enhancement of Paclitaxel-Mediated Cytotoxicity in Lung Cancer Cells by 17-Allylamino Geldanamycin: In Vitro and In Vivo Analysis", *Ann. Thorac. Surg.*, 72, (2001), 371-379.

Prince George, et al. 'Combination of Histone Deacetylase Inhibitor LBH589 and the hsp90 Inhibitor 17-AAG is highly Active against Human CML-BC Cells and AML Cells with Activating Mutation of FLT-3' Blood, Feb. 15, 2005, vol. 105, No. 4, pp. 1768-1176.

Putnam, D., et al., "Polymer-based gene delivery with low cytotoxicity by a unique balance of side-chain termini", *Proc. Natl. Acad. Sci. USA*, 98(3), (2001),1200-1205.

Roforth and Tan, Combination of rapamycin and 17-allylamino-17-demethoxygeldanamycin abrogates Akt activation and potentiates mTOR blockade in breast cancer cells, Anti-Cancer Drugs 2008, vol. 19 No. 7, pp. 681-688.

Shin et al., "Multi-drug loaded polymeric micelles for simultaneous delivery of poorly soluble anticancer drugs", Journal of Controlled Release, 2009, 7 pgs.

Solit, D. B., et al., "Phase 1 pharmacokinetic and pharmacodynamic trial of docetaxel and 17AAG (17-allylamino-17-demethoxygeldanamycin)", *Journal of Clinical Oncology*, 22(No. 14S) (Suppl.), Proceedings, ASCO Annual Meeting (Abstract No. 3032), (Jul. 15, 2004), 2 pgs.

Xiong et al., "A Cremophor-Free Formulation for Tanespimycin (17-AAG) Using PEO-b-PDLLA Micelles: Characterization and Pharmacokinetics in Rats", Journal of Pharmaceutical Sciences, vol. 98, No. 4, Apr. 2009, pp. 1577-1586.

Yu et al., "mTOR, a novel target in breast cancer: the effect of CCI-779, an mTOR inhibitor, in preclinical models of breast cancer", Endocrine-Related Cancer (2001) 8, pp. 249-258.

International Search Report and Written Opinion for PCT/US2010/050276, mailed Oct. 7, 2011, 22 pgs.

Mondesire, W. H., et al.; "Targeting Mammalian Target of Rapamycin Synergistically Enhances Chemotherapy-Induced Cytotoxicity in Breast Cancer Cells," Clinical Cancer Research, vol. 10, No. 20; Oct. 15, 2004, pp. 7031-7042.

\* cited by examiner

MICELLE ENCAPSULATION OF THERAPEUTIC AGENTS

RELATED APPLICATIONS

This application claims priority under 35 U.S.C. §119(e) to U.S. Provisional Patent Application Nos. 61/245,918, filed Sep. 25, 2009, and 61/375,681, filed Aug. 20, 2010, which applications are incorporated herein by reference in their entirety.

GOVERNMENT SUPPORT

This invention was made with government support under Grant No. AI043346, awarded by the National Institutes of Health. The United States Government has certain rights in the invention.

BACKGROUND OF THE INVENTION

As research on cancer progresses, it is increasingly evident that single drug formulations provide only limited success. Many researchers therefore aim to develop suitable combination therapies. One of the most important requirements of combination therapy is a simple and efficacious drug delivery system. Many chemotherapeutics currently in use are poorly water soluble, which significantly complicates the search for suitable delivery systems. Combining two or three drugs in a formulation presents additional challenges in clinical practice because of compatibility and stability issues. Safer and more effective delivery of drug combinations relies on the development of biocompatible delivery systems capable of solubilizing the drug combination without using harsh surfactants or excipients. Stable and biocompatible drug formulations that improve bioavailabilty without causing toxicity are needed in the field of cancer research.

The PI3K-AKT-TOR pathway is the most deregulated pathway leading to cancer. However, drugs that target TOR have not yet been effective to treat cancer, and the PI3-AKT-TOR pathway has proven more complex than was earlier believed. Clinical trials with TOR inhibitors have failed for several cancers where inhibition of TOR resulted in the unintended activation of an oncogenic kinase called AKT.

Accordingly, what is needed is a combination drug therapy regimen that targets more than one point in the mTOR pathway. Also needed is a delivery vehicle that can solubilize efficacious drug combinations in a safe and effective manner, preferably without the use of pharmaceutical excipients that result in complications in treatment.

SUMMARY

The invention provides active agents, such as paclitaxel, docetaxel, 17-AAG, rapamycin, or etoposide, or combinations thereof, encapsulated by safe poly(ethylene glycol)-block-poly(lactic acid) ("PEG-PLA") micelles. The encapsulation of the active agents provides effective solubilization of the active agents, thereby forming drug delivery systems. A significant advantage of PEG-PLA as a carrier is that it is less toxic than Cremophor® EL or DMSO, which are used in currently known compositions in clinical trials. Additionally, PEG-PLA micelles are easier to handle than DMSO and they do not possess a foul odor, which is a problem with many current formulations currently in clinical trials. Micelle encapsulation may also reduce the occurrence of side effects (e.g., hepatotoxicity, neutropenia, neuropathy, and the like) of formulations containing active agents by maintaining the agents within the micelles until they are delivered to a target area of the body.

The invention provides compositions comprising micelles encapsulating two or three different drugs, wherein the micelles comprise poly(ethylene glycol)-block-poly(lactic acid) ("PEG-PLA") polymers. The hydrophobic poly(lactic acid) block of the polymers orient toward the interior of each micelle, and the hydrophilic poly(ethylene glycol) block of the polymers orient toward the exterior of each micelle. The molecular weight of the poly(ethylene glycol) block can be about 1,000 to about 35,000 g/mol and the molecular weight of the poly(lactic acid) block can be about 1,000 to about 15,000 g/mol. The drug loading of the micelles can be about 1 wt. % to about 50 wt. % with respect to the mass of the micelles. The two or three drugs can be, for example, any two or more of paclitaxel, docetaxel, 17-AAG, rapamycin, and etoposide. The micelle compositions that include combinations of these drugs are significantly advantageous because they are able to block the TOR pathway at two points, at the AKT and TOR levels, which enables the combination to effectively shut down the pathway when administered to a patient in need of such treatment.

The composition can be substantially free of ethanol, dimethyl sulfoxide, castor oil, and castor oil derivatives. For example, the composition can comprise less than about 2 wt. %, less than about 1 wt. %, less than about 0.5 wt. %, or less than about 0.1 wt. %, of ethanol, dimethyl sulfoxide, castor oil, and castor oil derivatives, individually or in combination.

The combined drug loading in the micelles can be about 5 wt. % to about 50 wt. %, or about 10 wt. % to about 25 wt. %. The ratio of drugs in the micelles, for two drugs, can be about 1:20 to about 20:1 or about 1:10 to about 10:1. The ratio of drugs in the micelles, for three drugs, can be about 20:1:1 to about 1:20:1 to about 1:1:20, or about 10:1:1 to about 1:10:1 to about 1:1:10, to about 1:1:1. In other words, any one of the three drugs may be provided in the composition in a wt. % amount of about ten or twenty times that of the drug present in the smallest amount. The third drug component can be provided in an amount equal to the drug present in the greatest amount, or in an amount equal to the drug present in the smallest amount, or somewhere in between, specifically including each integer within the aforementioned numerical values.

The composition can include an aqueous vehicle, wherein the concentration of the drugs is about 0.4 mg/mL to about 25 mg/mL, about 0.6 mg/mL to about 20 mg/mL, or about 1 mg/mL to about 15 mg/mL, with respect to the volume of the aqueous vehicle. The encapsulated drugs can have an aqueous solubility of about 1 mg/mL to about 10 mg/mL when contacted with an aqueous environment.

In some embodiments, the molecular weight of the poly(ethylene glycol) block can be, for example, about 1,500 to about 14,000 g/mol, and the molecular weight of the poly(lactic acid) block can be about 1,500 to about 7,000 g/mol. The molecular weight of the poly(ethylene glycol) block can also be about 10,000 to about 14,000 g/mol, and the molecular weight of the poly(lactic acid) block can be about 5,000 to about 7,000 g/mol. The average diameter of the micelles can be about 30 nm to about 50 nm, or about 32 nm to about 45 nm, or about 35 nm to about 42 nm.

The drug loading in the micelles, for each individual drug, can be about 1 wt. % to about 25 wt. %, with respect to the weight of the micelles. The drug loading of each drug can also be about 4 wt. % to about 24 wt. %, or about 5 wt. % to about 20 wt. %, or about 6 wt. % to about 15 wt. %, with respect to the weight of the micelles.

The drugs can be incorporated together into individual PEG-PLA micelles, thereby forming multiple drug micelles (MDM). Alternatively, the drugs can be incorporated individually into PEG-PLA micelles, thereby forming single drug micelles (SDM). Single drug micelles that contain different drugs can then be combined to provide a single drug micelle drug combination (SDMDC) composition, and the micelles can be combined in a single aqueous vehicle to provide a therapeutic drug delivery formulation.

The invention also provides a composition as described above, wherein the two or three drugs can be (a) rapamycin and paclitaxel; (b) rapamycin and 17-AAG; (c) paclitaxel and 17-AAG; or (d) paclitaxel, 17-AAG, and rapamycin. In various embodiments, the paclitaxel of the aforementioned combinations can be exchanged for docetaxel. In additional embodiments, the 17-AAG of the aforementioned combinations can be exchanged for geldanamycin, 17-DMAG, or other known geldanamycin derivatives (several of which are described herein), and the rapamycin can be exchanged for deforolimus, temsirolimus, everolimus, etoposide or tenipoxide. Any combination of these drug exchanges can be used in the compositions described herein. Accordingly, numerous two and three drug combinations can be prepared as micelle encapsulated drug delivery formulations. The formulations can be prepared as MDM, SDM, or SDMDC type compositions. In some embodiments, etoposide and/or another drug recited herein may be excluded from the micelle formulation.

The invention also provides a pharmaceutical composition comprising a composition as described herein, and an aqueous carrier, wherein the composition is formulated for intravenous or intraperitoneal administration. The aqueous carrier can include, for example, saline or an aqueous carbohydrate solution.

The invention further provides a method of simultaneously administering two or three drugs to a patient that has, or has been diagnosed with, a condition that can be treated by administration of at least one of rapamycin, paclitaxel, and 17-AAG, or another active agent recited herein. In another embodiment, the invention provides a method of sequentially administering two or three drugs to a patient that has, or has been diagnosed with, a condition that can be treated by administration of at least one of an active agent recited herein. For example, single drug-loaded micelles (SDM) can be prepared and combined prior to administration to a patient, or the SDM can be sequentially administered to a patient. Such sequential administration allows for synergistic anticancer activity, such as by administration of paclitaxel before 17-AAG, or for tumor priming, whereby the administration of a first dose can kill tumor cells, reduce tumor cell density, and/or allow for greater uptake of a second administered dose of SDM (or alternatively two drug MDM or SDMDC).

The methods can include administering an effective amount of a composition described herein, wherein the condition is thereby treated. In some embodiments, the condition is cancer, for example, breast cancer, colon cancer, lung cancer, ovarian cancer, pancreatic cancer, prostate cancer, or leukemia. Each drug in the micelles can be administered in an amount of, for example, about 1 mg/m$^2$ to about 1000 mg/m$^2$, about 4 mg/m$^2$ to about 4000 mg/m$^2$, about 100 mg/m$^2$ weekly to about 500 mg/m$^2$ weekly, or about 300 mg/m$^2$ weekly to about 400 mg/m$^2$ weekly.

The invention also provides a method of killing cancer cells or inhibiting the growth of cancer cells comprising contacting the cells with an effective lethal or inhibitory amount of a composition described herein. The contacting can be in vivo, or alternatively, the contacting can be in vitro. The cancer cells can be, for example, human breast cancer cells, human colon cancer cells, human lung cancer cells, human ovarian cancer cells, human pancreatic cancer cells, human prostate cancer cells, or leukemia cells. In one embodiment, the composition is administered to a patient, followed by disruption of the micelles in the blood stream, which then delivers the drugs to cancer cells to initiate the contacting.

The invention additionally provides a method of inhibiting Hsp 90 comprising contacting Hsp 90 with an effective inhibitory amount of a composition described herein. Additionally, the invention provides a method of inhibiting the mTor pathway comprising contacting mTor with an effective inhibitory amount of a composition described herein, thereby inhibiting the mTor pathway at more than one point. The contacting can be in vivo, or alternatively, the contacting can be in vitro.

The invention additionally provides a method of increasing the half-life of a drug in the blood of a mammal comprising administration of a composition as described herein to the blood of a mammal, wherein the half-life of the drug is increased in comparison to the half-life of the drug in the blood after administration of the drug with a carrier that does not comprise micelles as described herein.

The invention further provides a composition for the delayed release of rapamycin, paclitaxel, 17-AAG, or other drug recited herein, comprising a composition as described herein, wherein less than about 20 wt. % of the drugs, less than about 40 wt. % of the drugs, less than about 50 wt. % of the drugs, less than about 60 wt. % of the drugs, less than about 70 wt. % of the drugs, less than about 75 wt. % of the drugs, less than about 80 wt. % of the drugs, or less than about 90 wt. % of the drugs, are released from the micelles after exposure to an aqueous environment or to the body fluid of a mammal for 30 minutes, 1 hour, or alternatively, 2 hours.

The invention also provides for the use of the compositions described herein for use in medical therapy. The medical therapy can be treating cancer, for example, brain tumors, breast cancer, colon cancer, head and neck cancer, lung cancer, lymphoma, melanoma, neuroblastoma, ovarian cancer, pancreatic cancer, prostate cancer, or leukemia. The invention also provided for the use of a composition as described herein for the manufacture of a medicament to treat such cancers. The medicament can include a pharmaceutically acceptable diluent, excipient, or carrier. The invention further provides for the use of a composition as described herein to prepare a medicament for treating cancer in a mammal, such as a human.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention, however, one skilled in the art will understand that portions of the example or aspect may be used in combination with other examples or aspects of the invention.

17-AAG, (C) MDM with ETO/17-AAG, (D) MDM with DCTX/17-AAG; and (E) MDM with PTX/ETO/17-AAG; from PEG-b-PLA micelles (12.5 mM PBS, pH=7.4, 37° C.; (n=4, Mean±SD).

Figure 4:
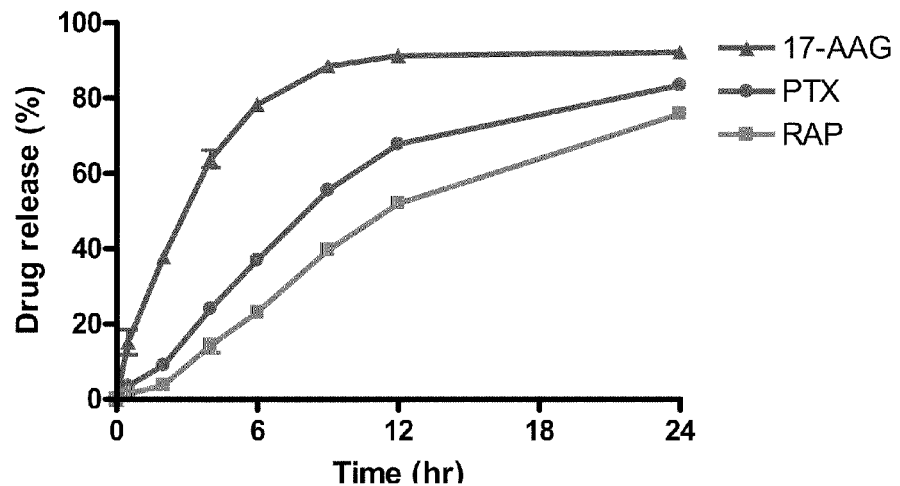

FIG. 4 illustrates in vitro release profiles of the 3-drug combination paclitaxel, rapamycin, and 17-AAG (PTX/RAP/17-AAG), solubilized by PEG-b-PLA micelles (12.5 mM PBS, pH=7.4, 37° C.; n=4, Mean±SD).

Figure 5:
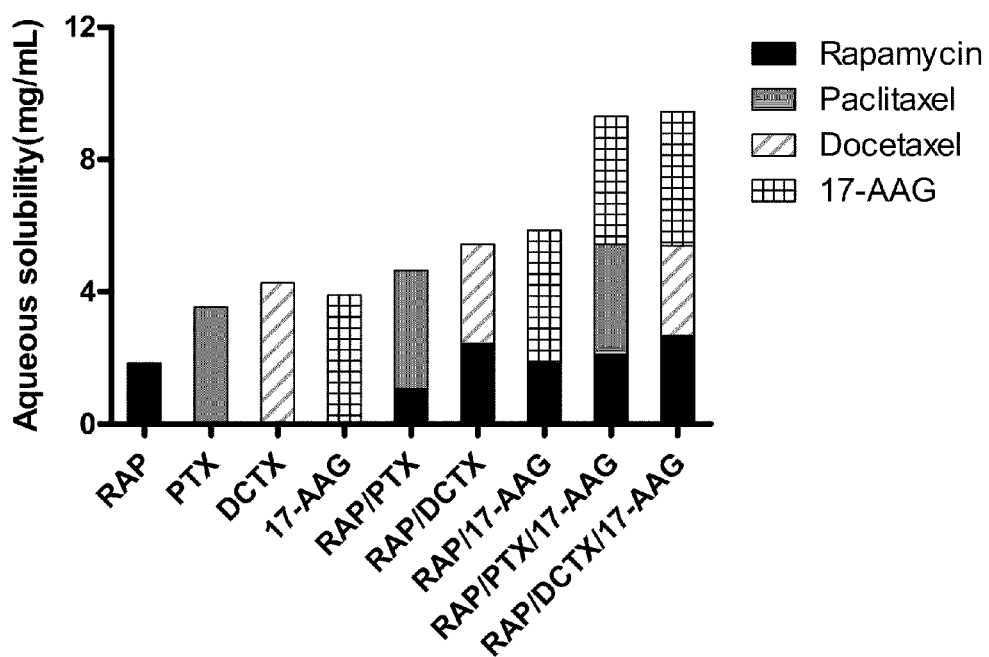

FIG. 5 illustrates data from the solubilization of paclitaxel, docetaxel, rapamycin, 17-AAG, and 2- or 3-combinations (chemo+17-AAG) by PEG-b-PLA micelles (4.2K:1.9K) in water; n=3, Mean.

Figure 6:
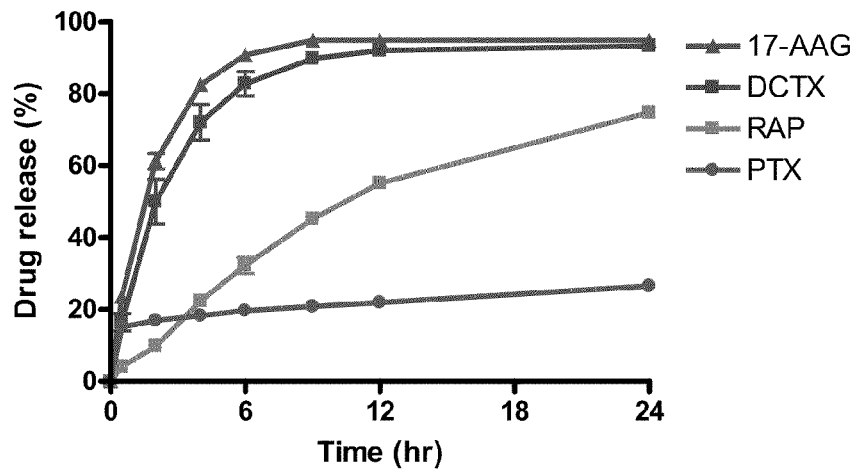

FIG. 6 illustrates data from the in vitro release of paclitaxel, docetaxel, rapamcyin or 17-AAG from PEG-b-PLA micelles (12.5 mM PBS, pH=7.4, 37° C.; n=4, Mean±SD).

Figure 7:
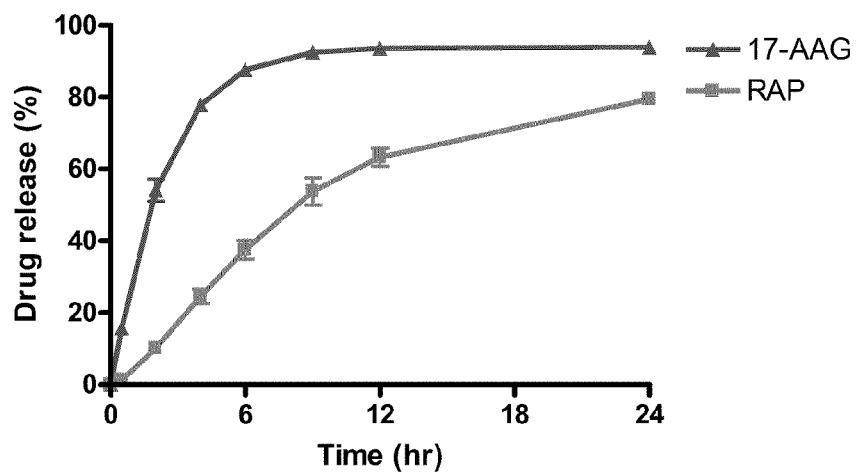

FIG. 7 illustrates data from the in vitro combination release of rapamycin and 17-AAG from PEG-b-PLA micelles (12.5 mM PBS, pH=7.4, 37° C.; (n=4, Mean±SD).

Figure 8:
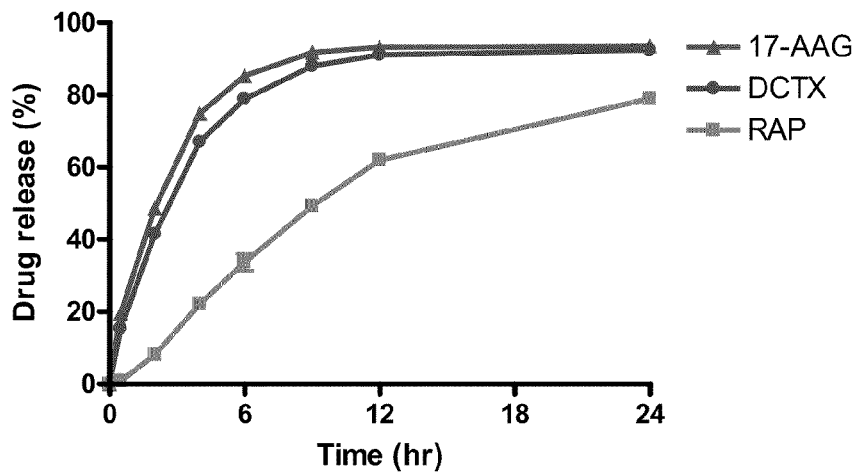

FIG. 8 illustrates data from the in vitro combination release of rapamycin, docetaxel & 17-AAG from PEG-b-PLA micelles (12.5 mM PBS, pH=7.4, 37° C.); (n=4, Mean±SD).

Figure 9:
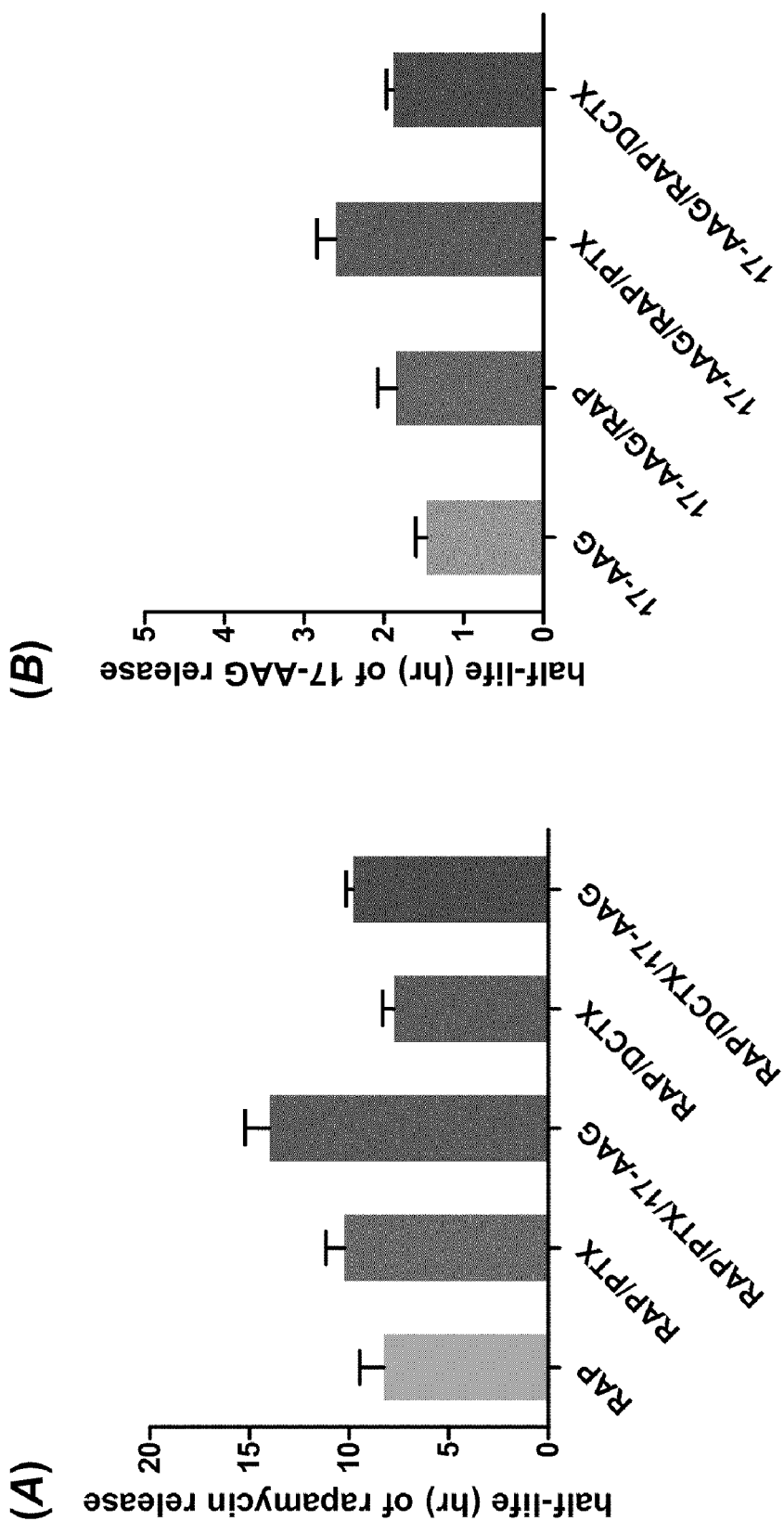

FIG. 9 illustrates half life parameters (A) for in vitro rapamycin release; and (B) for in vitro 17-AAG release, from PEG-b-PLA micelles (single agent, 2- or 3-drug combinations).

Figure 10:
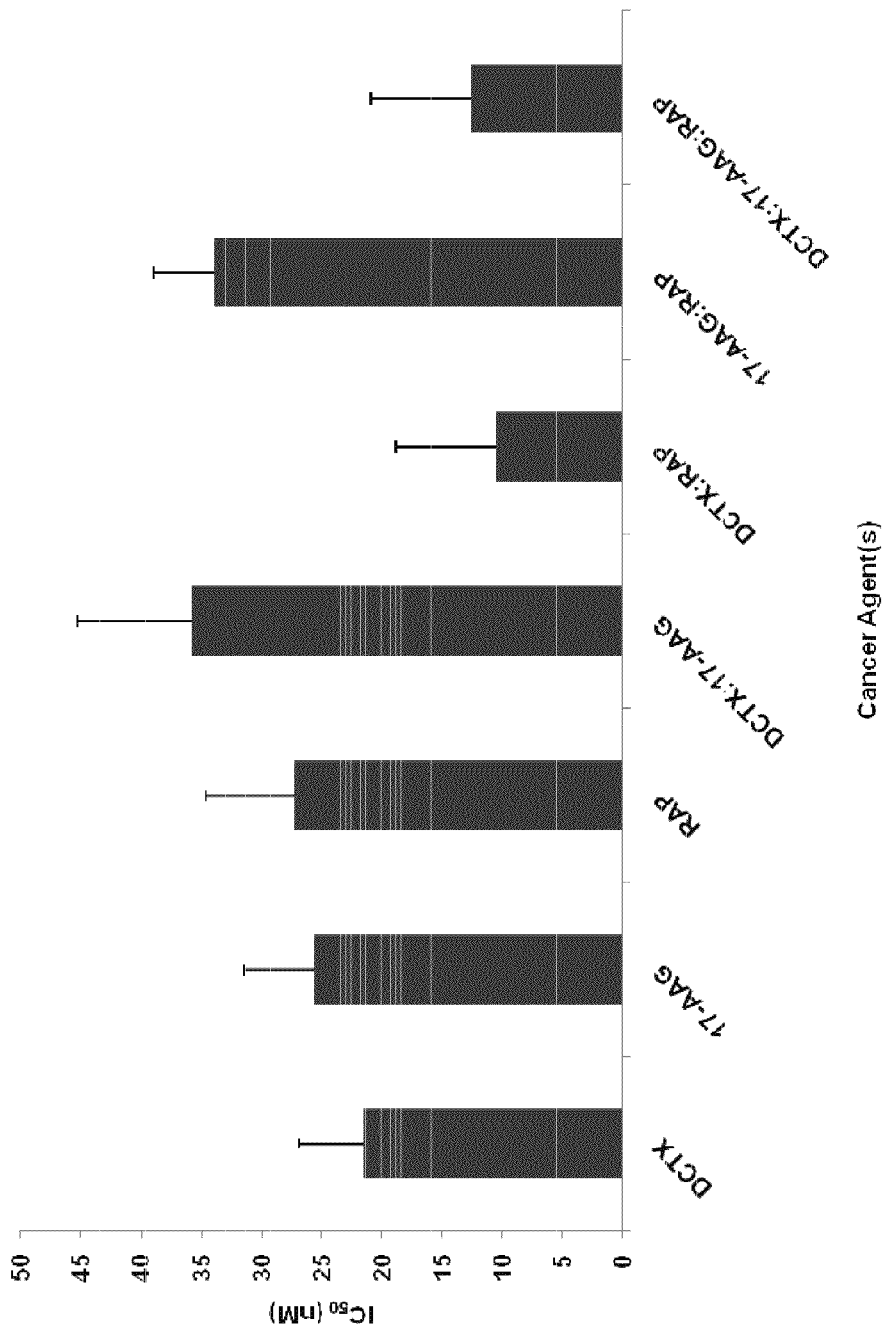

FIG. 10 illustrates in vitro free drug cytotoxicity results of rapamycin, docetaxel, 17-AAG, and various combinations thereof, against the MCF-7 breast cancer cell line using a resazurin assay.

Figure 11:
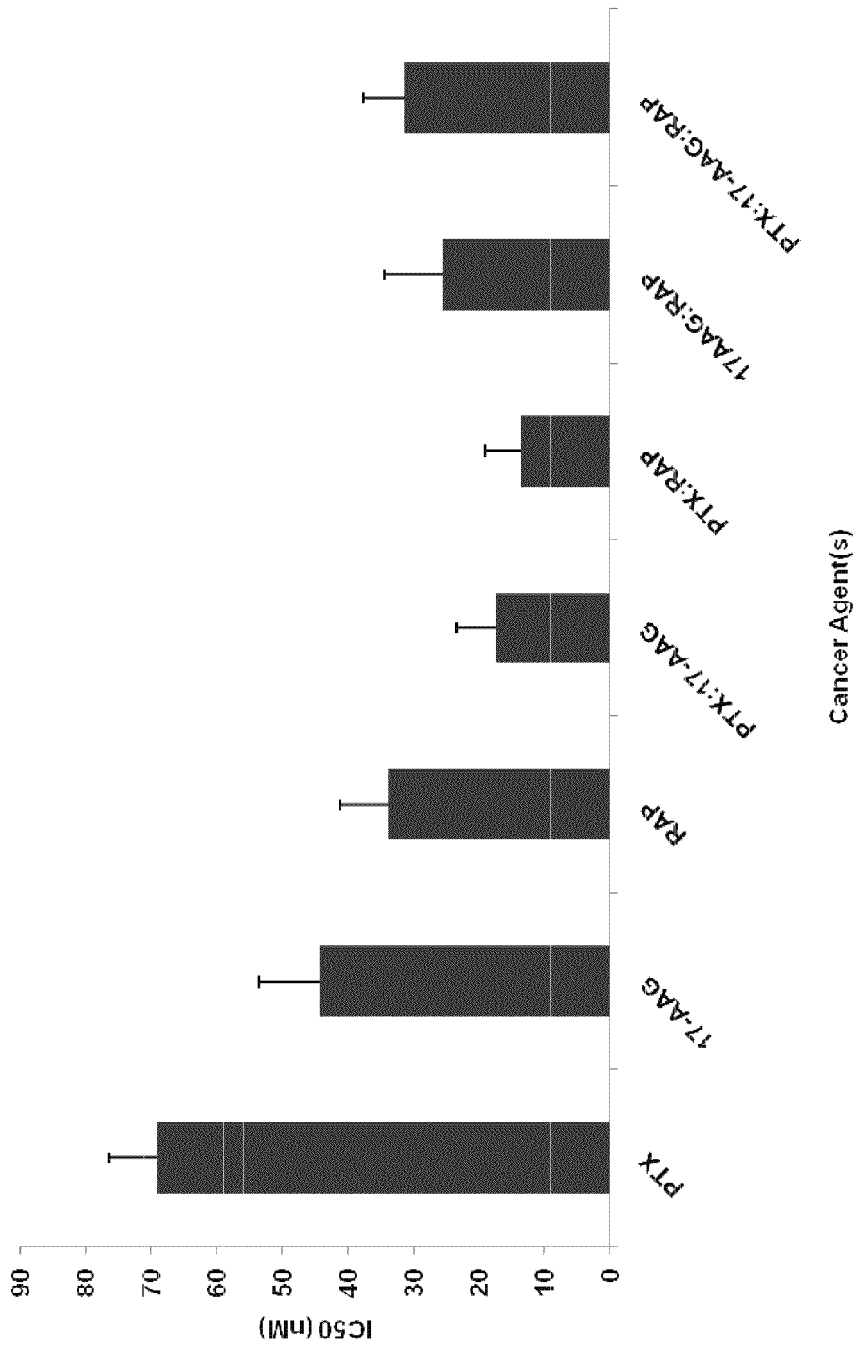

FIG. 11 illustrates in vitro free drug cytotoxicity results of rapamycin, paclitaxel, 17-AAG, and various combinations thereof, against the SKOV-3 ovarian cancer cell line using a resazurin assay.

Figure 12:
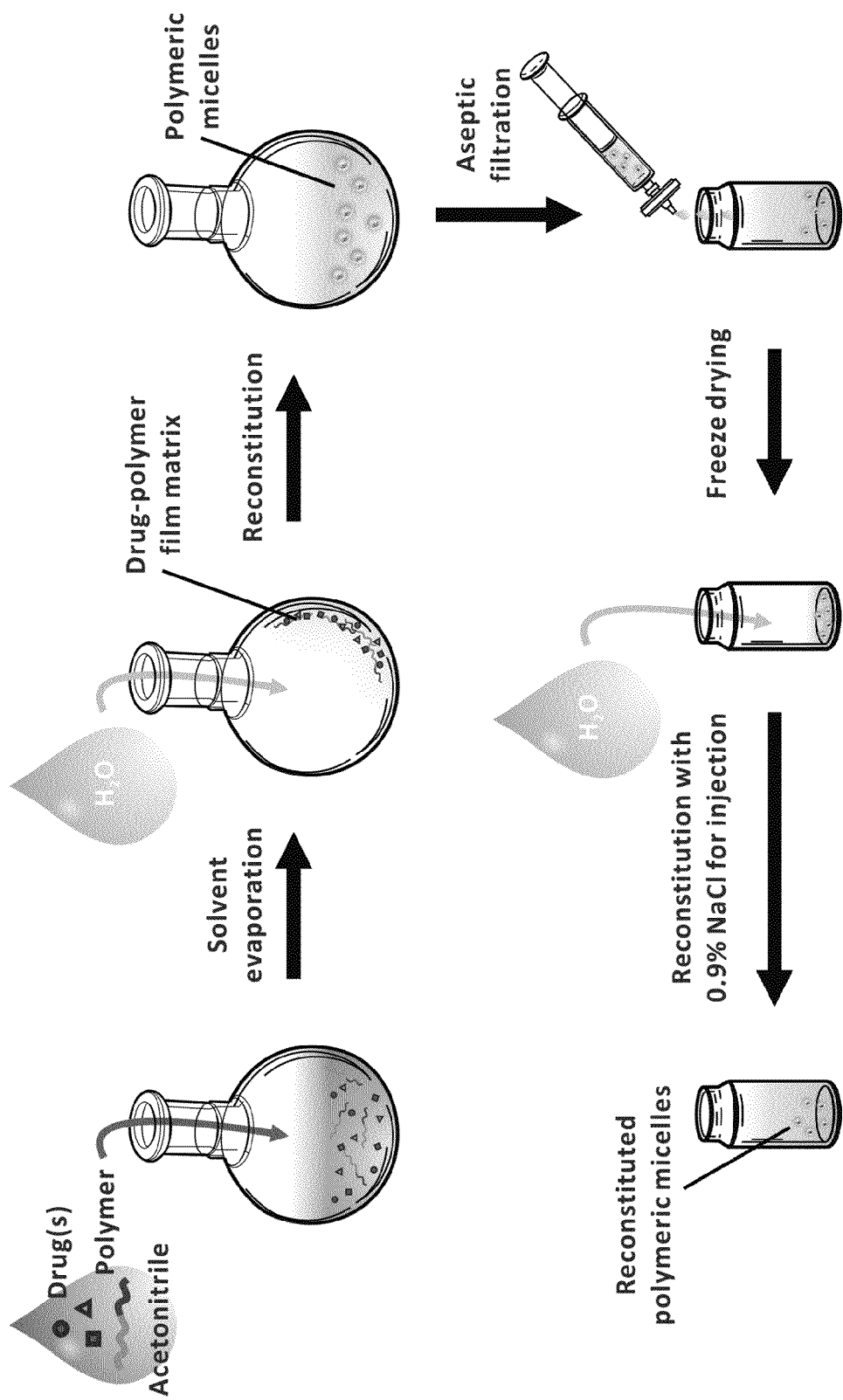

FIG. 12 illustrates a schematic representation of a method for preparing micelles and solubilizing hydrophobic drugs, according to an embodiment of the disclosure.

Figure 13:
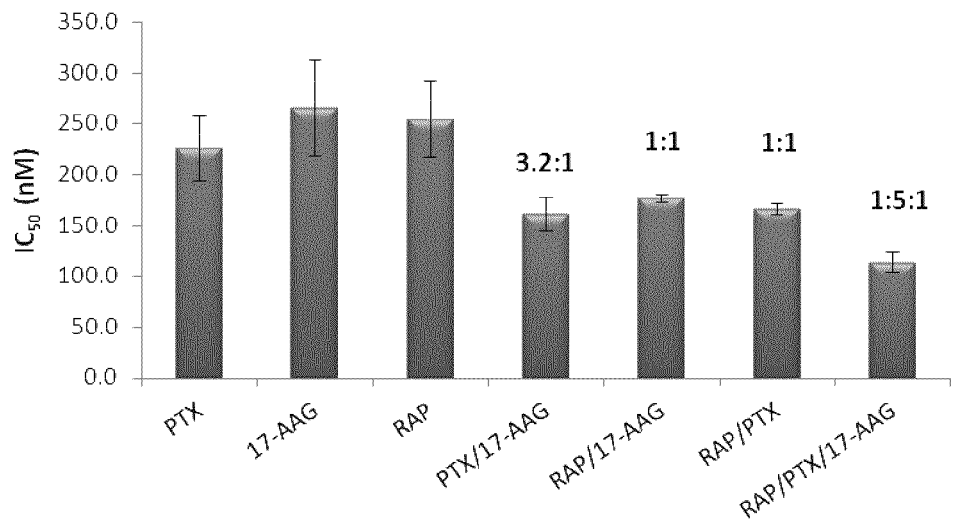

FIG. 13 illustrates $IC_{50}$ data for MCF-7 breast cancer cells, according to an embodiment.

Figure 14:
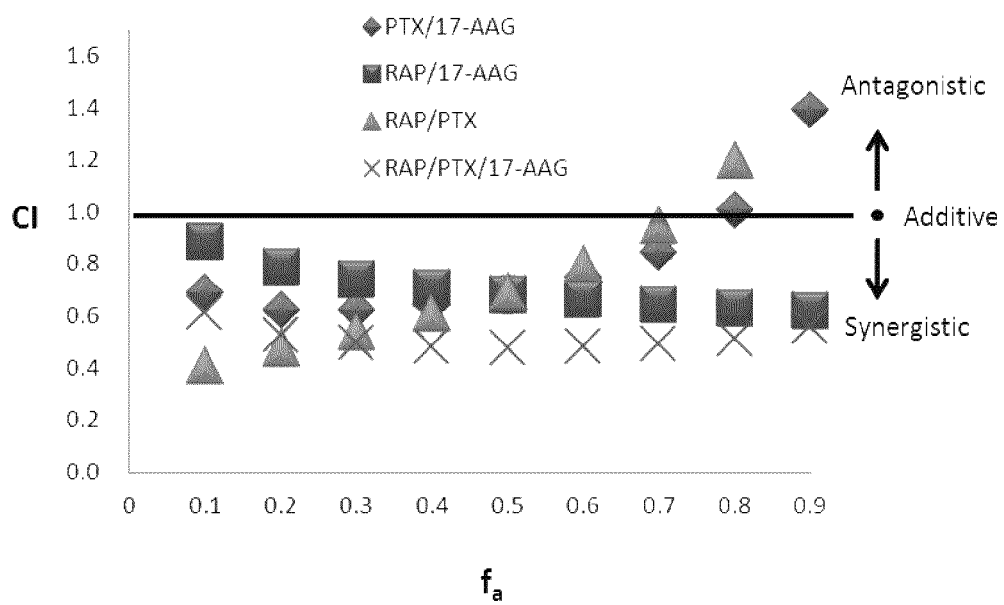

FIG. 14 illustrates combination index (CI) of 2- or 3-drug combinations of FIG. 13 calculated based on Chou and Talalay method.

Figure 15:
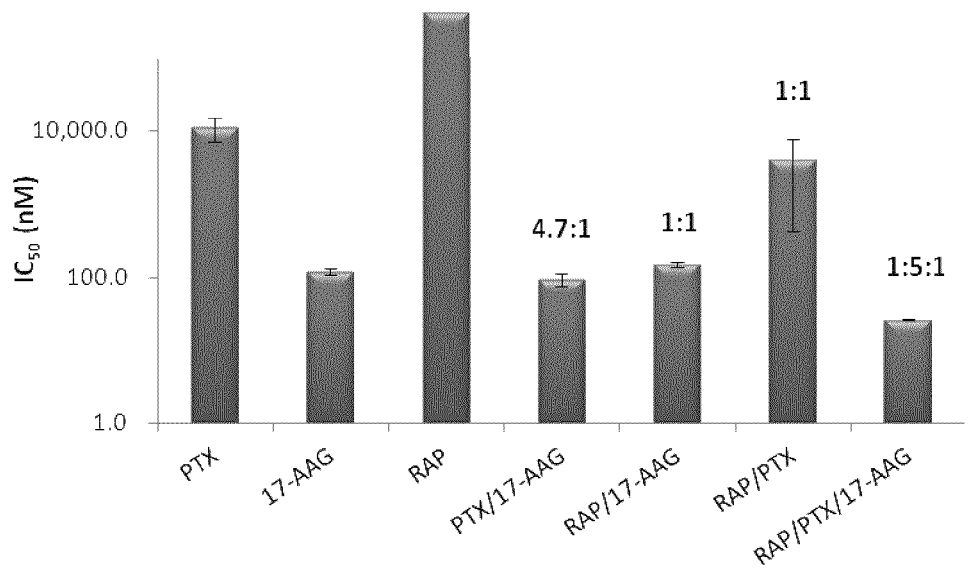

FIG. 15 illustrates $IC_{50}$ data for 4T1 breast cancer cells, according to an embodiment.

Figure 16:
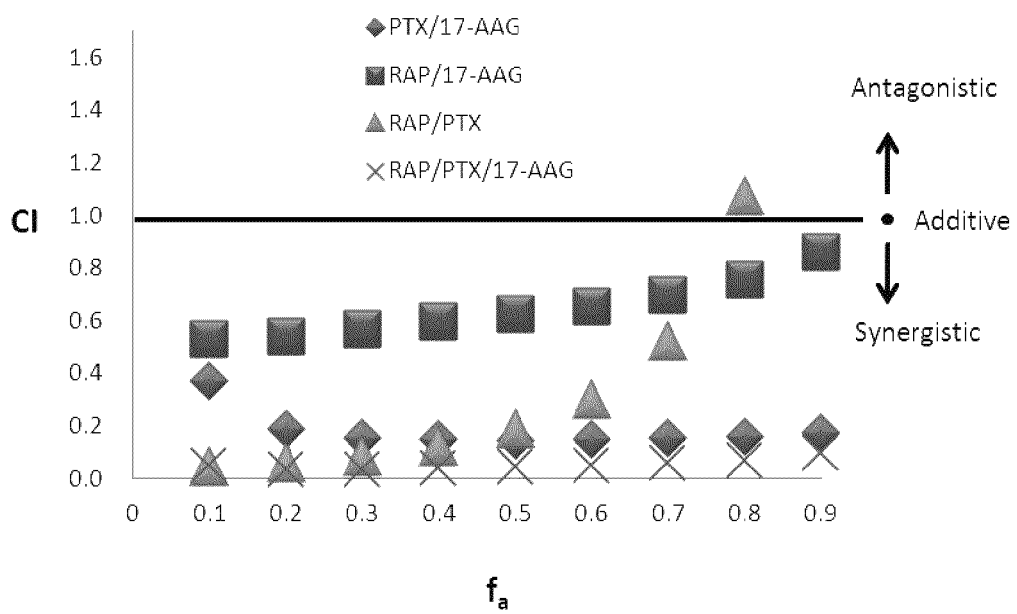

FIG. 16 illustrates combination index (CI) of 2- or 3-drug combinations of FIG. 15 calculated based on Chou and Talalay method.

Figure 17:
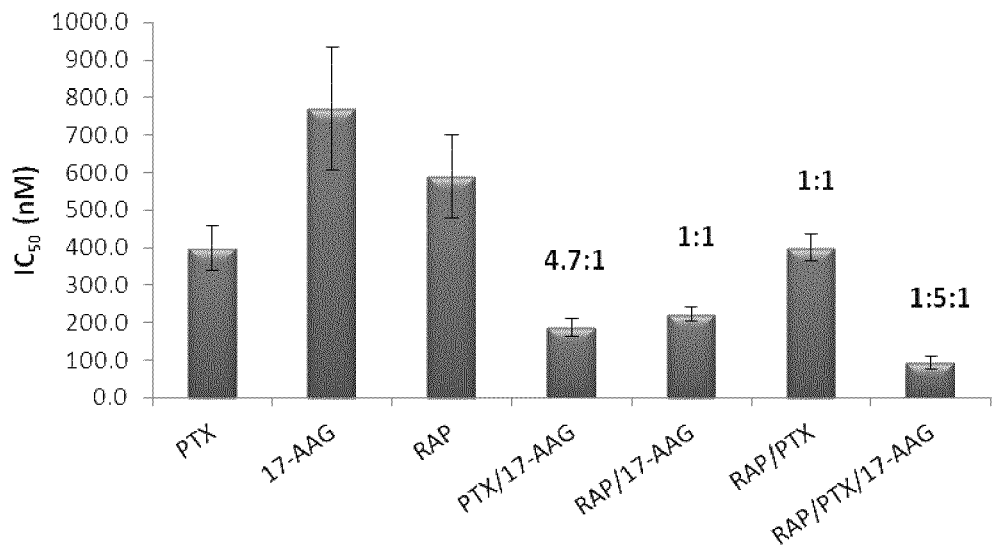

FIG. 17 illustrates $IC_{50}$ data for A549 non-small cell lung cancer cells, according to an embodiment.

Figure 18:
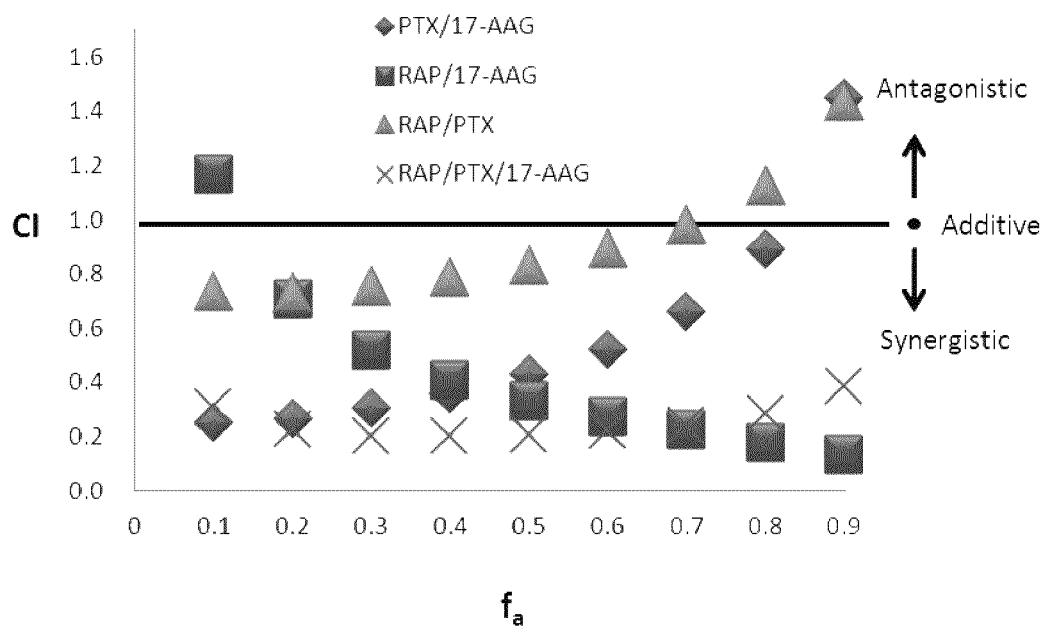

FIG. 18 illustrates combination index (CI) of 2- or 3-drug combinations of FIG. 17 calculated based on Chou and Talalay method.

Figure 19:
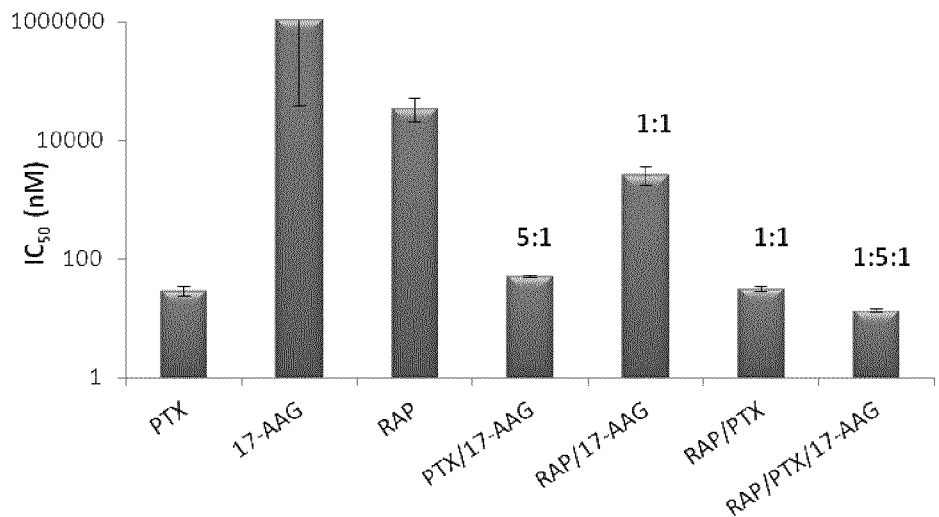

FIG. 19 illustrates $IC_{50}$ data for LS180 colon cancer cells, according to an embodiment.

Figure 20:
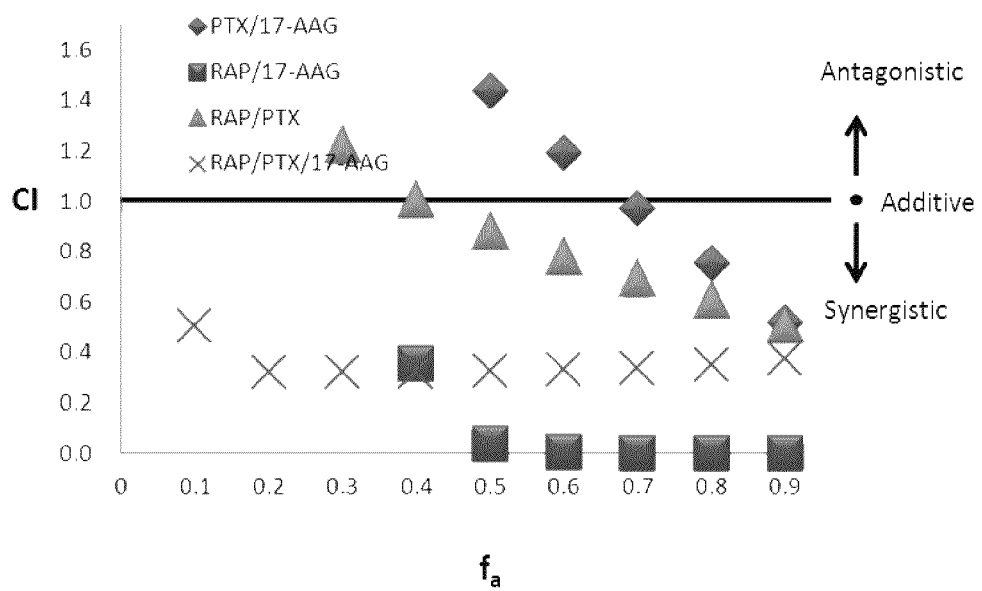

FIG. 20 illustrates combination index (CI) of 2- or 3-drug combinations of FIG. 19 calculated based on Chou and Talalay method.

Figure 21:
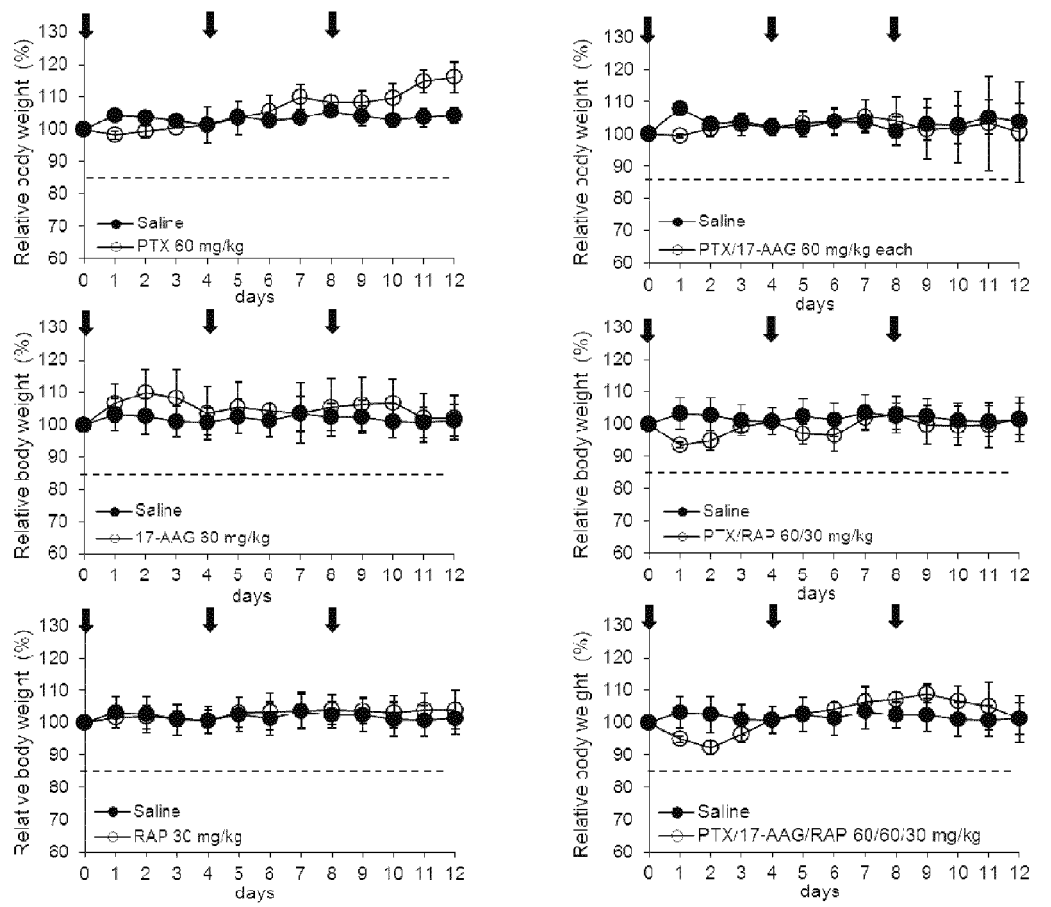

FIG. 21 illustrates the results of acute toxicity experiments (FVB female albino mice).

Figure 22:
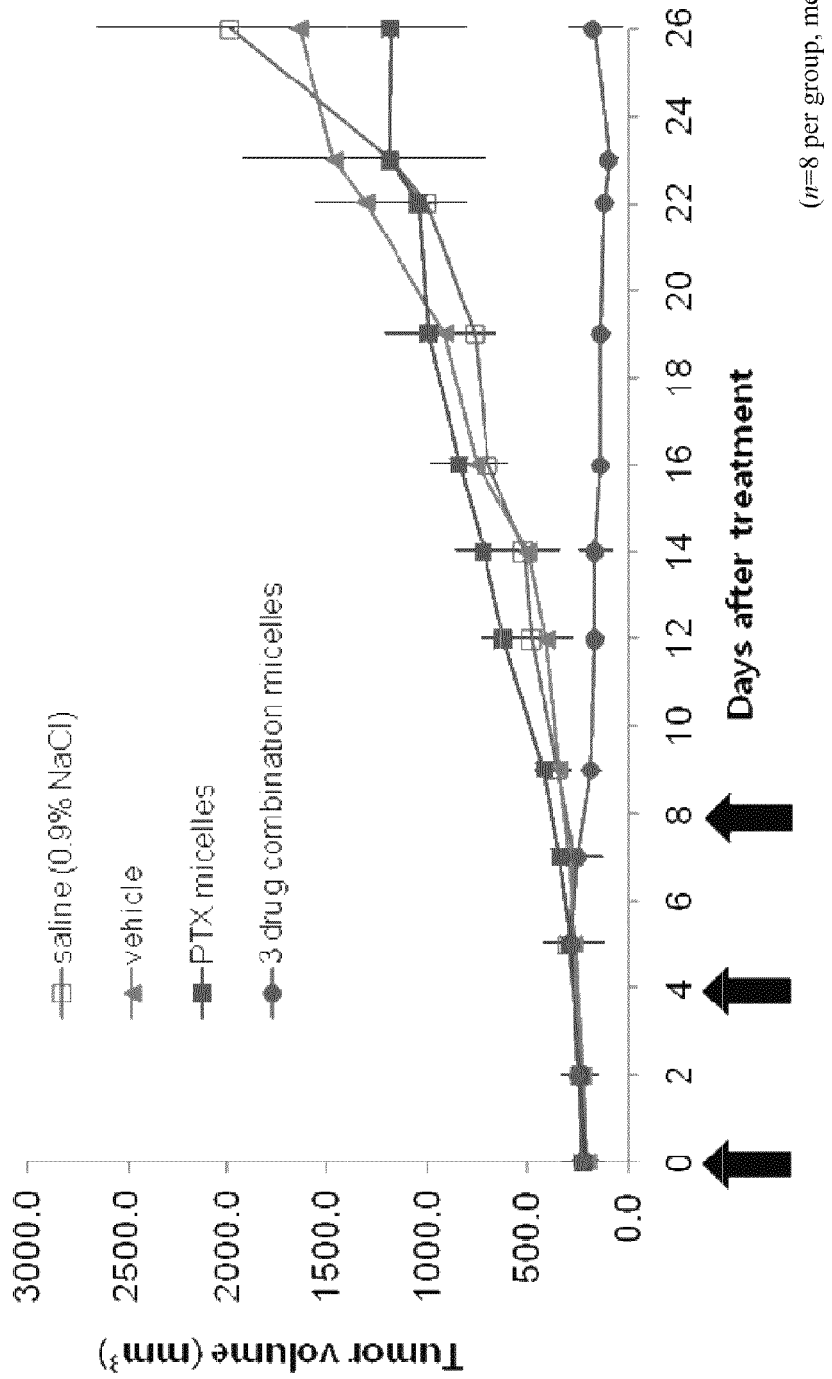

FIG. 22 illustrates the anti-tumor efficacy of a 3 drug combination of paclitaxel, 17-AAG, and rapamycin (60:60:30 mg/kg) vs. PTX single drug loaded micelles (60 mg/kg), in an A549 murine tumor model, with saline and a micelle vehicle alone used as controls.

Figure 23:
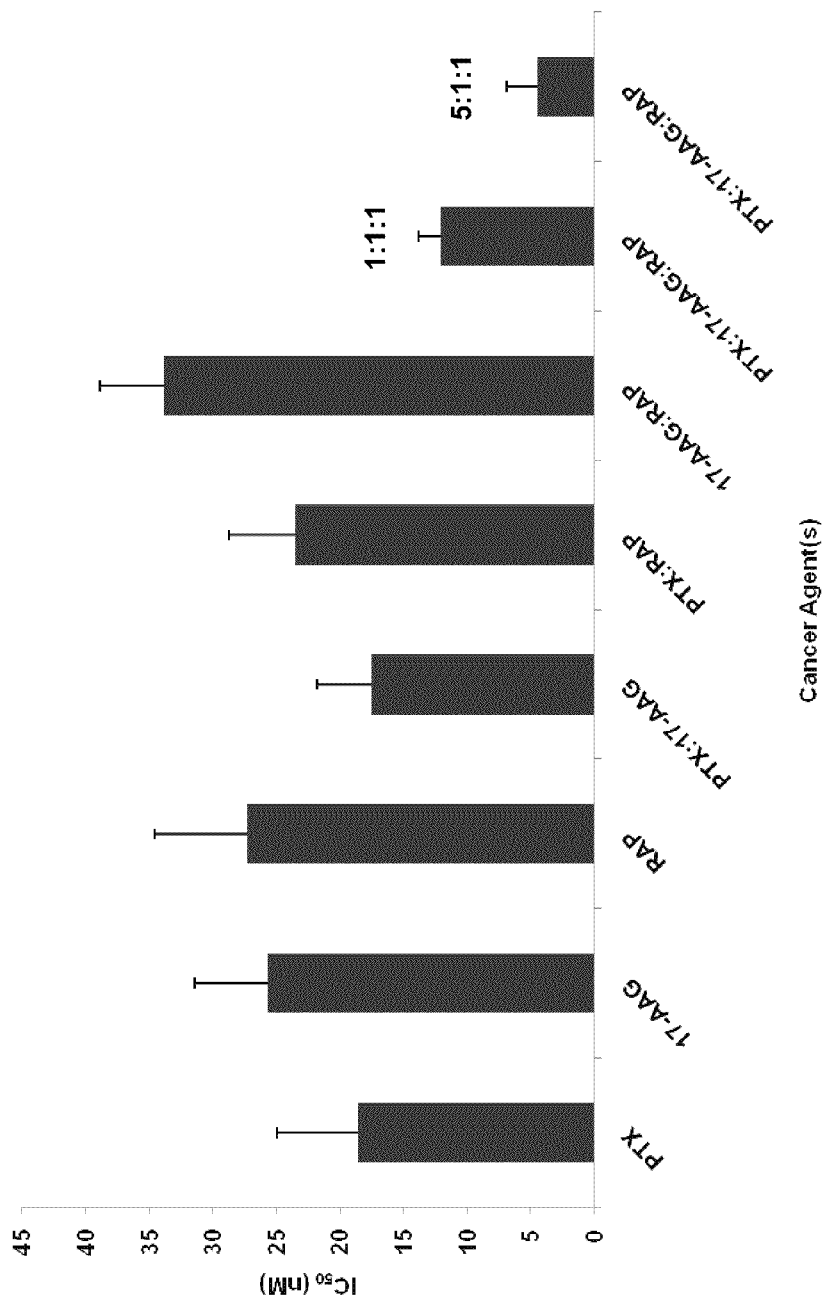

FIG. 23 illustrates in vitro free drug cytotoxicity results of rapamycin, paclitaxel, 17-AAG, and various combinations thereof, against the MCF-7 breast cancer cell line using resazurin assay.

DETAILED DESCRIPTION

Heat Shock Protein 90 (Hsp90) is an important target for cancer therapy due to its key role in regulating proteins that are involved in tumor cell proliferation. It was discovered that geldanamycin, a benzoquinone ansamycin antibiotic, can strongly bind to the ATP/ADP binding pocket of Hsp90, interfering with the survival and growth of a diverse family of tumors. Geldanamycin is a promising new anticancer agent, but its clinical development has been hampered by severe hepatotoxicity and poor solubility. Two analogues, 17-allylamino-17-demethoxygeldanamycin (17-AAG; tanespimycin) and 17-dimethylamino-ethylamino-17-demethoxygeldanamycin (17-DMAG), were developed to help alleviate some of these issues.

Several promising leads for clinical translation have been directed to development of 17-DMAG as the more pharmaceutically practical formulation because 17-DMAG possesses superior aqueous solubility and greater oral bioavailability compared to 17-AAG. However, despite its apparent advantages over 17-AAG, 17-DMAG is characterized by a large volume of distribution when administered to animals. This wide distribution could lead to undesired toxicity because the maximum tolerated dose of 17-DMAG is significantly less than that of 17-AAG (8 mg/m$^2$/day and 100-200 mg/m$^2$/day in dogs, respectively).

The major obstacle for delivery of 17-AAG is its limited aqueous solubility (about 0.1 mg/mL). This limited solubility has resulted in the use of complicated formulations with excipients such as Cremophor® EL (CrEL), DMSO, and/or ethanol before parenteral administration. This is undesirable from a patient tolerability standpoint because CrEL is known to induce hypersensitivity reactions and anaphylaxis, and requires patient treatment with antihistamines and steroids before administration. Accordingly, safer and more effective delivery of 17-AAG relies on the development of biocompatible delivery systems capable of solubilizing the drug without the use of harsh surfactants.

Combination drug therapy is becoming an important method in the treatment of cancer. Researchers are interested in the combination of chemotherapy and signal transduction inhibitors, as well as the combination of different signal transduction inhibitors. In murine tumor models and in early clinical trials, paclitaxel (chemotherapy) has been shown to act synergistically with rapamycin, a signal transduction inhibitor. In such models, paclitaxel also acts synergistically with 17-AAG, another signal transduction inhibitor. Additionally, rapamycin and 17-AAG can act in a synergistic manner for breast cancer cells, presumably due to inhibition of mTOR by rapamycin and inhibition of AKT by 17-AAG. This central mechanism of dual drug action is of interest because of clinical experience with rapamycin and its analogues for the treatment of cancer, where AKT activation by a feedback mechanism appears to be a major cause of treatment failure in mTOR inhibition.

Each of paclitaxel, rapamycin, and 17-AAG are poorly water-soluble, requiring specialized vehicles for drug solubilization, administration, and delivery. The polymeric micelles described herein, prepared from the biocompatible poly(ethyleneglycol)-block-poly(lactic acid) (PEG-b-PLA) can dramatically increase the water solubility of paclitaxel, rapamycin, and 17-AAG together in the same nano-sized aqueous vehicle (e.g., a PEG-b-PLA micelle). This nano-formulation offers a new approach for the delivery of a triple drug combination of paclitaxel, rapamycin, and 17-AAG for the treatment of cancer.

Preparation of the formulations can be carried out on a large scale. The formulation provides ease of sterilization due to the small size (~40 nm) of the micelles, ease of drug administration as an aqueous vehicle, low toxicity due to the proven safety of PEG-block-poly(lactic acid), avoidance of noxious vehicles that are required in the clinic for the individual drugs, and unprecedented synergistic anti-tumor efficacy, realized for the first time for a three-drug combination, e.g., paclitaxel, 17-AAG and rapamycin.

Accordingly, one, two, and three drug combination formulation of rapamycin, paclitaxel and 17-AAG are disclosed herein, wherein the drugs are encapsulated within micelles, and the micelles can be administered concurrently or sequentially. In some embodiments, all three drugs can be loaded at substantially the same level in combination with micelles in the same manner as they can be loaded in a single drug micelle formulation. These micelles were stable and remained soluble for more than 24 hours at room temperature (~23° C.), and they showed suitable cytotoxicity against cancer cell lines, such as the MCF-7 a breast cancer cell line and the SKOV-3 ovarian cancer cell line.

Definitions

As used herein, certain terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", "an example embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect such aspect, feature, structure, moiety, or characteristic in connection with other embodiments, whether or not explicitly described.

The term "and/or" means any one of the items, any combination of the items, or all of the items with which this term is associated.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for use of such exclusive terminology as "solely," "only," and the like in connection with the recitation of claim elements, or use of a "negative" limitation.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer. Unless indicated otherwise herein, the term "about" is intended to include values, e.g., weight percents, proximate to the recited range that are equivalent in terms of the functionality of the individual ingredient, the composition, or the embodiment. In addition, unless indicated otherwise herein, a recited range (e.g., weight percents or carbon groups) includes each specific value, integer, decimal, or identity within the range.

The phrase "one or more" is readily understood by one of skill in the art, particularly when read in context of its usage. For example, one or more substituents on a phenyl ring refers to one to five, or one to up to four, for example if the phenyl ring is disubstituted.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

Provisos may apply to any of the disclosed categories or embodiments wherein any one or more of the other above disclosed embodiments or species may be excluded from certain categories, compositions, or embodiments.

Active Agents/Drugs for Polymeric Micelles.

Rapamycin, also known as sirolimus, is an immunosuppressant drug and a known mTor inhibitor. The mTOR complex 1 (mTORC1) drives cellular growth by controlling various processes that control protein synthesis and angiogenesis. Upstream signaling pathways of mTORC1 include the phosphatidylinositol 3-kinase (PI3K/Akt) pathway, which is frequently dysregulated in many cancers. For example, 60-70% of lung cancers have PI3K/Akt/mTORC1 pathway activation Inhibition of mTORC1 represents a very attractive anti-tumor target, either as a mono-therapy or in combination with chemo-therapy or other strategies targeting other pathways.

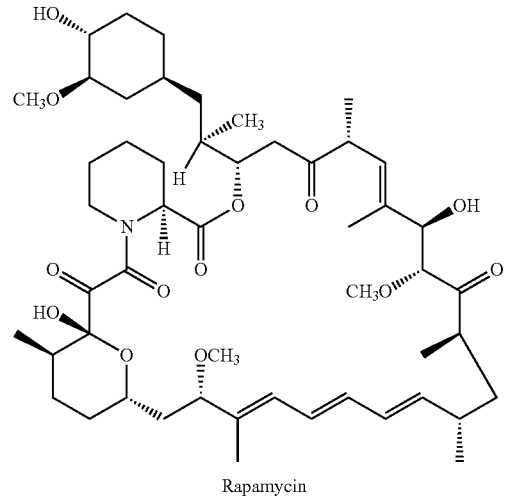

Rapamycin

Rapamycin derivatives that may be exchanged with rapamycin in the formulations herein include deforolimus, temsirolimus, everolimus, and CCI-779.

Paclitaxel is a known chemotherapeutic agent, the structure of which is illustrated below.

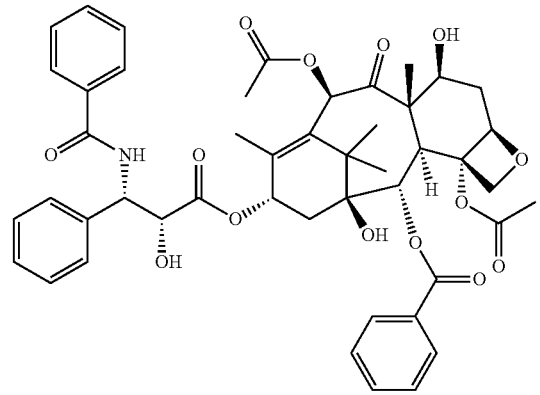

Paclitaxel

Paclitaxel derivatives that may be exchanged with paclitaxel in the formulations herein include docetaxel and other known paclitaxel derivatives.

Geldanamycin is a well-known natural product, obtainable by culturing the producing organism, *Streptomyces hygroscopicus* var. *geldanus* NRRL 3602. The compound 17-AAG is made semi-synthetically from geldanamycin, by reaction of geldanamycin with allylamine, as described in U.S. Pat. No. 4,261,989 (Sasaki et al.), the disclosure of which is incorporated herein by reference.

Geldanamycin binds strongly to the ATP/ADP binding pocket of Hsp90, thus interfering with the survival and proliferation of a diverse family of tumors, including HER-2/erbB-2 overexpressing, paclitaxel resistant breast cancers. Clinical development of geldanamycin has been hampered by its poor solubility and severe hepatotoxicity (Ge et al., *J. Med. Chem.* 49(15) (2006) 4606-4615). Thus, a significant obstacle in the preparation of pharmaceutical formulations containing geldanamycin, or its derivatives such 17-allylamino-17-demethoxy-geldanamycin (17-AAG, below), is the very poor water solubility of these lipophilic drugs.

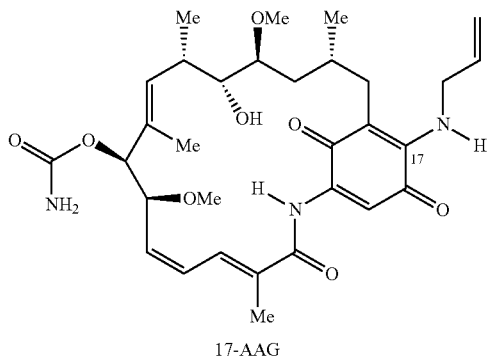

17-AAG

Suitable water solubility is of particular importance for parenteral administration. The water solubility of 17-AAG is only about 0.1 mg/mL at neutral pH, making it difficult to administer in a safe and effective manner. Attempts have been made to address the solubility issue but each formulation was accompanied by its own drawbacks, such as the use of DMSO, ethanol, or various undesirable surfactants.

The compound 17-AAG (17-allylamino-17-demethoxygeldanamycin, or tanespimycin) is a promising heat shock protein 90 inhibitor currently undergoing clinical trials for the treatment of cancer. Despite its selective mechanism of action on cancer cells, 17-AAG faces challenging issues due to its poor aqueous solubility. Current 17-AAG compositions require formulation with Cremophor® EL (CrEL), DMSO, and/or ethanol. See U.S. Application Publication No. 2005/0256097 (Zhong et al.).

Cremophor® EL is a castor oil derivative, typically prepared by reacting 35 moles of ethylene oxide with each mole of castor oil to provide a polyethoxylated castor oil (CAS number 61791-12-6). The use of Cremophor® EL (e.g. KOS-953) or DMSO for parenteral formulations is undesirable from a patient tolerability standpoint due to its potential side effects. Various adverse effects can include acute hypersensitivity reactions, peripheral neurotoxicity, hyperlipidaemia, and/or inhibition of P-glycoprotein. Furthermore, 17-AAG has a high volume of distribution (Vd) and considerable systemic toxicity at low doses (less than 20 mg/kg). Accordingly, improved formulations are needed to safely administer anticancer drugs, such as the combination of 17-AAG, paclitaxel, and rapamycin, to patients in need of such treatment.

The disclosure herein provides a CrEL-free single, dual and triple drug formulations, prepared using amphiphilic diblock micelles composed of poly(ethylene oxide)-b-poly(D, L-lactic acid) (PEG-b-PLA). Dynamic light scattering (DLS) revealed PEG-PLA (12:6 kDa) micelles with average diameters of about 257 nm in some embodiments, with critical micelle concentration of about 350 nM. The micelles can solubilize significant quantities of certain active agents, for example, about 1.5 mg/mL of 17-AAG. The area under the curve (AUC) of PEG-PLA micelles was 1.3-fold that of the standard formulation. Renal clearance ($CL_{renal}$) increased and hepatic clearance ($CL_{hepatic}$) decreased with use of the micelle formulation, as compared to the standard vehicle that employs CrEL. Accordingly, the micelle formulations described herein provide delivery vehicles for one-, two- and three-drug formulations that have several advantages over currently known compositions.

Polymers Used for Micelle Preparation.

The terms PEG-PLA or PEG-b-PLA refers to poly(ethylene oxide)-block-poly(lactic acid). The poly(lactic acid) block can include (D-lactic acid), (L-lactic acid), (D,L-lactic acid), or combinations thereof. Various forms of PEG-PLA are available commercially, such as from Polymer Source, Inc., Montreal, Quebec, or they can be prepared according to methods well known to those of skill in the art. The molecular weight of the poly(ethylene glycol) block can be about 1,000 to about 35,000 g/mol, or any increment of about 500 g/mol within said range. Suitable blocks of the poly(lactic acid) can have molecular weights of about 1,000 to about 15,000 g/mol, or any increment of about 500 g/mol within said range. The PEG block can terminate in an alkyl group, such as a methyl group (e.g., a methoxy ether) or any suitable protecting, capping, or blocking group.

The micelles of this disclosure can be prepared using PEG-PLA polymers of a variety of block sizes (e.g., a block size within a range described above) and in a variety of ratios (e.g., PEG:PLA of about 1:10 to about 10:1, or any integer ratio within said range). For example, molecular weights ($M_a$) of the PEG-PLA polymers can include, but are not limited to, 2K-2K, 3K-5K, 5K-3K, 5K-6K, 6K-5K, 6K-6K, 8K-4K, 4K-8K, 12K-3K, 3K-12K, 12K-6K, and/or 6K-12K (PEG-PLA, respectively). The drug-to-polymer ratio can also be about 1:20 to about 10:1, or any integer ratio within said range. Specific examples of suitable drug-polymer ratios include, but are not limited to, about 1:2.5; about 1:5; about 1:7.5; and/or about 1:10.

One suitable polymer is a PEG-PLA that includes blocks of about 1-3 kDa (e.g., about 2K Daltons) at an approximate 50:50 ratio. Use of this procedure resulted in unexpectedly high levels of drug loading in the micelles. For example, when Preparatory Procedure B (described below) was employed, drug loading of about 5 mg/mL of 17-AAG was achieved (about 9 mM; about 17 wt. %). Further specific examples of PEG-PLA molecular weights include 4.2K-b-1.9K; 5K-b-10K; 12K-b-6K; 2K-b-1.8K, and those described in the Examples below. Other suitable amphiphilic block copolymers that may be used are described in U.S. Pat. Nos. 4,745,160 (Churchill et al.) and 6,322,805 (Kim et al.).

Methods of Preparing PEG-PLA Micelles.

Polymer Selection. While many amphiphilic block copolymers form micelles and can encapsulate certain types of cargo, there is currently no standard for determining which polymers are best suited for encapsulating various types of materials. These determinations must still be made empirically. Several polymers that form micelles with drugs were surveyed for solubilizing a paclitaxel-rapamycin-17-AAG drug combination. The combination proved difficult to solubilize without a correct set of micellar properties. For example, the PEG-PPG-PEG triblock polymer Poloxamer F68 is useful to solubilize many hydrophobic compounds such as resveratrol, a hydrophobic organic compound with reported anticancer activity. Poloxamer F68, however, was unable to solubilize either of 17-AAG or the paclitaxel-rapamycin-17-AAG drug combination because stable micelles did not form in aqueous solutions.

Conversely, PEG-b-PLA does not form stable micelles when combined with resveratrol, but does form very stable micelles with both 17-AAG and the paclitaxel-rapamycin-17-AAG drug combination. The tri-drug loaded PEG-b-PLA micelles also display remarkable properties by solubilizing the drugs in a nearly additive fashion. Thus suitable polymers for solubilizing each drug and drug combination must be determined empirically because no reliable predictive trends exist at this time.

Micelle Preparation. Amphiphilic single chains of amphiphilic polymers present in a solvent in an amount above the critical micelle concentration (CMC) aggregate into a micelle, a core-coronal structure with a hydrophobic interior, and hydrophilic exterior or shell. Proton NMR spectroscopic studies of drug loaded PEG-b-PLA micelles indicate that while the micelles readily form in aqueous environments, they decompose in organic solvents such as DMSO. These studies also demonstrate that the drug is located at the core of the micelle and not near the corona.

PEG-b-PLA micelles can be prepared as described below in this section, as well as below in the Examples. For example, Preparatory Procedure B provides one specific method for preparing a paclitaxel, rapamycin, and 17-AAG micelle formulation. This procedure is merely illustrative for one embodiment. It can be varied according to the desired scale of preparation, as would be readily recognized by one skilled in the art. One advantage of Preparatory Procedures A and B is that they do not require dialysis of a micelle solution, as in Procedure C.

Preparatory Procedure A: Simple Equilibrium. In one embodiment, micelle preparation can be carried out as follows. PEG-b-PLA and one, two or three anticancer drugs of interest are dissolved in a suitable water miscible solvent, such as acetonitrile or dimethylacetamide, with optional mixing and/or sonication. The solvent is then removed, for example under reduced pressure to provide a polymer-drug thin film. Warm water (approximately 50° C. to about 70° C.) is added to the polymer-drug film and the mixture is allowed to cool. The drug encapsulating polymeric micelles form upon addition of warm water and then can be isolated, for example, by filtration. See FIG. 12.

Preparatory Procedure B: Simple Equilibrium. In a specific embodiment, 25 mg of PEG-b-PLA, and 10 mg each of paclitaxel, rapamycin, and 17-AAG are dissolved in 2.5-5 mL of acetonitrile. The mixture is mixed and sonicated for five minutes. The solvent is then removed by rotoevaporation at approximately 60° C. to provide a film. Hot (~60° C.) deionized water is added to the oil and the solution is allowed to cool to ~23° C. The solution is then centrifuged to remove the sediment in a 1.5 mL microtube, at ~13,200 rpm for 1 minute. The supernatant is collected and filtered through a 0.2 μm PTFE filter. The isolated micelles can then be stored for extended periods of time at 4° C.

Preparatory Procedure C: Dialysis. In another embodiment, the micelles can be loaded and formed by the following dialysis procedure. PEG-b-PLA and two or three drugs of the desired ratio (e.g., varying from 1:1:20 to 1:20:1 to 20:1:1) are dissolved in a water miscible solvent, such as dimethylacetamide. The mixture is then added to an aqueous solution, such as a 0.9% saline, in a 3500 MWCO tubing (Spectra/Por®) dialysis bag, whereupon the micelles form, incorporating the drugs. The micelle mixture can then be centrifuged (e.g., at ~16,000 rpm for 5 minutes) to precipitate any unincorporated drug. The supernatant can then nanofiltered, and analysis can be carried out using HPLC, such as with UV and RI detection modes (see the techniques described by Yasugi et al., *J. Control. Release*, 1999, 62, 99-100).

Preparatory methods can also include the use of oil-in-water emulsions, solution casting, and/or freeze-drying (lyophylization), as described below in Example 3. Other procedures that can be used include those described by Gaucher et al., *J. Controlled Release*, 109 (2005) 169-188.

Once prepared, the micelle-drug composition can be stored for extended periods of time under refrigeration, preferably at a temperature below about 5° C. Temperatures between about −20° C. and about 4° C. have been found to be suitable conditions for storage of most micelle-drug compositons. Use of brown glass vials or other opaque containers to protect the micelle-drug composition from light can further extend effective lifetimes of the compositions. The micelle-drug compositions can also be freeze-dried into a solid formulation, which can then be reconstituted with an aqueous vehicle prior to administration.

Drug Combinations in PEG-PLA Micelles.

Paclitaxel, 17-AAG, and rapamycin currently require separate formulation in existing vehicles because they all are poorly water-soluble. These current drug vehicles also have to be infused separately into patients via sequential drug administration in a single catheter line, increasing time of administration, or via concurrent drug administration in multiple catheter lines, raising risks of infection and adverse drug interactions. The existing vehicles for drug solubilization are also often toxic, e.g. they include CrEL. The toxicity risks escalate for three-drug cocktails, such as for the combination of paclitaxel, 17-AAG, and rapamycin.

In WO 2009/009067, Kwon et al. describe solubilizing 17-AAG, as well as 17-AAG and paclitaxel, in PEG-b-PLA micelles. Kwon and coworkers have also described PEG-b-PLA micelles carrying a three drug combination that includes 17-AAG, paclitaxel, and etoposide (*J. Control Release* (2009 May 3)). Paclitaxel-rapamycin and paclitaxel-17-AAG combinations have been shown by others to act synergistically. A three-way therapy with a TOR inhibitor, herceptin, and paclitaxel, has also been described. However, these studies were done with separately administered drugs.

Described herein is a single combined formulation that differs from these previous studies because of its safe, effective, non-toxic, and stable delivery system. An approach with sequentially administered micelle drug-encapsulated formulations can now provide similar advantages. In one embodiment, the invention provides a single non-toxic formulation carrying multiple anti-cancer drugs. Such formulations are significant improvements over currently used formulations that use toxic excipients such as Cremophor EL, DMSO, and ethanol. The toxicity of excipients becomes even more critical when two- and three-drug cocktails are being administered to a patent.

Drug solubilization in micelles has not been reduced to a standard practice. Researchers have not been able to develop broadly accepted procedures for determining whether a drug could be solubilized, to what extent, and whether a drug-micelle combination will be stable. The results must be determined empirically. The ability to solubilize multiple drugs in a predictable manner has also escaped the grasp of modern researchers. It is therefore remarkable that the multiple drug micelles described herein load as well as single drug micelles.

Various drugs and drug combinations described herein can be encapsulated within PEG-PLA micelles. An effective amount of the encapsulated drugs can be administered to a patient, for example, to treat cancer. In some embodiments, the drug combinations include any two or three of rapamycin and paclitaxel; or rapamycin, paclitaxel, and 17-AAG, or suitable derivatives thereof, as well as etoposide or teniposide, or other active agents recited herein. For example, in certain embodiments, the paclitaxel can be replaced by an equivalent amount of docetaxel. In some embodiments, rapamycin can be replaced by an equivalent amount of deforolimus, temsirolimus, or everolimus, or alternatively, etoposide or teniposide. Likewise, 17-AAG can be replaced by an equivalent amount of 17-DMAG, geldanamycin, or a derivative thereof (see U.S. Pat. No. 4,261,989 (Sasaki et al.), which is incorporated by reference).

In one embodiment, the invention provides PEG-b-PLA micelles filled with paclitaxel and rapamycin. In another embodiment, the invention provides PEG-b-PLA micelles filled with 17-AAG and rapamycin. In a further embodiment, the invention provides PEG-b-PLA micelles filled with paclitaxel, 17-AAG, and rapamycin. When administered, the micelle formulations of paclitaxel and rapamycin exert synergistic anti-cancer activity, the micelle formulations of 17-AAG and rapamycin exert synergistic anti-cancer activity, and micelle formulations of paclitaxel, 17-AAG, and rapamycin can also exert synergistic anti-cancer activity. Because of their ability to inhibit the mTor pathway at more than one point, each of the drug combination micelle formulations described herein are believed to provide synergistic activity for treating or inhibiting cancer.

Accordingly, several specific two-drug combinations that can be administered using the PEG-PLA micelles include but are not limited to: paclitaxel and 17-AAG; docetaxel and 17-AAG; etoposide and 17-AAG; paclitaxel and rapamycin; 17-AAG and rapamycin; and docetaxel and rapamycin. Specific three-drug combinations that can be administered using the PEG-PLA micelles include but are not limited to: paclitaxel, 17-AAG, and rapamycin; docetaxel, 17-AAG, and rapamycin; and paclitaxel, etoposide, and 17-AAG. Each of the drugs can also be substituted with other drugs recited herein.

Advantages of the Drugs in PEG-PLA Micelles.

The multidrug compositions provide significant advantages to other treatments because lower amounts of one drug can be administered with equivalent or enhanced effect (e.g., see FIGS. 10-11, 13-20, and 23), while also inhibiting other points of enzyme pathways of targeted enzymes. The drug combination formulations can be provided by preparing either simply mixed micelle formulations (wherein each single micelle contains only one type of active agent, and micelles containing different active agents are combined in one formulation) or co-encapsulated micelle formulations (wherein a micelle contains two or three different active agents).

The combination of paclitaxel, 17-AAG, and rapamycin can have synergistic anticancer activity. For example, synergy can be achieved when 17-AAG is administered in combination with paclitaxel, docetaxel, rapamycin, etoposide, or known derivatives thereof. See FIGS. 13-20 and the Examples below.

It was unexpectedly found that the dual-agent micelles could be prepared such that the total drug loading was more than the maximum loading that was obtainable for single-agent micelles. Additionally, this 'additive' effect with respect to drug loading does not result in substantial changes in the resulting diameter of the micelles (see Table 3-1). Multidrug micelles encapsulating three different drugs were also found to follow this additive loading effect, with little or no change in the average micelle diameter, as determined by dynamic light scattering (DLS) techniques. Remarkably, the average micelle diameter of micelles that encapsulated the combination of paclitaxel, etoposide, and 17-AAG was actually smaller than the average diameter of micelles loaded with only paclitaxel or only 17-AAG. In other embodiments, multidrug micelles can be prepared such that the drug loading is within about 20% of the maximum loading that was obtainable for single-agent micelles, up to about 120% of the maximum loading that was obtainable for single-agent micelles (e.g., with respect to the smallest mass of loaded drug).

It was also found that PEG-b-PLA micelles that contain two or more active agents (e.g., 17-AAG and a second agent as described herein) in their cores are more stable with respect to the loss of one of the actives. Thus in micelles containing two active agents, the actives can interact in such a manner as to increase the stability of the micelle, with respect to release of the actives. For example, micelles that contain 17-AAG and a second active agent, such as paclitaxel, docetaxel, rapamycin, or etoposide, were found to be more stable than micelles that incorporate only one of the active agents.

In clinical trials, the combination of 17-AAG and paclitaxel requires DMSO and Cremophor® EL, a four component cocktail, for sufficient delivery. The components of such formulations have been found cause significant adverse side-effects in some patients and the two drugs cannot be mixed and infused together. Also, CrEL and Tween 80 can cause hypersensitivity reactions, peripheral neurotoxicity, inhibition of P-glycoprotein, undesirable pharmacokinetic interactions, and provide poor tumor localization (Tije et al., *Clin. Pharmacokinet.* 42 (2003), 665; Strickley, *Pharm. Res.* 21 (2004), 201). The drug synergy is maximized by concurrent drug administration, but sequential administration can also work synergistically (Solit et al., *Cancer Res.*, 2003; 63:2139-2144). Genexol-PM is currently in phase II clinical trials, therefore paclitaxel/PEG-PLA can be safely administered to patients. An advantage of the compositions described herein is that 17-AAG can be co-loaded into paclitaxel-containing PEG-PLA micelles without requiring a significant increase in the number of the micelles or mass of PEG-PLA polymer. Such formulations can therefore avoid the use of organic solvents or other surfactants when treating patients.

Various conditions can thus be treated using the amphiphilic block copolymer (ABC) micelle systems described herein. Drug synergy can be achieved by use of the micelles, which can reduce the toxicity of a treatment regimen due to drug encapsulation within the micelle delivery vehicles. Combinations of active agents can be used in the individual micelles, or in collections of micelles each having a single type of drug in them. Simply mixed and co-encapsulated formulations allow for the administration of two different active agents with one administration, e.g., an IV infusion. Certain useful combinations and techniques are described in U.S. Pat. No. 7,221,562 (Rosen et al.). In other embodiments, SDM can be administered sequentially to provide the benefits of drug combination therapy.

The micelle compositions described herein provide for highly effective formulations that have unexpectedly high loading capacity for the drugs and drug combinations, and the formulations can be used as controlled release drug delivery systems. It was discovered that the drug loading dual-active micelles can approach, or be equal to, the drug loading capacity of single agent micelles. Additionally, interaction between the actives in the dual-active micelles can increase the stability of such micelles. For example, 17-AAG can act as a stabilizer for dual agent micelle formulations, with respect to both simply mixed formulations and also co-encapsulated formulations.

Drug Formulations of Micelles.

By incorporating a hydrophobic drug such as 17-AAG into PEG-PLA micelles, a larger amount of the drug can be dissolved in a given amount of fluid, such as a pharmaceutical carrier, or body fluid, such as blood or interstitial fluids, than can be dissolved without use of the micelles. Thus, the micelle effectively solubilize the 17-AAG to a higher degree than would be otherwise possible. A pharmaceutical carrier that dissolves the micelles such that the micelles can pass through a filter are considered to be dissolved in a pharmaceutical "solution", to provide a formulation according to an embodiment of the invention.

Most hydrophobic drugs such as paclitaxel, rapamycin, and 17-AAG have a water solubility on the order of micrograms (μg) per mL. The unique combination of the drugs described herein encapsulated in PEG-b-PLA micelles solubilized the drugs at surprisingly high levels, on the order of 4 mg/mL to more than 9 mg/mL. Compared to the solubility of a single hydrophobic drug in PEG-b-PLA micelles, combinations of the hydrophobic drugs show more than merely an additive effect, which is counterintuitive to general assumptions of hydrophobic drug solubility.

In one embodiment, the micelles can solubilize up to about 15 mg/mL of paclitaxel, rapamycin, 17-AAG, or a combination thereof, or up to about 20 mg/mL of the drugs, in combination. In some embodiments, the micelles can solubilize about 3 mg/mL, about 5 mg/mL, about 10 mg/mL, about 15 mg/mL, about 20 mg/mL, or about 25 mg/mL of the drugs. In some embodiments, the formulation can have concentrations of about 0.5 to about 5 mg/mL of the drugs, about 0.75 to about 3 mg/mL of the drugs, about 1 to about 2 mg/mL of the drugs, or about 1.5 mg/mL, with respect to the volume of micelles or preferably, the volume of the aqueous carrier. Similar amounts of other combinations of the drugs can be included in micelles of certain other embodiments.

In one embodiment, the drug encapsulated micelles are formulated in a mixture that includes an aqueous carrier, such as saline or dextrose, and the like. For example, a suitable carrier can be 0.9% NaCl solution, or a 5% aqueous saccharide solution, such as a dextrose or glucose solution. See, *Remington: The Science and Practice of Pharmacy*, D. B. Troy, Ed., Lippincott Williams & Wilkins (21$^{st}$ Ed., 2005) at pages 803-849.

For purposes of administration, for example, parenteral administration, sterile aqueous solutions of water-soluble salts (e.g., NaCl) can be employed. The aqueous solutions can be isotonic. Additional or alternative carriers may include sesame or peanut oil, as well as aqueous propylene glycol. Aqueous solutions may be suitably buffered, if necessary, and the liquid diluent can first be rendered isotonic with sufficient saline or glucose. These aqueous solutions are especially suitable for intravenous, intramuscular, subcutaneous, intraperitoneal, and intratumoral (IT) injection. Intratumoral injection can be especially helpful for certain types of therapy, such as the treatment of cancer, including prostate cancer. Appropriate sterile aqueous media can be purchased (e.g., Sigma-Aldrich Corporation, St. Louis, Mo.) or can be prepared by standard techniques well known to those skilled in the art.

In some embodiments, the compositions are completely free of additives such as one or more of ethanol, dimethyl sulfoxide, or other organic solvents, phospholipids, castor oil, and castor oil derivatives. In other embodiments, the composition is substantially free of such components. As used herein, substantially free means that the composition contains less than about 2.5 wt. %, less than about 2 wt. %, less than about 1.5 wt. %, less than about 1 wt. %, less than about 0.5 wt. %, or less than about 0.25 wt. %. In some embodiments, certain additives can increase the stability of the micelles. In one embodiment, a surfactant can be included in the micelle (e.g., in about 0.25 wt. % to about 2.5 wt. %). For example, a suitable surfactant can be a negatively charged phospholipid, such as polyethylene glycol conjugated distearoyl phosphatidyl-ethanolamine (PEG-DSPE).

Therapy Using Micelle Formulations.

The lack of suitable formulations has hindered the progression of 17-AAG into clinical trials. Newer derivatives, such as 17-DMAG (alvespimycin), have overcome some problems associated with water solubility. However, the preferential and rapid clearance of these derivatives by the liver limits drug distribution into tumors, thereby severely limiting the efficacy of the drug. A formulation of 17-AAG that does not require organic co-solvents or harsh surfactants has been prepared. The formulation can solubilize 1.5 mg/mL of 17-AAG in PEG-PLA (12:6 kDa) micelles. A second formulation of 17-AAG that does not require organic co-solvents or surfactants has been prepared. This formulation can solubilize about five mg/mL of 17-AAG in PEG-PLA (2:2 kDa) micelles. Similar work with paclitaxel encapsulation into PEG-PLA micelles has demonstrated that this safer micellar formulation can minimize adverse side effects associated with CrEL following administration of the drug to patients. In addition, the nanoscale dimensions will further benefit tumor specificity of the drug through the EPR effect even in the absence of targeting ligands.

The micelles can be formulated into a pharmaceutical solution and administered to a patient. The pharmaceutical solution formulation can allow for delivery of a requisite amount of the drugs to the body within an acceptable time, for example, about 10 minutes, to about 3 hours, typically about 1 to about 2 hours, for example, about 90 minutes. The administration can be parenteral, for example, by infusion, injection, or IV, and the patient can be a mammal, for example, a human. Upon administration, the micelles can circulate intact, dissociate into individual polymer chains, release active agents (either by diffusion or micelle dissociation), distribute into tissue (e.g. tumors), and/or undergo renal clearance. The schedule of these events cannot be predicted with specificity, and these events significantly influence the antitumor activity of the active agents, such as paclitaxel, rapamycin, or 17-AAG.

In some embodiments, the drug-loaded micelles can extravasate into tumor interstices, at which point the active agent-containing micelles release the drugs from the micelles due to the intracellular conditions. The active agent can then diffuse into tumor cells. Another aspect of the invention includes the micelles crossing leaky vasculature and endocytosing into tumor cells, and inhibiting the tumor cell growth, and/or killing the tumor cells.

A disease, disorder, or condition can be treated by administering a pharmaceutical formulation of micelles that contain the drug combinations recited herein. Administration of the compositions described herein can result in a reduction in the size and/or the number of cancerous growths in a patient, and/or a reduction in one or more corresponding associated symptoms. When administered in an effective amount by the methods described herein, the compositions of the invention can produce a pathologically relevant response, such as inhibition of cancer cell proliferation, reduction in the size of a cancer or tumor, prevention of further metastasis, inhibition of tumor angiogenesis, and/or death of cancerous cells. The method of treating such diseases and conditions described below includes administering a therapeutically effective amount of a composition of the invention to a patient. The method may be repeated as necessary, for example, daily, weekly, or monthly, or multiples thereof.

Conditions that can be treated include, but are not limited to, hyperproliferative diseases, including cancers of the head and neck, which include tumors of the head, neck, nasal cavity, paranasal sinuses, nasopharynx, oral cavity, oropharynx, larynx, hypopharynx, salivary glands, and paragangliomas; cancers of the liver and biliary tree, particularly hepatocellular carcinoma; intestinal cancers, particularly colorectal cancer; ovarian cancer; small cell and non-small cell lung cancer; prostate cancer; pancreatic cancer; breast cancer sarcomas, such as fibrosarcoma, malignant fibrous histiocytoma, embryonal rhabdomyosarcoma, leiomyosarcoma, neurofibrosarcoma, osteosarcoma, synovial sarcoma, liposarcoma, and alveolar soft part sarcoma; neoplasms of the central nervous systems, particularly brain cancer; and/or lymphomas such as Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, or T-cell anaplastic large cell lymphoma.

Non-cancer conditions that are characterized by cellular hyperproliferation can also be treated using the methods described herein. For example, the drugs can be administered according to the methods described herein to treat conditions that are characterized by cellular hyperproliferation. Illustrative examples of such non-cancer conditions, disorders, or diseases include, but are not limited to, atrophic gastritis, inflammatory hemolytic anemia, graft rejection, inflammatory neutropenia, bullous pemphigoid, coeliac disease, demyelinating neuropathies, dermatomyositis, inflammatory bowel disease (ulcerative colitis and/or Crohn's disease), multiple sclerosis, myocarditis, myositis, nasal polyps, chronic sinusitis, pemphigus vulgaris, primary glomerulonephritis, psoriasis, surgical adhesions, stenosis or restenosis, scleritis, scleroderma, eczema (including atopic dermatitis. irritant dermatitis, allergic dermatitis), periodontal disease (i.e., periodontitis), polycystic kidney disease, and type I diabetes. Other examples include vasculitis, e.g., Giant cell arteritis (temporal arteritis, Takayasu's arteritis), polyarteritis nodosa, allergic angiitis and granulomatosis (Churg-Strauss disease), polyangitis overlap syndrome, hypersensitivity vasculitis (Henoch-Schonlein purpura), serum sickness, drug-induced vasculitis, infectious vasculitis, neoplastic vasculitis, vasculitis associated with connective tissue disorders, vasculitis associated with congenital deficiencies of the complement system, Wegener's granulomatosis, Kawasaki's disease, vasculitis of the central nervous system, Buerger's disease and systemic sclerosis; gastrointestinal tract diseases, e.g., pancreatitis, Crohn's disease, ulcerative colitis, ulcerative proctitis, primary sclerosing cholangitis, benign strictures of any cause including ideopathic (e.g., strictures of bile ducts, esophagus, duodenum, small bowel or colon); respiratory tract diseases (e.g., asthma, hypersensitivity pneumonitis, asbestosis, silicosis and other forms of pneumoconiosis, chronic bronchitis and chronic obstructive airway disease); nasolacrimal duct diseases (e.g., strictures of all causes including idiopathic); eustachian tube diseases (e.g., strictures of all causes including idiopathic); as well as neurological diseases, fungal diseases, viral infections, and/or malaria.

The terms "treat" and "treatment" refer to any process, action, application, therapy, or the like, wherein a mammal, including a human being, is subject to medical aid with the object of improving the mammal's condition, directly or indirectly. Treatment typically refers to the administration of an effective amount of a micelle composition as described herein.

The terms "effective amount" or "therapeutically effective amount" are intended to qualify the amount of a therapeutic agent required to relieve to some extent one or more of the symptoms of a condition, disease or disorder, including, but not limited to: 1) reduction in the number of cancer cells; 2) reduction in tumor size; 3) inhibition of (i.e., slowing to some extent, preferably stopping) cancer cell infiltration into peripheral organs; 3) inhibition of (i.e., slowing to some extent, preferably stopping) tumor metastasis; 4) inhibition, to some extent, of tumor growth; 5) relieving or reducing to some extent one or more of the symptoms associated with the disorder; and/or 6) relieving or reducing the side effects associated with the administration of active agents.

The term "inhibition," in the context of neoplasia, tumor growth or tumor cell growth, may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition, can be referred to as prevention or chemoprevention. The inhibition can be about 10%, about 25%, about 50%, about 75%, or about 90% inhibition, with respect to progression that would occur in the absence of treatment.

Using a pharmaceutical solution formulation of this invention, active agents such as paclitaxel, rapamycin, 17-AAG and/or an anticancer or cytotoxic agent may be administered in a dose ranging from about 4 mg/m$^2$ to about 4000 mg/m$^2$, depending on the frequency of administration. In one embodiment, a dosage regimen for the drug combinations can be about 400-500 mg/m$^2$ weekly, or about 450 mg/m$^2$ weekly. See Banerji et al., *Proc. Am. Soc. Clin. Oncol.*, 22, 199 (2003, abstract 797). Alternatively, a dose of about 300 mg/m$^2$ to about 325 mg/m$^2$, or about 308 mg/m$^2$ weekly can be administered to the patient. See Goetz et al., *Eur. J. Cancer,* 38 (Supp. 7), S54-S55 (2002). Another dosage regimen includes twice weekly injections, with doses ranging from about 200 mg/m$^2$ to about 360 mg/m$^2$ (for example, about 200 mg/m$^2$, about 220 mg/m$^2$, about 240 mg/m$^2$, about 250 mg/m$^2$, about 260 mg/m$^2$, about 280 mg/m$^2$, about 300 mg/m$^2$, about 325 mg/m$^2$, 340 mg/m$^2$, about 350 mg/m$^2$, or about 360 mg/m$^2$, depending on the severity of the condition and health of the patient). A dosage regimen that can be used for combination treatments with another drug, such as paclitaxel or docetaxel, can administer the two drugs every three weeks, with the dose of 17-AAG of about 500 mg/m$^2$ to about 700 mg/m$^2$, or up to about 650 mg/m$^2$ at each administration. Other concurrent dosing schedules that can be employed are described by Fung et al., *Clin. Cancer Res.* 2009; 15(17), 5389-5395.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

17-AAG Encapsulation in PEG-b-PLA Micelles

Preparation of 17-(allylamino)-17-demethoxygeldanamycin. 17-AAG was synthesized in the lab from geldanamycin (GA) (LC Laboratories, Woburn, Mass.). Briefly, 100 mg of GA (0.2 mmol) was dissolved in 2 mL of dry $CH_2Cl_2$. Next, 5 equivalents of allylamine (57.1 g/mol, d=0.763 g/mL) was added dropwise to the flask. The reaction was stirred at room temperature (RT; ~23° C.) under low light until complete by TLC analysis (approx. 2 days) (95:5 $CHCl_3$:MeOH, $R_f$ 0.21), precipitated with hexane (3×), centrifuged at 2000 g's for 15 minutes, and evaporated to dryness. Yield: 95 mg, 95%; MS m/z 584 (M−); $^1$H NMR ($CDCl_3$) δ 0.99 (m, 6H, 10-Me, 14-Me), 1.25 (t, 1H, H-13), 1.60-1.85 (br m, 6H, H-13, H-14, 8-Me), 2.05 (s, 3H, 2-Me), 2.46 (br m, 2H, H-15), 2.83-2.90 (br m, 3H, H-10), 3.27 (s, 3H, OMe), 3.36 (s, 3H, OMe), 3.40 (t, 1H, H-12), 3.58-3.68 (br m, 2H, H-11, H-23), 4.31 (d, 1H, H-7), 5.10 (br s, 1H), 5.21-5.55 (br m, 3H, H-9, H-24), 5.86-5.99 (br t, 2H, H-5, H-23), 6.59 (t, 1H, H-4), 6.94 (d, 1H, H-3), 7.28 (br s, 1H, H-19).

Preparation and characterization of drug loaded PEG-PLA micelles. 17-AAG was formulated by dissolving it with PEG-PLA (12:6 kDa) (Polymer Source, Montreal, Canada) in dimethylacetamide (DMAc) and dialyzing against $H_2O$, following procedures by Kataoka and coworkers (*J. Control. Release* 62(1-2) (1999) 89-100). For example, 5 mg of 17-AAG and 45 mg of PEG-PLA (10:90 w/w) were dissolved in 10 mL DMAc. The resulting solution was dialyzed against $H_2O$ in 3500 MWCO tubing (SpectraPor). Resulting micelles were centrifuged at 5000 g's for 10 minutes to precipitate unincorporated drug. Incorporation into micelles was verified using aqueous GPC (Shodex SB-806M) by confirming equivalent retention times based on refractive index for the micelles and absorbance of 17-AAG (UV λ332). Micelle solutions were concentrated by rotary evaporation under reduced pressure at room temperature, followed by centrifugation (5000 g's for 10 minutes).

Quantitative drug loading in micelles was determined by monitoring the area under the curve (AUC) for 17-AAG (based on a 17-AAG calibration curve) through reverse-phase HPLC (Shodex C18 column, 65-82.5:35-17.5 MeOH to 55% MeOH+0.2% formic acid gradient, 40° C., 332 nm detection). Effective diameters of PEG-PLA micelles, with and without drugs, were measured using a Brookhaven dynamic light scattering apparatus (100 mW, 532 nm laser) with Gaussian intensity fitting. The critical micelle concentration (CMC) for these PEG-b-PDLLA micelles was determined by measuring the 339/334-nm excitation ratio of pyrene in the presence of various concentrations of PEG-PLA ($3\times10^{-5}$ mg·mL$^{-1}$ to 1 mg·mL$^{-1}$).

Briefly, PEG-b-PDLLA micelles were prepared as described above in serial dilutions and incubated with 0.6 µM pyrene for 1 hour at 80° C., allowed to sit in the dark for 15 hours at RT, and the fluorescence emission of pyrene was measured at 390 nm (RF-5301 PC spectrofluoro-photometer, Shimadzu). Pyrene undergoes well-known photophysical changes in response to its microenvironment polarity (*Colloids Surf., A Physiochem. Eng. Asp.* 118 (1996) 1-39). A sharp increase in the ratio of 339/334 nm excitation occurs at the CMC as the pyrene preferentially partitions into the hydrophobic cores of PEO-b-PDLLA micelles (*J. Control. Release* 77(1-2) (2001) 155-160).

Micelle formulations can be prepared, characterized, and evaluated, as described in WO 2009/009067 (Kwon et al.), for example, analogous to the procedures described in Examples 2 and 3 therein.

Example 2

Drug Solubilization; Reference Examples

Several polymers that form micelles with drugs were surveyed for solubilizing a paclitaxel-rapamycin-17-AAG drug combination. The combination proved difficult to solubilize without a correct set of micellar properties. For example, the PEG-PPG-PEG triblock polymer Poloxamer F68 is useful to solubilize many hydrophobic compounds such as resveratrol, a hydrophobic compound with reported anticancer activity. Poloxamer F68, however, was unable to solubilize paclitaxel, rapamycin, or 17-AAG individually, or the combination of paclitaxel, rapamycin, and 17-AAG. In these attempts, the micelles coagulated and deteriorated in aqueous solutions.

Conversely, PEG-b-PLA does not form stable micelles when combined with resveratrol, but does form very stable micelles with both 17-AAG and the paclitaxel-rapamycin-17-AAG drug combination. Additionally, the tri-drug loaded PEG-b-PLA micelles display remarkable properties by solubilizing the drugs in a nearly additive fashion. Thus suitable polymers for solubilizing each drug and drug combination must be determined empirically because no reliable predictive trends exist at this time.

Results for forming micelles of the paclitaxel-rapamcyin-17-AAG combination with Poloxamer F68:

(1) Rapamycin (rap) by itself with Poloxamer F68: loading efficiency was poor. After reconstitution, rapamycin=0.09 mg/mL (initial concentration=2.4 mg/mL); only 4% loading into micelles and formed a white precipitation upon addition of water.

(2) Rapamycin, paclitaxel and 17-AAG with Poloxamer F68: loading efficiency was also poor.

Final concentration of rap=0.35 mg/mL (initial conc.=2.4 mg/mL): 15% loading.

Final concentration of paclitaxel=0.80 mg/mL (initial conc.=4.1 mg/mL): 15% loading.

Final concentration of 17-AAG=0.67 mg/mL (initial conc.=4.1 mg/mL): 16% loading.

Example 3

Multi-Drug Loaded Polymeric Micelles for Simultaneous Delivery of Poorly Soluble Anticancer Drugs PEG-b-PLA, an amphiphilic block copolymer, assembles readily in water into micelles. It has been shown to raise the solubility of paclitaxel (PTX) from approximately 1 µg/mL to 10 mg/mL. PEG-b-PLA is much less toxic than CrEL. However, a recent phase II clinical trial in metastatic breast cancer patients showed that PTX dosed as part of PEG-b-PLA micelles, without premedication with corticosteroids and histamine antagonists, does induce hypersensitivity reactions, albeit less severely than CrEL. PEG-b-PLA micelles increase the maximum tolerated dose of PTX in humans in comparison to CrEL, enhancing its anti-tumor efficacy. There is also evidence that PEG-b-PLA micelles impart linear PK for PTX, strongly contrasting with CrEL that induces a non-linear PK profile for PTX, i.e. lowering its clearance with dose escalation. Using these PEG-b-PLA micelles to raise the solubility of various anticancer agents is a potential delivery option, facilitating ease of entry into clinical trials in the cancer arena.

However, due to the heterogeneity of cancer cells as well as acquired drug resistance, single agent therapy is limited and combination chemotherapy has become a standard regimen to treat cancer patients. To be specific, drug combinations are beneficial in the view of retarding occurrence of resistant cell lines and wide coverage against multiple cell lines, resulting in maximum cell killing effect within acceptable toxicity. Synergistic drug combinations produce an even greater response rate or survival time than is possible with each drug used alone at its optimum dose. For example, 17-AAG, a prototype Hsp90 inhibitor, had synergistic effects with a broad range of anticancer agents in different tumor cell lines. 17-AAG causes a remarkable combinatorial depletion of multiple oncogenic proteins, e.g. Akt, ErbB-2, and Hif-1a, causing a blockage of cancer-causing and survival pathways, and there is keen interest in the combination of chemotherapy and 17-AAG.

In the case of PTX and 17-AAG or rapamycin, it has been shown that PTX sensitizes cancer cells to apoptosis induced by 17-AAG, a mitotic inhibitor with anti-neoplastic activity, when the drugs are given together or when PTX treatment was followed by exposure to 17-AAG. Similar effects are founds when PTX is given together with rapamycin or when PTX treatment was followed by exposure to rapamycin. These two drug combination were synergistic in various cancer cell lines and in mice. Additionally in mice bearing H358 human non-small-cell lung cancer xenografts, PTX cytotoxicity was enhanced by 5-22 fold when combined with 17-AAG. The combination of PTX and 17-AAG was also evaluated in humans and showed enhanced efficacy and better tolerability profile as compared to PTX alone. In another case, 17-AAG has also enhanced the activity of ETO, a topoisomerase II inhibitor, in vitro and in vivo. The combination of 17-AAG and ETO showed synergism in leukemia cells. Another study demonstrated the combination of 17-AAG and ETO decreased the $IC_{50}$ of ETO by 10 fold in four different pediatric acute lymphoblastic leukemia cell lines.

However, despite the advantages of combination chemotherapy, one of the main problems associated with clinical use is the complicated regimens that must be administered to patients. As most anticancer drugs are poorly water soluble and utilize toxic excipients to enhance their solubility, combining two or three drugs can be challenging in clinical practice, owing to compatibility and stability issues. Thus, using PEG-b-PLA micelles to rationally design and deliver chemotherapeutic regimens instead of single anticancer agents might be a better approach to overcome these formulation related and clinical challenges. In previous work, 17-AAG was solubilized in PEG-b-PLA micelles (Xiong et al., *J. of Pharm. Sci.* 98 (2009) 1577-1586). The PK profile of 17-AAG in these micelles was similar to CrEL in rats, without the attendant toxicity observed with the CrEL formulation (no deaths versus 35% mortality for CrEL). Therefore, a PEG-b-PLA micellar systems was developed as described herein that can simultaneously deliver multiple anticancer agents, like PTX, DCTX, or ETO by co-solubilizing them with 17-AAG to generate safer, more stable formulations for potentially synergistic combination chemotherapy.

Materials. PEG-b-PLA (Mn PEG and PLA were 4.2 K and 1.9 K respectively, PDI=1.05) was purchased from Advanced Polymer Materials Inc. (Montreal, CAN). Paclitaxel was obtained from LKT laboratories Inc. (St. Paul, Minn.). Docetaxel and 17-AAG were purchased from LC Laboratories (Woburn, Mass.). Etoposide, DMSO-$d_6$ and $D_2O$ were purchased from Sigma-Aldrich Inc. (St. Louis, Mo.). All other materials were obtained from Fisher Scientific Inc. (Fairlawn, N.J.). All reagents were HPLC grade.

Preparation and Characterization of Drug-Loaded PEG-b-PLA Micelles. Single drug micelles (SDMs) were prepared by adding 2.0 mg of PTX, DCTX, ETO or 17-AAG and 15 mg of PEG-b-PLA in a 5.0 mL round bottom flask. The drug-polymer mixture was dissolved in 0.50 mL acetonitrile (ACN). The ACN was removed at 60° C. under reduced pressure on a rotary evaporator resulting in the formation of a homogenous film. The drug-polymer film was rehydrated with 0.50 mL of DD $H_2O$ at 60° C. with gentle agitation resulting in a clear solution of drug-loaded PEG-b-PLA micelles. The micellar solution was filtered using a 0.45 μm filter, and the micelles were characterized in terms of size and loading by Dynamic Light Scattering (DLS) and HPLC respectively.

PEG-b-PLA was also used to prepare multiple drug micelles (MDMs) with different drug combinations of PTX/17-AAG, DCTX/17-AAG, ETO/17-AAG and PTX/ETO/17-AAG. MDMs were prepared similarly to the SDMs by mixing 2.0 mg of each drug with 15 mg of the polymer. The procedure for the preparation and characterization of these micelles was identical to the SDMs.

Drug(s) to polymer w/w percent was calculated for SDM and MDM. PEG-b-PLA micelles were freeze dried, weighed and the amount of drug(s) in the freeze dried sample was quantified by HPLC. The drug w/w percent was calculated as the mass of the drug(s) to the mass of polymer in the freeze dried sample multiplied by 100.

Quantification of Drug Loading in SDM and MDM by Reverse Phase HPLC. The content of drug loaded in PEG-b-PLA micelles was quantified by reverse phase HPLC. The HPLC system used for quantifying was a Shimadzu prominence HPLC system (Shimadzu, JP), consisting of a LC-20AT pump, SIL-20AC HT autosampler, CTO-20AC column oven and a SPD-M20A diode array detector. A sample of 10 μL was injected into a Zorbax SB-C8 Rapid Resolution cartridge (4.6×75 mm, 3.5 micron, Agilent). The column temperature was maintained at 40° C. throughout the run. Two HPLC methods were developed to quantify the amount of the drug(s) loaded in PEG-b-PLA micelles.

The first method was developed to quantify PTX, DCTX and 17-AAG in SDM or MDM. The mobile phase was an isocratic mixture of 45% ACN and 54% aqueous phase containing 0.1% phosphoric acid and 1% methanol in DD $H_2O$. The run time was 10 min, the flow rate was 1.0 mL/min and the detection was at 227 nm for PTX and DCTX, while 17-AAG was detected at 333 nm. The retention times of 17-AAG, PTX, and DCTX were 5.6, 6.8 and 8.1 min, respectively, while the limits of detection (LODs) of the three drugs by this method were 1.00, 0.52, and 0.43 μg/mL, respectively.

The second HPLC method was developed to quantify PTX, ETO and 17-AAG in SDM or MDM. The mobile phase was a gradient mixture of ACN and aqueous phase containing 0.1% phosphoric acid and 1% methanol in DD $H_2O$. The run time was 15 min, the flow rate was 1.0 mL/min and the detection was at 227 nm for PTX and ETO while 17-AAG was detected at 333 nm. The retention times of ETO, PTX and 17-AAG were 3.3, 8.0 and 8.5 min respectively while LODs of the three drugs were 0.55, 0.47 and 0.43 μg/mL, respectively. With both HPLC methods samples were injected twice and reproducible and rapid separation of the drugs was achieved.

Dynamic Light Scattering (DLS) Measurements of SDM and MDM. The size of the micelles was determined by DLS using a ZETASIZER Nano-ZS (Malvern Instruments Inc., UK) equipped with He—Ne laser (4 mW, 633 nm) light source and 90° angle scattered light collection configuration. The drug-loaded micellar solutions were diluted 20 times with DD $H_2O$ and the samples was equilibrated for 2 min at 25° C. before the measurements. Final PEG-b-PLA concentration was approximately 1.5 mg/mL. The hydrodynamic diameter of PEG-b-PLA micelles was calculated based on the Stokes-Einstein equation. Correlation function was curve fitted by cumulant method to calculate mean size and polydispersion index (PDI). All measurements were repeated three times, and volume-weighted particle sizes were presented as the average diameter with standard deviation.

Turbidity Measurements of SDM and MDM. Turbidity measurements were used to evaluate the physical stability of drug-loaded PEG-b-PLA micelles. A CARY 50 BIO UV-Visible spectrophotometer equipped with dip probe was used to measure turbidity. Micellar solutions were diluted six times, for a final concentration of PEG-b-PLA of 5 mg/mL, with DD $H_2O$ and filtered through 0.45 µm filter. The absorbance of each sample was recorded at 650 nm and collected over 24 hours at ambient temperature (~23° C.). Each measurement was performed in triplicate.

$^1H$ NMR spectroscopy of SDM and MDM. $^1H$ NMR spectroscopy was used to confirm the incorporation of drugs into PEG-b-PLA micelles. Individual drugs or multiple drugs in PEG-b-PLA polymer films were prepared as described above. The formed film was solubilized in 0.70 mL of DMSO-$d_6$ or in 0.70 mL $D_2O$ warmed to 60° C., and the $^1H$ NMR spectrum recorded for each sample. $^1H$ NMR measurements were performed on $^{UNITY}$INOVA NMR spectrometers (Varian, USA) model operating at 400 MHz normal proton frequencies. Sample temperature was regulated for all measurements and was set at 25° C. The spectrometer was equipped with FTS Systems preconditioning device (composed of refrigerating unit, internal temperature controller and inclusion transfer line). To control pre-cooling or pre-heating of the compressed and dried air used as temperature control medium: final temperature regulation of the sample was achieved within the NMR probe. Acquisition parameters were adjusted on a case-by-case basis to provide adequate signal-to-noise ratio and spectral resolution, the latter typically at 0.5 ppB/point for 1D High-resolution proton. More specifically, protons were excited by a single n/2 pulse followed by detection of the proton signal.

In Vitro Release Profiles of Drug(s) from SDM and MDM. The release profile of PTX, DCTX, ETO and 17-AAG from PEG-b-PLA micelles was evaluated by a dialysis method. SDMs or MDMs were prepared and characterized as described above. Post micelle preparation each sample was diluted with DD $H_2O$, to yield about 0.10 mg/mL of each drug. A volume of 2.5 mL of the prepared sample was loaded into a 3 mL Slide-A-Lyzer® (Thermo Scientific Inc.) dialysis cassette with a MWCO of 20,000 g/mol. Four cassettes were used in each experiment. The cassettes were placed in 2.0 L of buffer which was changed every 3 hours to ensure sink conditions for drug(s) and polymer. A sample of 100 µL was drawn from each cassette at various sampling time intervals and then replaced with 100 µL of fresh buffer. The sampling time intervals were 0, 0.5, 2, 3, 6, 9, 12 and 24 hours. The amount of drug(s) in each sample was quantified by HPLC as described above.

Data Analysis. Statistical analysis was performed using one-way ANOVA at 5% significance level combined with Tukey's Multiple Comparison Test or t-test at 5% significance level. Curve-fitting analysis using one phase exponential association was used to calculate the half-life ($t_{1/2}$) of drug in in vitro drug release experiments. Both analyses were performed using GraphPad Prism version 5.00 for Windows, Graph-Pad Software, San Diego Calif. USA, www.graphpad.com.

Figure 1:
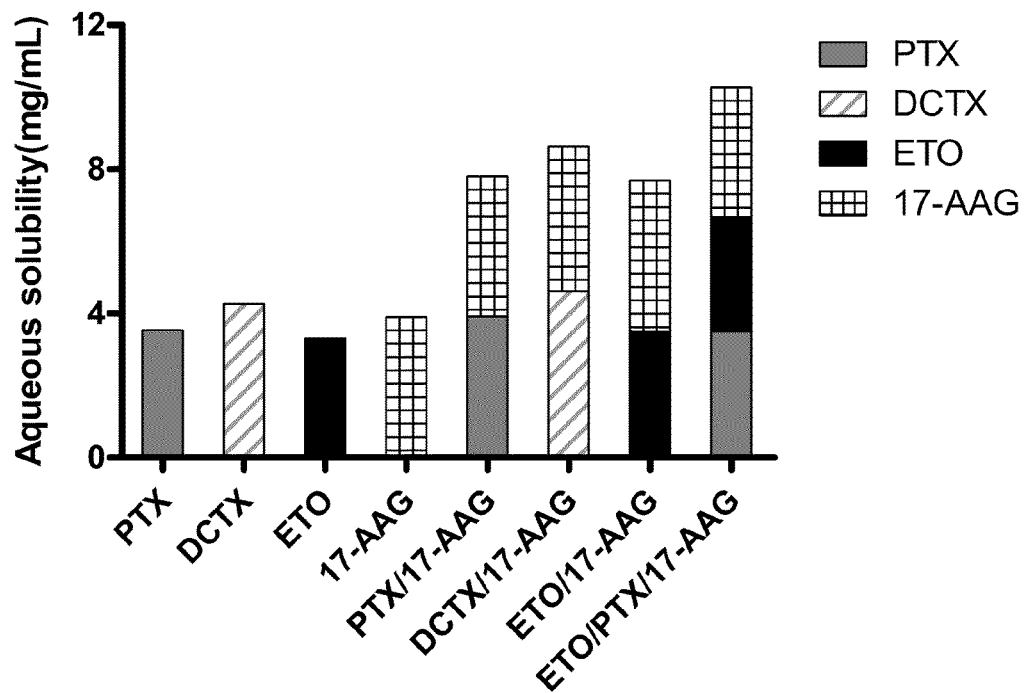
FIG. 1 illustrates the aqueous solubility of certain drugs and drug combinations in SDM and MDM (n=3).

Preparation and Characterization of Drug-Loaded PEG-b-PLA Micelles. SDMs were prepared for PTX, DCTX, ETO or 17-AAG with PEG-b-PLA. The solubility of all drugs in the micelles was starkly significantly higher as compared to their intrinsic solubility in water (Table 3-1 and FIG. 1). PTX solubility increased from 0.0003 mg/mL to 3.50 mg/mL. DCTX solubility increased from 0.0055 mg/mL to 4.27 mg/mL. ETO solubility also increased from 0.0580 mg/mL to 3.17 mg/mL. 17-AAG solubility increased from 0.1000 mg/mL to 4.21 mg/mL.

TABLE 3-1

Drug Combination Solubilization Results for PEG-b-PLA Micelles: Physical Characterization of SDM and MDM (n = 3 ± SD).

| Anticancer agent | drug level in water (mg/mL) | % drug loading (wt. drug(s)/ wt. polymer) | PEG-b-PLA micelle diameter (nm ± SD) |
|---|---|---|---|
| Paclitaxel | 3.54 ± 0.32 | 11.8 ± 1.1 | 38.8 ± 0.6 |
| Docetaxel | 4.27 ± 0.44 | 14.2 ± 1.5 | 37.3 ± 1.7 |
| Etoposide | 3.31 ± 0.15 | 11.0 ± 0.5 | 32.6 ± 1.0 |
| 17-AAG | 3.90 ± 0.28 | 13.0 ± 0.9 | 39.3 ± 2.9 |
| Paclitaxel + 17-AAG | 3.92 ± 0.17 / 3.88 ± 0.29 | 26.0 ± 1.4 | 38.9 ± 1.1 |
| Docetaxel + 17-AAG | 4.62 ± 0.44 / 4.01 ± 0.08 | 28.8 ± 0.2 | 39.0 ± 0.8 |
| Etoposide + 17-AAG | 3.49 ± 0.24 / 4.21 ± 0.38 | 25.6 ± 1.3 | 35.3 ± 1.2 |
| Etoposide + Paclitaxel + 17-AAG | 3.17 ± 0.04 / 3.50 ± 0.20 / 3.61 ± 0.33 | 34.3 ± 1.6 | 36.5 ± 0.5 |

(n = 3, Mean ± SD)

PEG-b-PLA was used to prepare MDM with different drug combinations of PTX/17-AAG, DCTX/17-AAG, ETO/17-AAG and PTX/ETO/17-AGG. The magnitude of solubility enhancement for all drugs in the MDM micelles was similar to the SDMs. The presence of multiple drugs within PEG-b-PLA micelles did not adversely affect the apparent solubility enhancement of the individual drugs in a statistically significant manner (Table 3-1 and FIG. 1). The drug(s) to polymer w/w percents of SDM and MDM are listed in Table 3-1. For SDM, PTX, DCTX, ETO and 17-AAG w/w percents were 10.3, 11.5, 9.6 and 11.3% respectively. The w/w percents for all drugs in the MDM were statistically the same as the SDM. For all SDMs and MDMs approximately 100% of the initial amount of the drug(s) and polymer was recovered as loaded PEG-b-PLA micelles. The capacity of these PEG-b-PLA micelles to incorporate drugs increased as the number drugs being loaded increased. For SDM the loading capacity % w/w was approximately 10%, with two drug MDM the loading capacity of the micelle increased to approximately 25% w/w and with three-drug MDM the loading capacity was approximately 35% w/w.

DLS Measurements of SDM and MDM. The sizes of unloaded PEG-b-PLA micelle, SDMs and MDMs measured by DLS are listed in Table 3-1. All micelles exhibited a unimodal distribution with a size range of 30-40 nm. PDIs of all SDMs and MDMs were below 0.2, indicating narrow particle size distribution.

Turbidity Measurements of SDM and MDM. The physical stability of SDM and MDM was evaluated by turbidity measurements. The increase in turbidity, as measured by changes in absorbance at 650 nm, over time correlates with drug precipitation following release from PEG-b-PLA micelles. The turbidity measurements were further supported by HPLC and DLS measurements. SDM with 17-AAG is physically stable over 24 hours without a change in particle size or drug loss (Table 3-2).

TABLE 3-2

Drug Loss from PEG-b-PLA Micelles After 24 Hours: Initial
solubility and solubility at 24 h of drug(s) in SDM and MDM
as assessed by reverse phase HPLC (n = 3 ± SD).

| Anticancer agent | initial drug level in water (mg/mL) | drug level @ 24 hr in water (mg/mL) | % w/w drug(s) left @ 24 hr |
|---|---|---|---|
| Paclitaxel | 3.54 ± 0.32 | 0.57 ± 0.07 | 16.2 ± 1.0 |
| Docetaxel | 4.27 ± 0.44 | 1.14 ± 0.03 | 26.8 ± 3.3 |
| Etoposide | 3.31 ± 0.15 | 1.07 ± 0.16 | 32.3 ± 3.4 |
| 17-AAG | 3.90 ± 0.28 | 3.84 ± 0.18 | 98.6 ± 2.4 |
| Paclitaxel + 17-AAG | 3.92 ± 0.17 | 3.86 ± 0.15 | 98.5 ± 0.3 |
|  | 3.88 ± 0.29 | 3.77 ± 0.28 | 96.9 ± 0.2 |
| Docetaxel + 17-AAG | 4.62 ± 0.44 | 4.45 ± 0.13 | 96.3 ± 1.8 |
|  | 4.01 ± 0.08 | 3.83 ± 0.17 | 95.5 ± 2.7 |
| Etoposide + 17-AAG | 3.49 ± 0.24 | 3.28 ± 0.19 | 94.1 ± 1.5 |
|  | 4.21 ± 0.38 | 3.95 ± 0.39 | 93.9 ± 1.1 |
| Etoposide + Paclitaxel + 17-AAG | 3.17 ± 0.04 | 3.11 ± 0.06 | 98.2 ± 1.1 |
|  | 3.50 ± 0.20 | 3.46 ± 0.18 | 98.7 ± 1.3 |
|  | 3.61 ± 0.33 | 3.52 ± 0.33 | 97.5 ± 1.4 |

Figure 2:
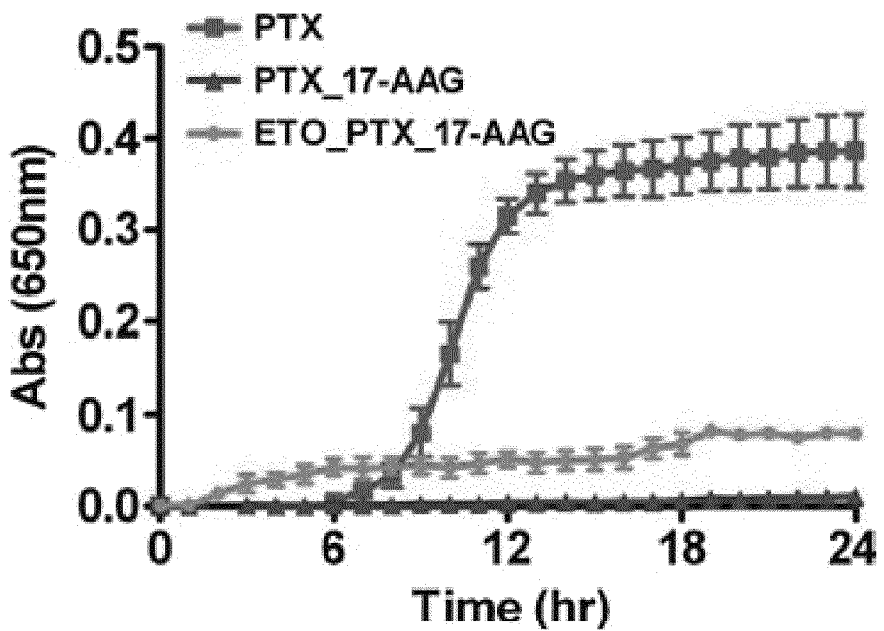
FIG. 2 illustrates turbidity measurements of SDM with PTX, PTX/17-AAG MDM and PTX/ETO/17-AAG MDM (n=3, Mean±SD).

SDM with PTX (FIG. 2), DCTX and ETO were stable for approximately 6 hours. HPLC data shows that at 24 hours approximately 84%, 73% and 68% of PTX, DCTX and ETO precipitated, respectively. SDM solutions exhibited a cloudy, white appearance post 24 hours indicative of drug precipitation. DLS data also showed aggregate formation (data not shown). MDMs with PTX and 17-AAG were more stable against precipitation than SDM with PTX alone over a 24 hour period (FIG. 2), noting drug retention of approximately 97% (Table 3-2). DCTX/17-AAG and ETO/17-AAG have similar results for stability and drug retention within the micelle of approximately 96% and 94% respectively (Table 3-2). At 24 hours these MDM solutions were visually clear and DLS data confirmed the particle size, remained between 30 and 40 nm (data not shown). In the 3-drug combination, MDM of PTX/ETO/17-AAG was stable for 24 hours (FIG. 2). Drug loading data indicated that all drugs were retained above 97% of their initial loading value at 24 hours. MDM solutions were visually clear and particle size did not change significantly at 24 hours (data not shown).

$^1$H NMR spectroscopy of SDM and MDM. $^1$H NMR measurements were used to confirm the incorporation of drugs into PEG-b-PLA micelles. $^1$H NMR spectra in DMSO-$d_6$ for individual drugs and drug combinations showed all the prominent resonance peaks representative of the drug(s) and those of PLA and PEG blocks. In contrast, only the PEG resonance peaks were detected in $D_2O$ while PLA and drug(s) resonance peaks were absent due to the restricted mobility of the PLA and drug(s) molecules within the core of the micelle which is indicative of drug(s) incorporation into PEG-b-PLA micelles. PEG-b-PLA was identified by proton resonances at 3.4-3.6 ppm from ethylene oxide of the PEG group and the proton resonances at 5.0-5.1 for the lactic acid group. 17-AAG was identified by proton resonance at 0.7 ppm for the methyl groups. PTX was identified by proton resonances at 1.0 ppm for its methyl groups at C16 and C17. Lastly, ETO was identified by proton resonances between 6 and 7 ppm for the aromatic protons of the benzene rings.

In vitro Release Profiles of Drug(s) from SDM and MDM. Drug release data from SDM containing 17-AAG, ETO showed that over 90% of the drug was released from PEG-b-PLA micelle in 6 hours (FIG. 3A). Over 90% of DCTX was released from SDM in 9 hours (FIG. 3A). Rapid precipitation of PTX from the SDM during the dialysis experiment precluded garnering of any meaningful data. MDM containing PTX and 17-AAG showed over 72% PTX release in 24 hours while more than 90% of 17-AAG was released in 9 hours (FIG. 3B). MDM containing ETO and 17-AAG showed over 90% drug release in 6 and 9 hours, respectively (FIG. 3C). MDM containing DCTX and 17-AAG showed over 90% release in 12 and 9 hours, respectively (FIG. 3D).

MDM containing the three-drug combination of PTX/ETO/17-AAG showed approximately 80% release of PTX in 24 hours and over 90% release for ETO and 17-AAG in 6 and 9 hours, respectively (FIG. 3E). The in vitro drug release data was curve fitted using one phase exponential association (GraphPad Prism). The first-order rate constant derived from the curve fitting was used to calculate the $t_{1/2}$ of the drug release from PEG-b-PLA micelles. The data for the SDM and MDM is presented in Table 3-3 along with the goodness of fit and log oil-in water partition coefficient values for all drugs. The data in Table 3-3 lists the first-order rate constants and the $t_{1/2}$ values for all SDM and MDM except for SDM with PTX. This again was due to the rapid precipitation of PTX from the SDM during drug release test, which precluded the possibility of garnering any useful data.

TABLE 3-3

Parameters For In Vitro Drug Release from PEG-B-PLA Micelles (Single
Agent, 2- Or 3-Drug Combinations): Curve Fitting of In Vitro Drug(s)
Release from SDM and MDM (n = 4, mean ± SD).

| Anticancer agent | first-order rate constant (hr$^{-1}$) | $t_{1/2}$ (hr) | goodness of fit ($r^2$) | log p$^{(1)}$ |
|---|---|---|---|---|
| Paclitaxel | — | — | — | 3.0 |
| Docetaxel | 0.379 | 1.83 | 0.993 | 2.4 |
| 17-AAG | 0.525 | 1.32 | 0.999 | 1.3 |
| Etoposide | 0.636 | 1.09 | 0.999 | 1.0 |
| Paclitaxel | 0.138 | 5.01 | 0.938 | 3.0 |
| 17-AAG | 0.398 | 1.74 | 0.996 | 1.3 |
| Docetaxel | 0.288 | 2.41 | 0.996 | 2.4 |
| 17-AAG | 0.375 | 1.85 | 0.996 | 1.3 |
| 17-AAG | 0.414 | 1.67 | 0.997 | 1.3 |
| Etoposide | 0.657 | 1.06 | 0.997 | 1.0 |
| Paclitaxel | 0.136 | 5.10 | 0.973 | 3.0 |
| 17-AAG | 0.386 | 1.80 | 0.995 | 1.3 |
| Etoposide | 0.785 | 0.88 | 0.992 | 1.0 |

$^{(1)}$Calculated from XLog P ver2.0 (http://pubchem.ncbi.nlm.nih.gov/). (Curve-fitted with Graphic Prism v4.03)

Discussion. PEG-b-PLA micelles were able to successfully solubilize all chemotherapeutic agents alone or in combination with other drugs at clinically relevant levels. Given the toxicity associated with common formulation vehicles used, like CrEL, ethanol, DMSO and Tween 80 to name a few, this formulation provides a safer and less toxic alternative. Additionally, the presence of multiple drugs within the same micelles did not adversely affect the solubility enhancement achieved by individual drugs. This is due to the high loading capacity of PEG-b-PLA micelles as seen by the increasing % w/w contributions of the drug in forming these micelles. This allows for combination chemotherapy within one carrier system, which has not been previously attempted due to solubility and stability issues.

Initial solubility studies have indicated that PEG-b-PLA micelles have the capacity to solubilize multiple drugs allowing for concomitant delivery of potentially synergistic chemotherapeutic combinations without the attendant clinical issues currently seen while using multiple drug regimens. The stability of these formulations was also evaluated using optical density measurements coupled with HPLC and DLS. Assessing the stability of PEG-b-PLA micelles is crucial to determine if the formulation is stable long enough for handling and IV administration. As the data shows, the SDMs are stable for at least 6 hours while the 17-AAG micelles were stable for 24 hours. The two-drug MDM combinations showed greater stability. The presence of 17-AAG in these micelles helps stabilize the formulation and confers greater stability of the chemotherapeutic agents at the same level of solubilization as seen with the SDM.

All two-drug MDM combinations retained over 94% of their drug loading at 24 hours. The three-drug combination MDM showed the highest degree of stability at 24 hours with over 97% of drug loaded being retained. For all PEG-b-PLA micelles that were stable at 24 hours there was no significant shift in their size as determined by DLS. The stability data is extremely promising and indicates that these MDM formulations are able to deliver clinically relevant doses of their chemotherapeutic agents in a clinically relevant time frame.

The formation of micelles and the localization of the drug(s) within the micellar core was confirmed using $^1$H NMR spectroscopy. The $^1$H NMR spectrum clearly showed the proton resonances for all drugs and PEG-b-PLA in DMSO-$d_6$. In contrast, the $^1$H NMR spectrum had suppressed proton resonances for the PLA block and drugs with only the PEG block peaks clearly visible. The presence of the drug(s) within the micelle core restricts the mobility of the drug(s) molecules and results in a loss of drug proton resonances.

Characterization of the in vitro release kinetics of chemotherapy of individual drugs and combinations for PEG-b-PLA micelles is important to assess the stability and release pattern of the drug(s) from the micelle under sink conditions. The in vitro release of 17-AAG from PEG-b-PLA micelles was fairly rapid (on the scale of a few hours), consistent with a low impact of PEG-b-PLA micelles on the PK of 17-AAG in rats. In vitro release of DCTX, ETO, or 17-AAG from PEG-b-PLA micelles spanned several hours with $t_{1/2}$ ranging from 1.09 hours for ETO, 1.32 hours for 17-AAG, and 1.83 hours for DCTX (FIG. 3), corresponding well with the oil/water partition coefficients of anticancer agents (Table 3-3). PTX precipitated during release from PEG-b-PLA micelles, preventing an estimation of $t_{1/2}$.

Figure 3:
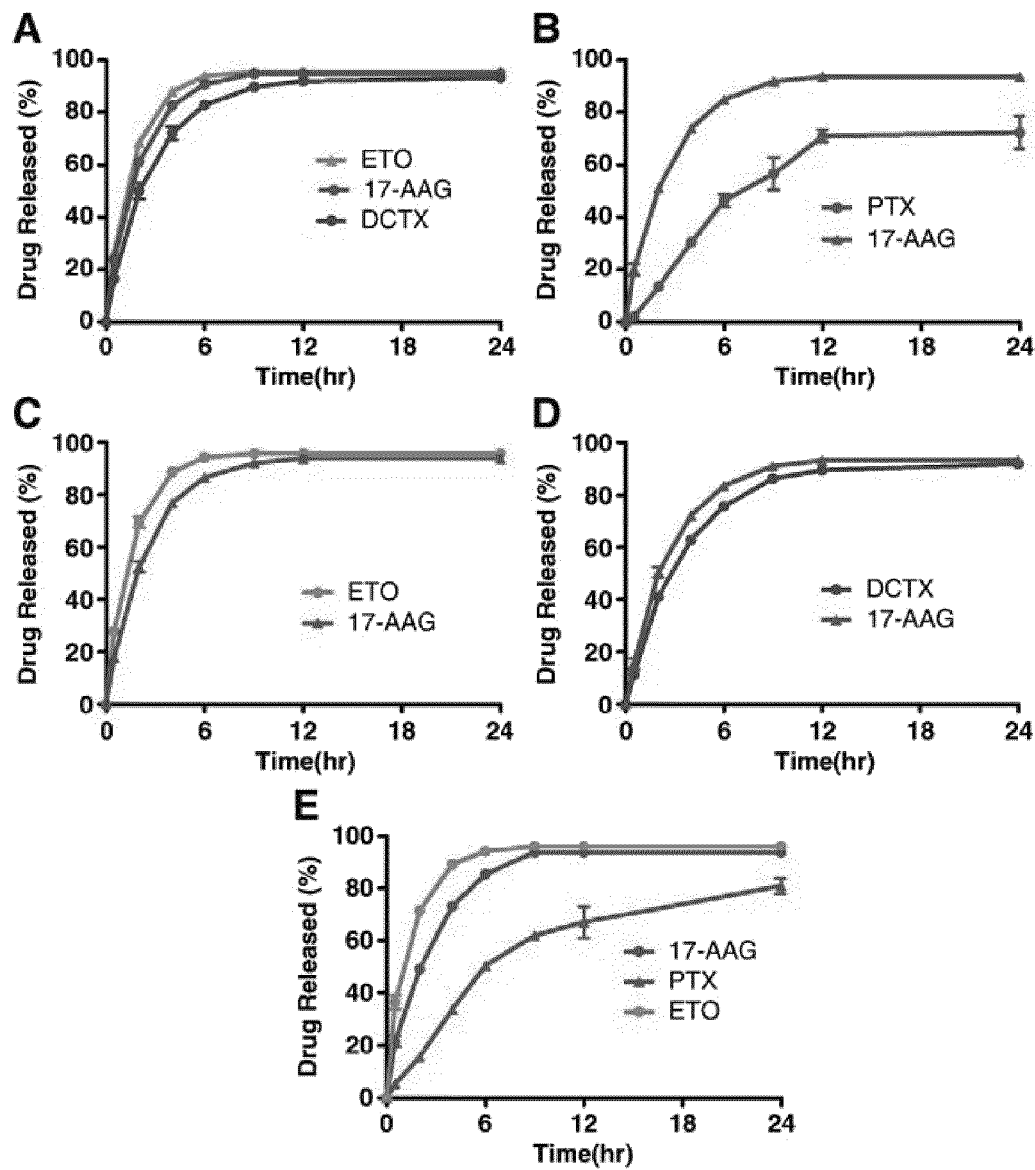
FIG. 3 illustrates in vitro drug release kinetics of (A) SDM containing ETO, DCTX or 17-AAG, (B) MDM with PTX/

For 2-drug combinations, release of 17-AAG is faster than PTX and DCTX and slower than ETO, which has the lowest log P (FIG. 3 and Table 3-3). For the 3-drug combination, $t_{1/2}$ values for ETO, 17-AAG, and PTX are 0.88, 1.80, and 5.10 hours, respectively, for PEG-b-PLA micelles (FIG. 3E), corresponding well with the oil/water partition coefficients of these anticancer agents.

A surprising phenomenon seen with all the two-drug and these combinations is the ability of 17-AAG to stabilize PEG-b-PLA micelles. This phenomenon is starkly evidenced by the stability of PTX in the two-drug and three-drug combinations, while itself being prone precipitation in the SDM formulation. The novel finding of ability of 17-AAG to maintain the stability of PTX and other hydrophobic drugs in PEG-b-PLA micelles for at least 24 hours will allow for these formulations to be suitable for administration to humans by IV or infusion in combination chemotherapeutic carriers.

Another facet of the in vitro release kinetics indicates that variation between the release of anticancer agents from the micelles is diffusion-controlled and not due to the break down of PEG-b-PLA micelles, where drug release kinetics are expected to be similar for the two- and three-drug combinations. However, $t_{1/2}$ values for PEG-b-PLA micelles indicate that drug release will be fairly rapid and comparable in vivo, owing to lower stability of PEG-b-PLA micelles in the presence of serum proteins, specifically α- and β-globulins.

PEG-b-PLA micelles filled with a pair of fluorescent probes, DiIC18 and DiOC18, lose fluorescence resonance energy transfer after IV injection within 15 minutes, indicating rapid release of DiIC18 and DiOC18 in vivo. As it turns out, α- and β-globulins induce a rapid loss of fluorescence energy transfer of DiIC18 and DiOC18 for PEG-b-PLA micelles in vitro as well, potentially due to disruption of PEG-b-PLA micelles. These results indicate that PEG-b-PLA micelles will release pairs of chemotherapy and 17-AAG within 1 hour in vivo due to a loss of integrity, caused by α- and β-globulins, although effects of dilution and other components in blood must also be considered. The nature of these results will be tested in cancer cell lines to determine cytotoxic concentrations for these combinations. This will allow for further determine if any additive and/or synergistic effects are seen with these combinations. Murine tumor models determine whether concurrent combination drug release from PEG-b-PLA micelles may provide linear PKs for PTX and 17-AAG and synergistic anti-tumor efficacy given higher maximum tolerated doses in comparison to DMSO/lipid and CrEL.

In summary, current chemotherapeutic agents in clinical and preclinical situations require dosing with harsh excipients that can cause severe formulation related side effects. Stability concerns create issues with administering combination chemotherapy simultaneously. The formulations described herein using PEG-PLA offer novel alternatives to the current commercial formulations. This example demonstrated the successful combination of up to three chemotherapeutic agents in one carrier system at clinically relevant concentrations, with 24 hour stability. Another important find is the ability of 17-AAG to maintain stability of different hydrophobic drugs in the carrier system for 24 hours.

Example 4

Polymeric Micelles for Nano-Combination Drug Delivery

PEG-b-PLA micelles can serve as a platform nanotechnology for the delivery of two or more poorly water-soluble anti-cancer agents, to provide simple, safe, and synergistic combination cancer therapies. Polymeric micelles are nanoscopic vehicles for cancer drug delivery that have gained attention due to proven safety and progress in drug solubilization relative to Cremophor EL (CrEL), a commonly used surfactant that exerts toxicity, especially when it is used for poorly water-soluble chemotherapy, e.g. paclitaxel (Taxol®). CrEL-induced hypersensitivity reactions cause discontinuation of drug therapy and death despite pre-medication with steroids. CrEL micelles cause pharmacokinetic (PK) interactions for poorly water-soluble anti-cancer agents due to drug entrapment, raising risks of non-linear PK and reduced tumor accumulation of anti-cancer agents.

PEG-b-PLA assembles into nanoscopic micelles that raise the water solubility of paclitaxel from 1.0 mg/L to 5.0 mg/mL (Genexol®). PEG-b-PLA is much less toxic than CrEL, increases the maximum tolerated dose (MTD) of paclitaxel, and increases tumor localization in murine tumor models due to increased dose and apparent linear PK profile. As a result, PEG-b-PLA micelles enhance the anti-tumor efficacy of paclitaxel in phase I/II clinical trials. Many obstacles facing development, scale-up, and safety constraints have been met by this drug delivery nanotechnology.

It has been discovered that PEG-b-PLA micelles can take up and solubilize multiple anti-cancer agents, providing a novel and simple approach for combination cancer therapy, to provide synergistic anti-tumor efficacy involving combinations of chemo-therapy and signal transduction inhibitors. This Example provides novel 3-drug anti-cancer combination involving paclitaxel, rapamycin, and 17-allylamino-17AAG. Pre-clinical data indicate that paclitaxel exerts synergistic anti-tumor activity in murine tumor models with rapamycin or 17-AAG. While acting via different mechanisms of action and on different targets, both rapamycin and 17-AAG act on cancer survival pathways and are potent angiogenesis inhibitors. Notably, 17-AAG, a prototype heat shock protein 90 (Hsp90) inhibitor, knocks out kinases (AKT, Raf), activated by the inhibition of the mammalian target of rapamycin (mTOR) by a feed-back mechanism, providing a basis for enhancing the activity of rapamycin, the first mTOR inhibitor.

In this Example, PEG-b-PLA micelles solubilize paclitaxel, rapamycin, and 17-AAG as nano-combinations, offering safety over CrEL and cosolvents, physical stability against drug precipitation, ease of production and scale-up, and low prospects for PK interactions. Each of these aspects facilitate the ease of entry into clinical trials for a 3-drug combination of paclitaxel, rapamycin, and 17-AAG.

Experimental Methods. Paclitaxel, rapamycin, 17-AAG (2.0 mg), and PEG-b-PLA (15 mg) were dissolved in acetonitrile (ACN) (0.50 mL) in a round bottom flask. $M_n$ of PEG and PLA of PEG-b-PLA was 4,200 and 1,900 g/mol, respectively (APC Inc., UK). ACN was removed by heating at 60° C. and reduced pressure. The resultant dry polymer film containing anti-cancer agent(s) was dissolved by addition of water (0.50 mL) at 60° C. with gentle agitation. The aqueous solution containing PEG-b-PLA micelles filled paclitaxel, rapamycin, 17-AAG or their combinations was centrifuged, filtered (0.45 μm), and subject to reverse-phase HPLC and dynamic light scattering (DLS) size analysis (Zetasizer, Malvern, UK). In vitro drug release experiments for PEG-b-PLA micelles and related 2- or 3-drug combinations are described in Example 3 above.

Results And Discussion. Anti-cancer agents in preclinical development, e.g. 17-AAG, and many in clinical practice, e.g. paclitaxel, rapamycin, are poorly water-soluble and require safe vehicles for drug solubilization and intravenous (IV) infusion. However, vehicles for IV drug infusion are often toxic, e.g. CrEL, and hamper progress in therapy involving multiple poorly water-soluble anti-cancer agents due to a risk of precipitation and additive/synergistic toxicity caused by two or more vehicles for drug solubilization, e.g. CrEL for paclitaxel in Taxol® and DMSO/lipid for 17-AAG in recent clinical trials.

PEG-b-PLA assembles into micelles that solubilize paclitaxel, rapamycin, and 17-AAG at mg/mL levels without CrEL or co-solvents, e.g., DMSO/lipid (Table 4-1). Anti-cancer agents require mg/mL levels in aqueous vehicles for IV infusion for cancer therapy. The percent drug loading (wt/wt) for PEG-b-PLA micelles increases from 1 to 2- to 3-drug combinations without a major change in particle size, noting a constant level of PEG-b-PLA in this drug solubilization experiment.

TABLE 4-1

One-, 2-, and 3-drug solubilization by PEG-b-PLA micelles (n = 3, mean ± SD).

| Anticancer Agent | Drug level in water (mg/mL) | % Drug loading (wt drug(s)/wt polymer) | PEG-b-PLA micelle diameter (nm ± SD) |
|---|---|---|---|
| Paclitaxel | 3.54 ± 0.32 | 10.3 ± 0.9 | 38.8 ± 0.6 |
| Rapamycin | 1.84 ± 0.26 | 6.6 ± 1.3 | 36.9 ± 1.3 |
| 17-AAG | 3.90 ± 0.28 | 11.3 ± 0.3 | 39.3 ± 2.9 |
| Paclitaxel + Rapamycin | 3.49 ± 0.14 / 0.76 ± 0.31 | 22.6 ± 0.9 | 43.0 ± 2.4 |
| Paclitaxel + 17-AAG | 3.92 ± 0.17 / 3.88 ± 0.29 | 25.9 ± 1.6 | 38.9 ± 1.1 |
| Rapamycin + 17-AAG | 1.83 ± 0.25 / 4.02 ± 0.14 | 22.6 ± 1.6 | 39.4 ± 1.9 |
| Paclitaxel + Rapamycin + 17-AAG | 3.36 ± 0.46 / 2.05 ± 0.08 / 3.86 ± 0.46 | 40.2 ± 1.2 | 43.8 ± 1.3 |

As 2-drug combinations (paclitaxel/rapamycin, paclitaxel/17-AAG, rapamycin/17-AAG), PEG-b-PLA micelles have a percent drug loading at about 20%. As a 3-drug combination of paclitaxel, rapamycin, and 17-AAG, PEG-b-PLA micelles have an inordinately high percent drug loading of 40% with a slight increase in size, about 44 nm, relative to empty PEG-b-PLA micelles (38 nm). With respect to stability against drug precipitation, light scattering studies on PEG-b-PLA micelles show that the 2- and 3-drug combinations are more stable in water than paclitaxel alone over 24 hours, due to drug interaction in cores of PEG-b-PLA micelles.

The results for the in vitro release of 1-, 2-, and 3-drugs from PEG-b-PLA micelles have been compiled in Table 4-2. Release of the anti-cancer agents from PEG-b-PLA micelles occurs over about one day, and it appears to correlate with the logarithm of the oil/water partition coefficient of anticancer agent (log P). Drug release for 2- and 3-drug combinations for PEG-b-PLA micelles mirrors the kinetics of single anti-cancer agent release (Table 4-2 and FIG. 4). However, co-loaded rapamycin in PEG-b-PLA micelles slows the release of paclitaxel and 17-AAG, especially in the 3-drug combination. The half-life ($t_{1/2}$) for paclitaxel and 17-AAG is 10.1 and 2.86 hours, respectively. In this case, rapamycin has a very long $t_{1/2}$ of 18.6 hours.

TABLE 4-2

1-, 2-, and 3-drug release from PEG-b-PLA micelles (n = 4, mean ± SD).

| Anticancer agent | first-order rate constant (hr$^{-1}$) | $t_{1/2}$ (hr) | log P |
|---|---|---|---|
| Paclitaxel | —* | —* | 3.0 |
| Rapamycin | 0.100 | 6.93 | 5.8 |
| 17-AAG | 0.525 | 1.32 | 1.3 |
| Paclitaxel + rapamycin | 0.116 / 0.070 | 5.98 / 10.04 | 3.0 / 5.8 |
| Paclitaxel + 17-AAG | 0.138 / 0.398 | 5.01 / 1.74 | 3.0 / 1.3 |
| Rapamycin + 17-AAG | 0.068 / 0.330 | 9.99 / 2.10 | 5.8 / 1.3 |
| Paclitaxel + Rapamycin + 17-AAG | 0.068 / 0.037 / 0.242 | 10.13 / 18.59 / 2.86 | 3.0 / 5.8 / 1.3 |

*Paclitaxel precipitates in the dialysis bag during drug release, preventing calculation of a first-order constant and $t_{1/2}$.

While differences in drug release profiles emerge in vitro between anti-cancer agents for PEG-b-PLA micelles and between related 2- and 3-drug combinations, these differences will be low in vivo due to the destabilizing effect of serum proteins on the integrity of PEG-b-PLA micelles, especially α- and β-globulins. As a result, in vivo drug release for PEG-b-PLA micelles will be rapid for 2- and 3-drug combinations, minimizing risk for PK interactions due to drug entrapment in micelles, which has been noted for CrEL and poorly water-soluble anti-cancer agents.

In summary, PEG-b-PLA micelles effectively solubilize combinations of paclitaxel, rapamycin, and 17-AAG for IV infusion without the requirement of CrEL or co-solvents, such as DMSO/lipid. In this Example, synergistic 2- and 3-drug combinations of paclitaxel, rapamycin, and 17-AAG are easily obtained via PEG-b-PLA micelles. The unprecedented 3-drug combination of paclitaxel, rapamycin, and 17-AAG will provide useful solutions to current clinical problems in cancer therapy.

Example 5

Additional Data of Polymeric Micelles for Nano-Combination Drug Delivery

The PEG-b-PLA drug-containing micelles can load and deliver the poorly water soluble drugs paclitaxel, rapamycin, and 17-AAG, at clinically relevant doses, as indicated by the data of Tables 5-1 to 5-5 and FIGS. 3, and 5-9.

PEG-b-PLA in combination with certain hydrophobic drugs has significant solubilizing and stabilizing properties. FIG. 5 illustrates data from the solubilization of paclitaxel, docetaxel, rapamycin, 17-AAG, and 2- or 3-combinations (chemo+17-AAG) by PEG-b-PLA micelles (4.2K:1.9K) in water; n=3, Mean. Additional data for these micelle formulations is shown in Tables 5-1, 5-2, 5-3, and 5-4.

TABLE 5-1

Drug solubilization results for PEG-PLA micelles (n = 3, Mean ± SD).

| Anticancer agent | drug level in water (mg/mL) | % drug loading (wt. drug(s)/ wt. polymer) | PEG-b-PLA micelle diameter (nm ± SD) |
|---|---|---|---|
| Rapamycin | 1.84 ± 0.26 | 6.6 ± 1.3 | 36.9 ± 1.3 |
| Paclitaxel | 3.54 ± 0.32 | 10.3 ± 0.9 | 38.8 ± 0.6 |
| Docetaxel | 4.27 ± 0.44 | 11.5 ± 0.5 | 37.3 ± 1.7 |
| 17-AAG | 3.90 ± 0.28 | 11.3 ± 0.3 | 39.3 ± 2.9 |
| Paclitaxel | 3.92 ± 0.17 | 25.9 ± 1.6 | 38.9 ± 1.1 |
| 17-AAG | 3.88 ± 0.29 | | |
| Docetaxel | 4.62 ± 0.44 | 25.8 ± 2.2 | 39.0 ± 0.8 |
| 17-AAG | 4.01 ± 0.08 | | |

TABLE 5-2

Combination drug solubilization results for PEG-b-PLA micelles (n = 3, Mean ± SD).

| Anticancer agent | drug level in water (mg/mL) | % drug loading (wt. drug(s)/ wt. polymer) | PEG-b-PLA micelle diameter (nm ± SD) |
|---|---|---|---|
| Rapamycin | 1.06 ± 0.07 | 13.3 ± 0.3 | 41.0 ± 1.5 |
| Paclitaxel | 3.59 ± 0.09 | | |
| Rapamycin | 2.43 ± 0.11 | 16.6 ± 1.0 | 38.1 ± 0.9 |
| Docetaxel | 3.01 ± 0.26 | | |
| Rapamycin | 1.83 ± 0.25 | 22.6 ± 1.6 | 39.4 ± 1.9 |
| 17-AAG | 4.02 ± 0.14 | | |
| Rapamycin | 2.09 ± 0.08 | 40.4 ± 1.2 | 43.8 ± 1.3 |
| Paclitaxel | 3.36 ± 0.46 | | |
| 17-AAG | 3.86 ± 0.46 | | |
| Rapamycin | 2.34 ± 0.19 | 33.3 ± 1.3 | 42.5 ± 1.3 |
| Docetaxel | 2.71 ± 0.07 | | |
| 17-AAG | 4.06 ± 0.17 | | |

TABLE 5-3

Drug loss from PEG-b-PLA micelles after 24 hours (reverse phase-HPLC).

| Anticancer agent | initial drug level in water (mg/mL) | drug level @ 24 hr in water (mg/mL) | % w/w drug(s) left @ 24 hr |
|---|---|---|---|
| Rapamycin | 1.84 ± 0.26 | 1.68 ± 0.23 | 91.5 ± 0.2 |
| Paclitaxel | 3.54 ± 0.32 | 0.57 ± 0.07 | 16.2 ± 1.0 |
| Docetaxel | 4.27 ± 0.44 | 1.14 ± 0.03 | 26.8 ± 3.3 |
| 17-AAG | 3.90 ± 0.28 | 3.84 ± 0.18 | 98.6 ± 2.4 |
| Paclitaxel | 3.92 ± 0.17 | 3.86 ± 0.15 | 98.5 ± 0.3 |
| 17-AAG | 3.88 ± 0.29 | 3.77 ± 0.28 | 96.9 ± 0.2 |
| Docetaxel | 4.62 ± 0.44 | 4.45 ± 0.13 | 96.3 ± 1.8 |
| 17-AAG | 4.01 ± 0.08 | 3.83 ± 0.17 | 95.5 ± 2.7 |

TABLE 5-4

Drug loss from PEG-b-PLA micelles after 24 hours (reverse phase-HPLC).

| Anticancer agent | initial drug level in water (mg/mL) | drug level @ 24 hr in water (mg/mL) | % w/w drug(s) left @ 24 hr |
|---|---|---|---|
| Rapamycin | 1.06 ± 0.07 | 1.02 ± 0.06 | 96.0 ± 0.4 |
| Paclitaxel | 3.59 ± 0.09 | 3.44 ± 0.04 | 95.9 ± 2.0 |
| Rapamycin | 2.43 ± 0.11 | 2.28 ± 0.10 | 93.8 ± 0.8 |
| Docetaxel | 3.01 ± 0.26 | 2.83 ± 0.24 | 94.0 ± 0.3 |
| Rapamycin | 1.83 ± 0.25 | 1.71 ± 0.29 | 93.0 ± 3.9 |
| 17-AAG | 4.02 ± 0.14 | 3.77 ± 0.17 | 93.8 ± 4.1 |
| Rapamycin | 2.09 ± 0.11 | 2.05 ± 0.08 | 97.8 ± 2.1 |
| Paclitaxel | 3.36 ± 0.46 | 3.29 ± 0.47 | 97.9 ± 2.3 |
| 17-AAG | 3.86 ± 0.36 | 3.74 ± 0.44 | 96.7 ± 2.5 |
| Rapamycin | 2.34 ± 0.19 | 2.32 ± 0.17 | 99.5 ± 2.3 |
| Docetaxel | 2.71 ± 0.07 | 2.67 ± 0.03 | 98.6 ± 2.6 |
| 17-AAG | 4.06 ± 0.17 | 4.03 ± 0.25 | 99.3 ± 2.2 |

Parameters and data for in vitro drug release from PEG-b-PLA micelles (single agent, 2- or 3-drug combinations) are shown in Table 5-5 and in FIGS. 3 and 6-9. FIG. 6 illustrates data from the in vitro release of paclitaxel, docetaxel, rapamycin or 17-AAG from PEG-b-PLA micelles (12.5 mM PBS, pH=7.4, 37° C.); (n=4, Mean±SD). The low release of paclitaxel is a result of the drug crashing out of the dialysis bag used in Preparatory Process C, used for preparing these micelles.

FIG. 3B illustrates data from the in vitro combination release of paclitaxel and 17-AAG from PEG-b-PLA micelles (12.5 mM PBS, pH=7.4, 37° C.; (n=4, Mean±SD). FIG. 7 illustrates data from the in vitro combination release of rapamycin and 17-AAG from PEG-b-PLA micelles (12.5 mM PBS, pH=7.4, 37° C.; (n=4, Mean±SD). FIG. 8 illustrates data from the in vitro combination release of rapamycin, docetaxel & 17-AAG from PEG-b-PLA micelles (12.5 mM PBS, pH=7.4, 37° C.); (n=4, Mean±SD). FIG. 9 illustrates half life parameters (A) for in vitro rapamycin release; and (B) for in vitro 17-AAG release, from PEG-b-PLA micelles (single agent, 2- or 3-drug combinations). Calculated from X log P ver2.0 (http://pubchem.ncbi.nlm.nih.gov/); curve-fitted with Graphic Prism v4.03.

TABLE 5-5

Parameters for in vitro drug release from PEG-b-PLA micelles (single agent, 2-or 3-drug combinations).

| Anticancer agent | first-order rate constant (hr$^{-1}$) | $t_{1/2}$ (hr) | goodness of fit ($r^2$) | log P[1] |
|---|---|---|---|---|
| Paclitaxel | — | — | — | 3.0 |
| 17-AAG | 0.525 | 1.32 | 0.999 | 1.3 |
| Rapamycin | 0.081 | 8.52 | 0.990 | 5.8 |
| Paclitaxel | 0.138 | 5.01 | 0.938 | 3.0 |

TABLE 5-5-continued

Parameters for in vitro drug release from PEG-b-PLA micelles (single agent, 2-or 3-drug combinations).

| Anticancer agent | first-order rate constant (hr$^{-1}$) | t$_{1/2}$ (hr) | goodness of fit (r$^2$) | log P$^{(1)}$ |
|---|---|---|---|---|
| 17-AAG | 0.398 | 1.74 | 0.996 | 1.3 |
| Rapamycin | 0.069 | 10.05 | 0.991 | 5.8 |
| Paclitaxel | 0.116 | 6.00 | 0.993 | 3.0 |
| Rapamycin | 0.085 | 8.12 | 0.993 | 5.8 |
| Docetaxel | 0.317 | 2.19 | 0.999 | 2.4 |
| Rapamycin | 0.079 | 8.73 | 0.983 | 5.8 |
| 17-AAG | 0.385 | 1.80 | 0.999 | 1.3 |
| Rapamycin | 0.050 | 13.93 | 0.979 | 5.8 |
| Paclitaxel | 0.075 | 9.20 | 0.984 | 3.0 |
| 17-AAG | 0.275 | 2.52 | 0.996 | 1.3 |
| Rapamycin | 0.069 | 10.00 | 0.982 | 5.8 |
| Docetaxel | 0.306 | 2.26 | 0.993 | 2.4 |
| 17-AAG | 0.363 | 1.91 | 0.995 | 1.3 |

$^{(1)}$Calculated from XlogP ver2.0 (http://pubchem.ncbi.nlm.nih.gov/); curve-fit with Graphic Prism v4.03.

Conclusions. PEG-b-PLA micelles solubilize paclitaxel, docetaxel, 17-AAG, or rapamycin at mg/mL levels in water. PEG-b-PLA micelles solubilize 2-drug combinations (paclitaxel/17-AAG, paclitaxel/rapamycin, or 17-AAG/rapamycin), reaching levels obtained for each single anti-cancer agent alone in PEG-b-PLA micelles. PEG-b-PLA micelles solubilize a 3-drug combination of paclitaxel, 17-AAG and rapamycin, reaching levels obtained for each single anticancer agent alone in PEG-b-PLA micelles. The t$_{1/2}$ values for the in vitro release of paclitaxel, 17-AAG and rapamycin from PEG-b-PLA micelles as 1-drug or 2- or 3-drug combinations are on the scale of several hours, increasing with log P values.

Example 6

Polymer Micelles for Multiple Drug Delivery

Polymer micelles have attracted attention in drug delivery due to proven safety and rapid progress in drug solubilization, especially in the field of cancer therapy. Poly(ethylene glycol)-block-poly(lactic acid) (PEG-b-PLA) micelles have entered phase II clinical trials in the USA and have gained approval in Korea as a vehicle for paclitaxel (Genexol-PM®), offering a safer vehicle for this poorly water-soluble cancer drug over Cremophor EL (Taxol®). Cremophor EL causes severe toxicities, including acute hypersensitivity reactions despite pre-medication (Sparreboom et al., *J. Clin. Oncol.* 2005, 23, 7765). The maximum tolerated dose (MTD) of Genexol-PM® in a phase I clinical trial was 300 mg/m$^2$, whereas the MTD for Taxol® is only 135 to 200 mg/m$^2$ (Kim et al., *Clin. Cancer Res.* 2004, 10, 3708).

17-AAG inhibits heat shock protein 90 (Hsp90), which acts as a chaperone for "client proteins," many of which are involved in cancer-causing and survival pathways (Banerji, *Clin. Cancer Res.* 2009, 15, 9). Rapamycin inhibits mTOR, a serine-threonine kinase, which plays a central role in cell growth, proliferation, survival and angiogenesis (Lopiccolo et al., *Drug Resist. Updates* 2008, 11, 32). Two-drug combinations of paclitaxel+17-AAG and paclitaxel+a slightly water soluble analogue of rapamycin (CCI-779) are in clinical trials, but require Cremophor EL, DMSO/lipid and/or ethanol as vehicles for drug solubilization.

The example demonstrates that PEG-b-PLA micelles can encapsulate and thereby solubilize multiple cancer drugs in an aqueous solution. The PEG-b-PLA micelles have been shown to effectively solubilize, for example, paclitaxel, docetaxel, etoposide, rapamycin, and 17-allylamino-17-desmethoxygeldanamycin (17-AAG). The following disclosure describes methodology for the preparation of multiple drug loaded PEG-b-PLA micelles, cytotoxicity experiments, combination index analysis, as well as discussion of the results.

Reagents. PEG-b-PLA (Mn of PEG and PLA were 4,200 and 1,900 g/mol, respectively; PDI=1.05) was purchased from Advanced Polymer Materials Inc. (Montreal, CAN). Paclitaxel was obtained from LKT Laboratories Inc. (St. Paul, Minn.). 17-AAG and rapamycin were purchased from LC Laboratories (Woburn, Mass.). All other reagents were obtained from Fisher Scientific Inc. (Fairlawn, N.J.).

Preparation of Multiple Drug Loaded PEG-b-PLA Micelles. Paclitaxel (2.0 mg), 17-AAG (2.0 mg), rapamycin (1.5 mg) and PEG-b-PLA (15 mg) were dissolved in acetonitrile (0.50 mL) in a round bottom flask, and the acetonitrile was removed by heating at 60° C. under reduced pressure via a rotary-evaporator. The resultant dry PEG-b-PLA film containing drugs was dissolved by the addition of water (0.50 mL) at 60° C. with gentle agitation. The aqueous solution of PEG-b-PLA micelles filled with paclitaxel, 17-AAG and rapamycin was centrifuged, filtered (0.45 µm) and subjected to reverse-phase HPLC (Shimadzu, JP) and dynamic light scattering analyses (Zetasizer, Malvern, UK). See FIG. 12.

In vitro Cytotoxicity Experiments. MCF-7 human breast cancer cells were cultured in DMEM medium while 4T1 murine breast cancer cells, A549 human non-small cell lung cancer cells, and LS180 human colon cancer cells were cultured in RPMI1640 medium. Both media were supplemented with 10% fetal bovine serum (FBS) with antibiotics under 5% $CO_2$ and 37° C. in an incubator. Cells (3-5×10$^3$) were seeded into 96 well plates and incubated for 24 hours before drug exposure. Free drugs were dissolved in DMSO, and drug-loaded PEG-b-PLA micelles were in deionized water. The samples were diluted with cell culture media to make 0.10, 1.0, 10, 100 and 1000 nM in 96 well plates. After incubation for 72 hours, cell culture media was replaced with fresh media, and 20 µL of resazurin dye solution (AlamarBlue®, Invitrogen, USA) was added into the wells. The metabolic conversion of resazurin dye by each viable cancer cell was quantified using a fluorescence cell plate reader (SpectraMax M2, Molecular Devices, USA) to estimate cell viability. Growth inhibition curves for paclitaxel, 17-AAG, rapamycin and their combinations were obtained by plotting the percentage of viable cells against drug concentration. IC$_{50}$ values of free drugs and drug-loaded PEG-b-PLA micelles were calculated based on median-effect equation using Compusyn software (ver. 1.0).

Combination Index Analysis. The combination index (CI) of 2- or 3-drug combinations was calculated based on Chou and Talalay method (Cancer Res; 70(2), 440-446; Jan. 15, 2010) using Compusyn software (ver. 1.0). CI values were obtained at IC$_{50}$ values for 2- or 3-drug combinations. CI<1, C=1, and CI>1 were used as criteria to determine whether 2- or 3-drug combinations are synergistic, additive, and antagonistic, respectively (FIGS. 13-20).

Discussion. PEG-b-PLA micelles have remarkable effects on the water solubility of paclitaxel, 17-AAG, rapamycin and their 2- and 3-drug combinations (Table 6-1). In each case, PEG-b-PLA micelles raise the water solubility of paclitaxel, 17-AAG and rapamycin from about mg/L levels to mg/mL levels, sufficient for cancer therapy. Remarkably, the individual drug levels when combined as 2- and 3-drug combinations mirror the level of each drug incorporated alone in PEG-b-PLA micelles (Table 6-1). In other words, % drug loading (wt. drug/wt. polymer) increases from 1 to 2- to 3-drug combinations without additional PEG-b-PLA, beyond the quantity used in single drug solubilization experiments. Thus, PEG-b-PLA micelles can be used to deliver a 3-drug combination of paclitaxel, 17-AAG and rapamycin at 3.36, 3.86 and 2.09 mg/mL, respectively, with only a slight increase in particle size.

TABLE 6-1

Combinatorial drug solubilization by PEG-b-PLA micelles (n = 3, mean ± SD).

| Anticancer agent | Drug level in water (mg/mL) | % drug loading wt. drug(s)/wt. polymer | PEG-b-PLA micelle dia. (nm ± SD) |
|---|---|---|---|
| Paclitaxel | 3.54 ± 0.32 | 10.3 ± 0.9 | 38.8 ± 0.6 |
| 17-AAG | 3.90 ± 0.28 | 11.3 ± 0.3 | 39.3 ± 2.9 |
| Rapamycin | 1.84 ± 0.26 | 6.6 ± 1.3 | 36.9 ± 1.3 |
| Paclitaxel + 17-AAG | 3.92 ± 0.17 / 3.88 ± 0.29 | 25.9 ± 1.6 | 38.9 ± 1.1 |
| Paclitaxel + Rapamycin | 3.59 ± 0.09 / 1.06 ± 0.07 | 13.3 ± 0.3 | 41.0 ± 1.5 |
| Paclitaxel + 17-AAG + Rapamycin | 3.36 ± 0.08 / 3.86 ± 0.46 / 2.09 ± 0.08 | 40.4 ± 1.2 | 43.8 ± 1.3 |

Additional characterization data for several micelle drug delivery formulations is provided in Table 6-2 below.

TABLE 6-2

Combinatorial Drug Solubilization Results for PEG-b-PLA Micelles.

| Anticancer agent | drug level in water (mg/mL) | % drug loading (wt. drug(s)/wt. polymer) | PEG-b-PLA micelle diameter (nm ± SD) |
|---|---|---|---|
| Rapamycin | 1.84 ± 0.26 | 6.6 ± 1.3 | 36.9 ± 1.3 |
| Paclitaxel | 3.54 ± 0.32 | 10.3 ± 0.9 | 38.8 ± 0.6 |
| Docetaxel | 4.27 ± 0.44 | 11.5 ± 0.5 | 37.3 ± 1.7 |
| 17-AAG | 3.90 ± 0.28 | 11.3 ± 0.3 | 39.3 ± 2.9 |
| Paclitaxel 17-AAG | 3.92 ± 0.17 / 3.88 ± 0.29 | 25.9 ± 1.6 | 38.9 ± 1.1 |
| Docetaxel 17-AAG | 4.62 ± 0.44 / 4.01 ± 0.08 | 25.8 ± 2.2 | 39.0 ± 0.8 |
| Rapamycin Paclitaxel | 1.06 ± 0.07 / 3.59 ± 0.09 | 13.3 ± 0.3 | 41.0 ± 1.5 |
| Rapamycin Docetaxel | 2.43 ± 0.11 / 3.01 ± 0.26 | 16.6 ± 1.0 | 38.1 ± 0.9 |
| Rapamycin 17-AAG | 1.83 ± 0.25 / 4.02 ± 0.14 | 22.6 ± 1.6 | 39.4 ± 1.9 |
| Rapamycin Paclitaxel 17-AAG | 2.09 ± 0.08 / 3.36 ± 0.46 / 3.86 ± 0.46 | 40.4 ± 1.2 | 43.8 ± 1.3 |
| Rapamycin Docetaxel 17-AAG | 2.34 ± 0.19 / 2.71 ± 0.07 / 4.06 ± 0.17 | 33.3 ± 1.3 | 42.5 ± 1.3 |

(n = 3, mean ± SD)

This increase in loading capacity is a surprising result that is uncommon in the field of drug solubilization. Particularly noteworthy is the 40% drug loading content for paclitaxel, 17-AAG and rapamycin in PEG-b-PLA micelles. Because PEG-b-PLA micelles have an excellent safety profile in humans, administration of 2- and 3-drug combinations of paclitaxel, 17-AAG and rapamycin via PEG-b-PLA micelles without Cremophor EL, DMSO/lipid and/or ethanol as vehicles for drug solubilization for multiple drug delivery by the intravenous route will be a valuable advance in cancer therapy.

Two-drug combinations of paclitaxel+17-AAG and paclitaxel+rapamycin have been proven to exert synergistic cancer activity in cell culture and in breast and lung murine tumor models, serving as a solid rationale for current clinical trials (Solit et al., Cancer Res. 2003, 63, 2139; Mondesire et al., Clin. Cancer Res. 2004, 10, 7031). More recently, the combination of 17-AAG+rapamycin has been proven to exert enhanced anti-proliferative activity in both MCF-7 and MDA-MB-231 breast cancer cells (Roforth and Tan, Anti-Cancer Drugs 2008, 19, 681), owing to a reduction in AKT activation and 17-AAG-induced suppression of the mitogen-activated protein kinase signaling pathway (RAS/RAF/MEK/ERK). It is believed that AKT activation due to mTOR inhibition by a negative feedback loop is a major reason that mTOR inhibitors have not been successful in clinical trials despite the central importance of the PI3K/AKT/mTOR pathway in cancer (e.g., activated in 60-70% of lung cancers) (Garber, JNCI 2009, 101, 288).

In the work described herein, paclitaxel+17-AAG, paclitaxel+rapamycin and 17-AAG+rapamycin dissolved with polymeric micelles exert additive or synergistic cancer activity against MCF-7 breast cancer cells, 4T1 breast cancer cells, A549 non-small cell lung cancer, and LS180 colon cancer, according CI analysis (FIGS. 14, 16, 18, and 20, and Tables 6-4 and 6-5). The 3-drug combination of paclitaxel, 17-AAG and rapamycin (5:1:1) has a very low $IC_{50}$ value of 114±10 nM versus 226±32 nM for paclitaxel alone in MCF-7 breast cancer cells. This 3-drug combination has a CI of 0.49±0.04 at the $IC_{50}$, indicating synergy in MCF-7 breast cancer cells. CI of 3 drug combination of paclitaxel, 17-AAG, and rapamycin was 0.04±0.001, 0.21±0.03, and 0.33±0.02 for 4T1 cells, A549 cells, and LS180 cells, respectively. It is noted that the PI3K/AKT/mTOR and RAS/RAF/MEK/ERK signaling pathways are aberrantly activated in many cancers, and there is evidence that they cooperate in promoting cancer cell survival (Grant, J. Clin. Invest. 2008, 118, 3003). Thus, the synergistic cytotoxicity of paclitaxel, 17-AAG and rapamycin possibly reflects the co-targeting of complementary signaling pathways by 17-AAG and rapamycin, enhancing the cytotoxicity of paclitaxel against MCF-7 breast cancer cells.

The cytotoxicity of paclitaxel, 17-AAG and rapamycin physically incorporated in PEG-b-PLA micelles is less than that of free drug(s) in cell culture. Nonetheless, evidence for synergy of paclitaxel, 17-AAG and rapamycin, i.e. CI<1, is encouraging, especially for the 3-drug combination. It is noted that while the $IC_{50}$ for paclitaxel as part of PEG-b-PLA micelles (Genexol-PM®) is 226±32 nM, it exerts potent anti-cancer activity in murine tumor models and in clinical trials due to a higher MTD than Taxol® (Kim et al., Clin. Cancer Res. 2004, 10, 3708).

TABLE 6-3

$IC_{50}$ for paclitaxel, 17-AAG and rapamycin solubilized by PEG-b-PLA micelles (n = 3, mean ± SD).

| Drug(s) in SDM or MDM | MCF-7 | 4T1 | A549 | molar ratio |
|---|---|---|---|---|
| PTX | 226 ± 32 | 11160 ± 4164 | 397 ± 59 | N.A |
| 17-AAG | 266 ± 48 | 118 ± 10 | 771 ± 163 | N.A |
| RAP | 255 ± 37 | >100000 | 590 ± 110 | N.A |
| PTX/17-AAG | 162 ± 17 | 92 ± 19 | 187 ± 25 | 3.2:1 (4.7:1)[1] |
| RAP/17-AAG | 177 ± 3 | 147 ± 11 | 222 ± 20 | 1:1 |
| RAP/PTX | 167 ± 6 | 4031 ± 3612 | 400 ± 37 | 1:1 |
| RAP/PTX/17-AAG | 114 ± 10 | 25 ± 1 | 94 ± 17 | 1:5:1 |

[1] A 3.2:1 molar ratio of PTX & 17-AAG was used for MCF-7 cells, and a 4.7:1 molar ratio of PTX & 17-AAG was used for both 4T1 and A549 cells.

TABLE 6-4

CI of MDM in an MCF7 breast cancer cell line, a 4T1 murine breast cancer cell line an A549 lung cancer cell line, and an LS180 colon cancer cell line.

| Drug(s) in MDM | Molar ratio | MCF-7 | 4T1 | A549 | LS180 |
|---|---|---|---|---|---|
| PTX/17-AAG | 3.2:1 (4.7:1) | 0.69 ± 0.07 | 0.14 ± 0.03 | 0.43 ± 0.06 | 1.44 ± 0.09 |
| RAP/17-AAG | 1:1 | 0.68 ± 0.01 | 0.62 ± 0.05 | 0.33 ± 0.03 | 0.88 ± 0.20 |
| RAP/PTX | 1:1 | 0.69 ± 0.02 | 0.19 ± 0.17 | 0.84 ± 0.08 | 0.04 ± 0.01 |
| RAP/PTX/ 17-AAG | 1:5:1 | 0.49 ± 0.04 | 0.04 ± 0.001 | 0.21 ± 0.03 | 0.33 ± 0.02 |

Recent Förster energy transfer experiments on PEG-b-PLA micelles suggest that they disassemble readily in blood after intravenous injection due to the action of serum proteins, resulting in drug release (Chen et al., *Langmuir* 2008, 24, 5213). Thus, it is expected that PEG-b-PLA micelles filled with paclitaxel, 17-AAG and rapamycin will disassemble readily in blood, resulting in minor changes in the pharmacokinetics of paclitaxel, 17-AAG and rapamycin. However, the higher MTD of paclitaxel, 17-AAG and rapamycin enabled by PEG-b-PLA micelles over Cremophor EL, DMSO/lipid and/or ethanol will provide higher tumor accumulation of cancer drugs and greater antitumor efficacy.

In vitro release profiles of drug(s) from SDM and MDM. The release profile of PTX, DCTX, rapamycin and 17-AAG from PEG-b-PLA micelles was evaluated by a dialysis method. SDMs or MDMs were prepared and characterized as described above. Post-micelle preparation, each sample was diluted with DD H$_2$O, to yield samples of about 0.10 mg/mL of each drug. A volume of 2.5 mL of the prepared sample was loaded into a 3 mL Slide-A-Lyzer® (Thermo Scientific Inc.) dialysis cassette with a MWCO of 20,000 g/mol. Four cassettes were used in each experiment. The cassettes were placed in 2.0 L of buffer which was changed every 3 hours to ensure sink conditions for drug(s) and polymer. A sample of 100 µL was drawn from each cassette at various sampling time intervals and then replaced with 100 µL of fresh buffer. The sampling time intervals were 0, 0.5, 2, 3, 6, 9, 12 and 24 hours. The amount of drug(s) in each sample was quantified by reverse phase HPLC.

FIGS. 3-4 and 6-8 illustrate the results of the in vitro drug release from PEG-b-PLA micelles as a single agent, and 2- and 3-drug combinations (12.5 mM PBS, pH=7.4, 37° C.). The figures show the release profiles of paclitaxel, rapamycin, and 17-AAG as single drugs or as 2- or 3-drug combinations, co-incorporated in PEG-b-PLA micelles. Rapamycin had the slowest release, followed by paclitaxel, docetaxel, and then 17-AAG (paclitaxel release as a single agent was incomplete due to drug precipitation). The release profiles of multiple-drug loaded PEG-b-PLA micelles were quite similar to the release profiles for the individual anticancer agents released by PEG-b-PLA micelles, and they corresponded well to their oil-in-water partition coefficients: log P values increased along with half-lives of drug release for PEG-b-PLA micelles (Table 6-5).

TABLE 6-5

Parameters for In Vitro Drug Release from PEG-b-PLA Micelles (Single Agent, 2- or 3-Drug Combinations).

| Anticancer agent | first-order rate constant (hr$^{-1}$) | t$_{1/2}$ (hr) | goodness of fit (r$^2$) | log P[1] |
|---|---|---|---|---|
| Paclitaxel | — | — | — | 3.0 |
| 17-AAG | 0.525 | 1.32 | 0.999 | 1.3 |
| Rapamycin | 0.081 | 8.52 | 0.990 | 5.8 |
| Paclitaxel | 0.138 | 5.01 | 0.938 | 3.0 |
| 17-AAG | 0.398 | 1.74 | 0.996 | 1.3 |
| Rapamycin | 0.069 | 10.05 | 0.991 | 5.8 |
| Paclitaxel | 0.116 | 6.00 | 0.993 | 3.0 |
| Rapamycin | 0.085 | 8.12 | 0.993 | 5.8 |
| Docetaxel | 0.317 | 2.19 | 0.999 | 2.4 |
| Rapamycin | 0.079 | 8.73 | 0.983 | 5.8 |
| 17-AAG | 0.385 | 1.80 | 0.999 | 1.3 |
| Rapamycin | 0.050 | 13.93 | 0.979 | 5.8 |
| Paclitaxel | 0.075 | 9.20 | 0.984 | 3.0 |
| 17-AAG | 0.275 | 2.52 | 0.996 | 1.3 |
| Rapamycin | 0.069 | 10.00 | 0.982 | 5.8 |
| Docetaxel | 0.306 | 2.26 | 0.993 | 2.4 |
| 17-AAG | 0.363 | 1.91 | 0.995 | 1.3 |

[1]Calculated from XlogP ver2.0. (http://pubchem.ncbi.nlm.nih.gov/). (Curve-fit with Graphic Prism v4.03).

Half-lives of drug release for PEG-b-PLA micelles were 1 to 14 hours, pointing to some degree of sustained release. However, in vivo, it is expected that the PEG-b-PLA micelles will dissociate due to the action of alpha- and beta-globulins and dilution beneath the CMC, resulting in drug release due to micelle dissociation as a possible alternative mechanism of drug release. In this situation, it is expected that PEG-b-PLA micelles will not have a major impact on the PK of paclitaxel, docetaxel, rapamycin, and 17-AAG co-incorporated in PEG-b-PLA micelles. PK experiments in rodent models will be conducted to validate this model.

The drug combinations also gave favorable acute toxicity results in mice based on changes in body weight and death (FIGS. 21-22). The three-drug combination of paclitaxel, 17-AAG, and rapamycin afforded excellent anti-tumor efficacy results in A549 non-small cell lung cancer xenograft model. These results indicate that the three-drug combination has relatively low toxicity in mice and potent anti-tumor efficacy in the A540 xenograft model.

Briefly, acute toxicity experiments were carried out in FVB female albino mice with 3 IV injections on days 0, 4, and 8, measuring body weights and monitoring survival over 12 days (FIG. 21). Not surprisingly, the acute toxicity of paclitaxel-loaded PEG-b-PLA micelles was low at a dose of 60 mg/kg (MTD for Genexol-PM®). The addition of 17-AAG or rapamycin to paclitaxel (60 mg/kg) in PEG-b-PLA micelles (2-drug combinations) did not result in significant changes in acute toxicity at 60 or 30 mg/kg, respectively (100% survival and <15% change in body weight). Surprisingly, a 3-drug combination of paclitaxel, 17-AAG, and rapamycin solubilized by PEG-b-PLA micelles (nPAR) could be injected safely into mice at 60, 60, and 30 mg/kg. Thus, combination treatment experiments in human tumor xenografts could be initiated without a reduction in the dose of paclitaxel. For a paclitaxel formulation with CrEL and ethanol, doses greater than 12 mg/kg of paclitaxel resulted in acute toxicity, which hampered dose escalation analysis using the CrEL/Ethanol formulation.

An antitumor efficacy study was done in an A549 non-small cell lung xenograft model (see FIG. 22). $5 \times 10^6$ A549 cells were injected subcutaneously in the flank region of 6-week-old female athymic mice. After about 2 weeks, tumors were palpable (200 mm$^3$), and the 3-drug combination of paclitaxel, 17-AAG, and rapamycin (nPAR) (60:60:30 mg/kg) was injected via the tail vein on days 0, 4, and 8 (arrows in FIG. 22). Tumor volumes were measured with calipers. The 3-drug combination of paclitaxel, 17-AAG, and rapamycin solubilized by PEG-b-PLA micelles had potent antitumor activity, with tumor shrinkage over 28 days after just 3 injections, whereas the volumes of tumors of control mice increased, especially over days 14-26. There was <10% change in body weight in the mice and no deaths.

Further illustrating the advantages of the drug combination that can be solubilized by the micelles described herein, FIGS. 10, 11 and 23 show in vitro free drug cytotoxicity results of several two- and three-drug combinations. FIG. 23 illustrates the in vitro free drug cytotoxicity results of rapamycin, paclitaxel and 17-AAG against MCF-7 breast cancer cell line using the resazurin assay. The data indicate that the three-drug combination of rapamycin, paclitaxel and 17-AAG is significantly more effective than any of the drugs alone, or any of the two-drug combinations. When a 5:1:1 ratio of rapamycin, paclitaxel and 17-AAG is used, the IC$_{50}$ value is further reduced by over 50%, further demonstrating the highly effective nature of this drug combination.

FIG. 10 illustrates the in vitro free drug cytotoxicity results of rapamycin, docetaxel and 17-AAG against MCF-7 breast cancer cell line using the resazurin assay. The two-drug combination of rapamycin and docetaxel, and the three-drug combination of rapamycin, docetaxel and 17-AAG show significantly lower IC$_{50}$ values than any single drug.

FIG. 11 illustrates the in vitro free drug cytotoxicity results of rapamycin, paclitaxel and 17-AAG against SKOV-3 ovarian cancer cell line using resazurin assay. Again, the data indicate that the three-drug combination of rapamycin, paclitaxel and 17-AAG is more effective than any of the drugs alone. Thus, in vitro cytotoxicity results in two different cell lines indicate that the three-drug combination of paclitaxel, 17-AAG, and rapamycin is synergistic (lung and breast cancers).

In summary, PEG-b-PLA micelles offer a simple, safe, soluble and sterile option for a multiple drug delivery of paclitaxel, 17-AAG and rapamycin, with synergy in cancer therapy. Surprisingly, PEG-b-PLA micelles act as nano-containers for multiple poorly water-soluble cancer agents, gaining sufficient water solubility for in vivo studies. Two- and 3-drug combinations of paclitaxel, 17-AAG and rapamycin exert synergistic cytotoxicity against MCF-7 breast cancer cells, providing strong indications for efficacy experiments in murine tumor models. In a preliminary experiment, PEG-b-PLA micelles filled with paclitaxel, 17-AAG and rapamycin have been injected into FVB albino mice at 60, 60 and 30 mg/kg, respectively (days 0, 4, 8), with less than 10% change in body weight and no deaths. The MTD of Genexol-PM® and Taxol® in nude mice is 60 and 20 mg/kg, respectively, on an identical schedule (Kim et al., *J. Controlled Release* 2001, 72, 191). A rapid translation of 2- or 3-drug combinations of paclitaxel, 17-AAG and rapamycin into clinical trials is anticipated. Achievement of a favorable toxicity profile and high tumor efficacy for paclitaxel, 17-AAG and rapamycin via PEG-b-PLA micelles in murine tumor models is expected, given the clinical progress for Genexol-PM®.

PEG-b-PLA micelles have been approved for parenteral use of paclitaxel in humans in South Korea and are in phase II clinical trials in the USA as an alternative to Cremophor EL® and Abraxane®. The PEG-b-PLA micelles described herein uniquely solubilize 2- and 3-drug combinations of paclitaxel, 17-AAG, and rapamycin (PAR). PEG-b-PLA micelles with PAR exert synergistic anti-cancer activity against MCF-7 and 4T1 breast cancer and A549 non-small cell lung cancer cells. PEG-b-PLA micelles containing PAR can be dosed at 60, 60, and 30 mg/kg in mice on days 0, 4, and 8. PEG-b-PLA micelles with PAR dosed at 60, 60, and 30 mg/kg on days 0, 4, and 8 induce tumor regression in an A549 NSCLC xenograft model. Accordingly, the compositions described herein provide simple and safe methods for solubilizing numerous anti-cancer drugs that act in a synergistic manner to provide new treatments for a variety of cancers.

Example 7

Pharmaceutical Dosage Forms

The following formulations illustrate representative pharmaceutical dosage forms that may be used for the therapeutic administration of a micellar formulation described herein (hereinafter referred to as 'Composition X'):

| (i) Injection 1 (1 mg/mL) | mg/mL |
|---|---|
| 'Composition X' | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (ii) Injection 2 (10 mg/mL) | mg/mL |
|---|---|
| 'Composition X' | 10.0 |
| Monobasic sodium phosphate | 0.3 |
| Dibasic sodium phosphate | 1.1 |
| Polyethylene glycol 400 | 200.0 |
| 01N Sodium hydroxide solution (pH adjustment to 7.0-7.5) | q.s. |
| Water for injection | q.s. ad 1 mL |

| (iii) Aerosol | mg/can |
|---|---|
| 'Composition X' | 20 |
| Oleic acid | 10 |
| Trichloromonofluoromethane | 5,000 |
| Dichlorodifluoromethane | 10,000 |
| Dichlorotetrafluoroethane | 5,000 |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Composition X'. Aerosol formulation (iii) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

All publications, patents, and patent documents are incorporated by reference herein, as though individually incorporated by reference. While specific embodiments have been described above with reference to the disclosed embodiments and examples, these embodiments and examples are only illustrative and do not limit the scope of the invention. Changes and modifications can be made in accordance with ordinary skill in the art without departing from the invention in its broader aspects as defined in the following claims.

What is claimed is:

1. A composition comprising micelles encapsulating three drugs,
   wherein the micelles comprise poly(ethylene glycol)-block-poly(lactic acid) polymers;
   the hydrophobic poly(lactic acid) block of the polymers orient toward the interior of each micelle, and the hydrophilic poly(ethylene glycol) block of the polymers orient toward the exterior of each micelle;
   the molecular weight of the poly(ethylene glycol) block is about 1,000 to about 35,000 g/mol and the molecular weight of the poly(lactic acid) block is about 1,000 to about 15,000 g/mol;
   the drug loading of the micelles is about 1 wt. % to about 50 wt. % with respect to the mass of the micelles;
   the three drugs are non-covalently encapsulated in the interior of the micelles;
   the three drugs are paclitaxel, 17-AAG, and rapamycin; docetaxel, 17-AAG, and rapamycin; or paclitaxel, etoposide, and 17-AAG; and
   the composition is substantially free of ethanol, dimethyl sulfoxide, castor oil, and castor oil derivatives.

2. The composition of claim 1 wherein the combined drug loading in the micelles is about 10 wt. % to about 40 wt. %.

3. The composition of claim 1 further comprising an aqueous vehicle, wherein the concentration of the drugs is about 0.6 mg/mL to about 40 mg/mL, with respect to the volume of the aqueous vehicle.

4. The composition of claim 1 wherein the encapsulated drugs have an aqueous solubility of about 1 mg/mL to about 20 mg/mL when contacted with an aqueous environment.

5. The composition of claim 1 wherein the composition comprises less than about 2 wt. % of ethanol, dimethyl sulfoxide, castor oil, and castor oil derivatives.

6. The composition of claim 1 wherein the molecular weight of the poly(ethylene glycol) block is about 1,500 to about 14,000 g/mol, the molecular weight of the poly(lactic acid) block is about 1,500 to about 7,000 g/mol, and the average diameter of the micelles is about 30 nm to about 50 nm.

7. The composition of claim 1 wherein each of the drugs are incorporated together into individual PEG-PLA micelles.

8. The composition of claim 1 wherein the each drug is incorporated separately into PEG-PLA micelles, and the micelles are combined in a single aqueous vehicle.

9. A pharmaceutical composition comprising the composition of claim 1 and an aqueous carrier, wherein the composition is formulated for intravenous or intraperitoneal administration and the aqueous carrier comprises saline or an aqueous carbohydrate solution.

10. A method of inhibiting or killing cancer cells comprising contacting the cancer cells with an effective inhibitory or lethal amount of a composition of claim 1.

11. The method of claim 10 wherein the contacting is in vivo.

12. The method of claim 10 wherein the contacting is in vitro.

13. The method of claim 10 wherein the cancer cells are brain tumor cells, breast cancer cells, colon cancer cells, head and neck cancer cells, lung cancer cells, lymphoma cells, melanoma cells, neuroblastoma cells, ovarian cancer cells, pancreatic cancer cells, prostate cancer cells, or leukemia cells.

14. A composition for the delayed release of paclitaxel and 17-AAG, and rapamycin; docetaxel, 17-AAG, and rapamycin; or paclitaxel, etoposide, and 17-AAG; comprising a composition of claim 1 and an aqueous carrier, wherein less than 50 wt. % of the drugs are released from the micelles after exposure to an aqueous environment or to the body fluid of a mammal for about two hours.

15. The composition of claim 1 wherein the micelles encapsulate a synergistic three drug combination, and the three drugs are paclitaxel, 17-AAG, and rapamycin, or docetaxel, 17-AAG, and rapamycin.

16. The composition of claim 1 wherein the drug loading of the micelles is 32 wt. % to about 50 wt. % with respect to the mass of the micelles.

17. The composition of claim 1 wherein the drug loading of the micelles is 32 wt. % to 41.6 wt. % with respect to the mass of the micelles.

18. The composition of claim 9 wherein the drug loading of the micelles is 32 wt. % to about 50 wt. % with respect to the mass of the micelles.

19. The composition of claim 9 wherein the drug loading of the micelles is 32 wt. % to 41.6 wt. % with respect to the mass of the micelles.

20. A composition comprising micelles encapsulating three drugs, wherein the micelles are poly(ethylene glycol)-block-poly(lactic acid) polymers;
   the hydrophobic poly(lactic acid) block of the polymers orient toward the interior of each micelle, and the hydrophilic poly(ethylene glycol) block of the polymers orient toward the exterior of each micelle;
   the molecular weight of the poly(ethylene glycol) block is about 1,000 to about 35,000 g/mol and the molecular weight of the poly(lactic acid) block is about 1,000 to about 15,000 g/mol;
   the drug loading of the micelles is about 5 wt. % to about 50 wt. % with respect to the mass of the micelles;
   the three drugs are paclitaxel, 17-AAG, and rapamycin; and
   the composition comprises less than about 0.1 wt. % of ethanol, dimethyl sulfoxide, castor oil, and castor oil derivatives.

21. A composition comprising micelles encapsulating three drugs, wherein the micelles are poly(ethylene glycol)-block-poly(lactic acid) polymers;
   the hydrophobic poly(lactic acid) block of the polymers orient toward the interior of each micelle, and the hydrophilic poly(ethylene glycol) block of the polymers orient toward the exterior of each micelle;
   the molecular weight of the poly(ethylene glycol) block is about 1,000 to about 35,000 g/mol and the molecular weight of the poly(lactic acid) block is about 1,000 to about 15,000 g/mol;
   the drug loading of the micelles is about 5 wt. % to about 50 wt. % with respect to the mass of the micelles;
   the three drugs are docetaxel, 17-AAG, and rapamycin; and
   the composition comprises less than about 0.1 wt. % of ethanol, dimethyl sulfoxide, castor oil, and castor oil derivatives.

22. A composition comprising micelles encapsulating three drugs, wherein the micelles are poly(ethylene glycol)-block-poly(lactic acid) polymers;
- the hydrophobic poly(lactic acid) block of the polymers orient toward the interior of each micelle, and the hydrophilic poly(ethylene glycol) block of the polymers orient toward the exterior of each micelle;
- the molecular weight of the poly(ethylene glycol) block is about 1,000 to about 35,000 g/mol and the molecular weight of the poly(lactic acid) block is about 1,000 to about 15,000 g/mol;
- the drug loading of the micelles is about 5 wt. % to about 50 wt. % with respect to the mass of the micelles;
- the three drugs are paclitaxel, etoposide, and 17-AAG; and
- the composition comprises less than about 0.1 wt. % of ethanol, dimethyl sulfoxide, castor oil, and castor oil derivatives.

* * * * *